United States Patent
Chen et al.

(10) Patent No.: US 10,357,477 B2
(45) Date of Patent: Jul. 23, 2019

(54) ANTICANCER COMPOUNDS

(71) Applicant: REGENTS OF THE UNIVERSITY OF MINNESOTA, Minneapolis, MN (US)

(72) Inventors: Liqiang Chen, Minneapolis, MN (US); Teng Ai, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/703,191

(22) Filed: Sep. 13, 2017

(65) Prior Publication Data

US 2018/0071258 A1 Mar. 15, 2018

Related U.S. Application Data

(60) Provisional application No. 62/394,050, filed on Sep. 13, 2016.

(51) Int. Cl.
| | |
|---|---|
| C07D 401/04 | (2006.01) |
| C07D 401/12 | (2006.01) |
| C07D 231/12 | (2006.01) |
| A61K 31/4155 | (2006.01) |
| A61K 31/4418 | (2006.01) |
| A61K 31/166 | (2006.01) |
| C07D 213/46 | (2006.01) |
| A61K 31/03 | (2006.01) |
| C07D 231/40 | (2006.01) |
| A61K 31/05 | (2006.01) |
| A61P 35/00 | (2006.01) |
| A61P 35/02 | (2006.01) |
| A61P 35/04 | (2006.01) |

(52) U.S. Cl.
CPC .......... *A61K 31/4155* (2013.01); *A61K 31/03* (2013.01); *A61K 31/05* (2013.01); *A61K 31/166* (2013.01); *A61K 31/4418* (2013.01); *C07D 213/46* (2013.01); *C07D 231/12* (2013.01); *C07D 231/40* (2013.01); *C07D 401/04* (2013.01); *C07D 401/12* (2013.01)

(58) Field of Classification Search
CPC ... C07D 401/12; C07D 401/04; C07D 231/12
See application file for complete search history.

(56) References Cited

U.S. PATENT DOCUMENTS

2009/0325956 A1* 12/2009 Taniguchi .......... A61K 31/5377
514/235.5

OTHER PUBLICATIONS

Al, et al., "N-(1-Benzyl-3,5-dimethyl-1H-pyrazol-4-yl)benzamides: Antiproliferative Activity and Effects on mTORC1 and Autophagy", ACS Med Chem Lett 8(1), 90-95 (2017).
Choi, et al., "Autophagy in human health and disease", N Engl J Med 368, 651-662 (2013).
Dong, et al., "Autophagy as a target for hematological malignancy therapy", Blood Rev 30(5), 369-380 (2016).
Fujii, et al., "Autophagy is activated in pancreatic cancer cells and correlates with poor patient outcome", Cancer Sci 99, 1813-1819 (2008).
Galluzzi, et al., "Autophagy in malignant transformation and cancer progression", EMBO J 34, 856-880 (2015).
Garrido-Laguna, et al., "Pancreatic cancer: from state-of-the-art treatments to promising novel therapies", Nat Rev Clin Oncol 12, 319-334 (2015).
Gomez, et al., Semin cancer Biol 35, 11-19 (2015).
He, et al., "Regulation mechanisms and signaling pathways of autophagy", Annu Rev Genet 43, 67-93 (2009).
Hezel, et al., "Genetics and biology of pancreatic ductal adenocarcinoma", Genes Dev 20(10), 1218-1249 (2006).
Jones, et al., "Core signaling pathways in human pancreatic cancers revealed by global genomic analyses", Science 321(5897), 1801-1806 (2008).
Rosenfeldt, et al., "p53 status determines the role of autophagy in pancreatic tumour development", Nature 504, 296-300 (2013).
Siegel, et al., "Cancer statistics, 2015", CA Cancer J Clin 65, 5-29 (2015).
Spadi, et al., "Current therapeutic strategies for advanced pancreatic cancer: A review for clinicians", World J Clin Oncol 7, 27-43 (2016).
Sui, et al., "Autophagy and chemotherapy resistance: a promising therapeutic target for cancer treatment", Cell Death Dis 4, 3838 (2013).
Yang, et al., "Autophagy is critical for pancreatic tumor growth and progression in tumors with p53 alterations", Cancer Discov 4, 905-913 (2014).
Yang, et al., "Pancreatic cancers require autophagy for tumor growth", Genes Dev 25, 717-729 (2011).

* cited by examiner

*Primary Examiner* — Susanna Moore
(74) *Attorney, Agent, or Firm* — Viksnins Harris Padys Malen LLP

(57) ABSTRACT

The invention provides compounds having the general formula I:

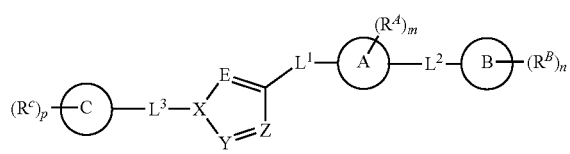

and salts thereof, wherein the variables $R^A$, $R^B$, $R^C$, $L^1$, $L^2$, $L^3$, A, B, C, X, Y, Z, E, m, n, and p have the meaning as described herein, and compositions containing such compounds and methods for using such compounds and compositions.

14 Claims, No Drawings

ANTICANCER COMPOUNDS

CROSS-REFERENCE TO RELATED APPLICATIONS

This application claims priority to U.S. Provisional Application No. 62/394,050, filed 13 Sep. 2016. The entire content of U.S. Provisional Application No. 62/394,050 is hereby incorporated by reference herein.

BACKGROUND OF THE INVENTION

Pancreatic ductal adenocarcinoma (PDAC) is the fourth leading cause of death by cancer in the United States with estimated 48,960 new cases and 40,560 deaths in 2015 (Siegel, R. L. et al. *CA. Cancer J. Clin.* 2015, 65, 5-29). With a five-year overall survival rate of merely 7 percent, PDAC is the most lethal cancer among major malignancies. Its poor prognosis is partly due to the fact that PDAC is usually diagnosed at advanced stages. Moreover, pancreatic cancer cells acquire a large number of genetic mutations and are notoriously resistant to apoptotic cell death, an established cancer cell-killing mechanism elicited by anti-cancer agents (Jones, S. et al. *Science* 2008, 321, 1801-1806; and Hezel, A. F. et al. *Genes Dev.* 2006, 20, 1218-1249). Despite numerous efforts, there still is a dire lack of effective therapeutic options for advanced pancreatic cancer (Garrido-Laguna, I. et al. *Nat. Rev. Clin. Oncol.* 2015, 12, 319-334; and Spadi, R. et al. *World J. Clin. Oncol.* 2016, 7, 27-43). Modulation of macroautophagy (hereafter referred to as autophagy) has been proposed as a promising strategy (Gomez, V. E. et al. *Semin. Cancer Biol.* 2015, 35, 11-19).

Autophagy is a conserved cellular process through which cytosolic components, such as proteins and organelles, are sequestered, degraded, and recycled (He, C. et al. *Annu. Rev. Genet.* 2009, 43, 67-93; and Choi, A. M. et al. *N. Engl. J. Med.* 2013, 368, 651-662). The precise roles of autophagy in tumorigenesis and cancer therapy still remain to be defined due to the heterogeneous nature of cancers and the complexity of the autophagy machinery (Galluzzi, L. et al. *EMBO J.* 2015, 34, 856-880). Studies have shown that autophagy plays different or even opposite roles depending on the cancer type and the stage of tumor progression. Currently, it is generally accepted that autophagy behaves as a tumor suppressor in normal cells in part because it removes damaged cellular components. Nevertheless, increasing evidence shows that autophagy is a cytoprotective mechanism often exploited by established cancer cells to cope with their harsh microenvironment and cellular stresses induced by chemotherapies. A number of anticancer agents with diverse mechanisms of action have been shown to induce autophagy (Sui, X. et al. *Cell Death Dis.* 2013, 4, e838; and Dong, Z. et al. *Blood Rev.* 2016, doi: 10.1016/j.blre.2016.04.005). More importantly, autophagy inhibitors enhance the efficacy of many anticancer agents (Sui, X. et al. *Cell Death Dis.* 2013, 4, e838). For pancreatic cancer, it has been shown that autophagy is elevated and required for de novo tumor growth and inhibition of autophagy leads to robust tumor regression (Fujii, S. et al. *Cancer Sci.* 2008, 99, 1813-1819; and Yang, S. et al. *Genes Dev.* 2011, 25, 717-729); however, the status of p53, whose mutation is commonly seen in pancreatic cancer patients, may determine the outcome of autophagy inhibition (Rosenfeldt, M. T. et al. *Nature* 2013, 504, 296-300; and Yang, A. et al. *Cancer Discov.* 2014, 4, 905-913). Despite the complexity of autophagy inhibition as a therapeutic strategy, these studies suggest that disabling the pro-survival autophagy machinery hijacked by cancer cells might represent a viable approach to promote cell death and reduce drug resistance in refractory cancers such as pancreatic cancer (Gomez, V. E. et al. *Semin. Cancer Biol.* 2015, 35, 11-19; and Sui, X. et al. *Cell Death Dis.* 2013, 4, e838).

Therefore, there is a need for new compounds to treat cancer, especially pancreatic cancer.

SUMMARY OF THE INVENTION

The invention provides compounds that treat cancer, especially pancreatic cancer.

Accordingly, the invention provides a compound of formula I:

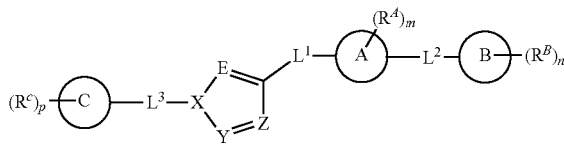

wherein:

ring A is aryl or heteroaryl;

ring B is aryl, heteroaryl, carbocycle or heterocycle;

ring C is aryl or heteroaryl;

$L^1$ is $C_{1-4}$ alkylene, $-L^A-O-L^B-$, $-L^A-S-L^B$, $L^A-NR^1-L^B-$, $-L^A-NR^1C(O)-L^B-$, $-L^A-NR^1SO_2-L^B-$, $-L^A-C(O)NR^1-L^B-$, or $-L^A-SO_2NR^1-L^B-$; wherein each $R^1$ is independently hydrogen or $C_{1-4}$ alkyl; each $L^A$ is independently absent or $C_{1-4}$ alkylene; each $L^B$ is independently absent or $C_{1-4}$ alkylene;

$L^2$ is $C_{1-4}$ alkylene, $-L^C-O-L^D-$, $-L^C-S-L^D$, $L^C-NR^2-L^D-$, $-L^C-NR^2C(O)-L^D-$, or $-L^C-C(O)NR^2-L^D-$; wherein each $R^2$ is independently hydrogen or $C_{1-4}$ alkyl; each $L^C$ is independently absent or $C_{1-4}$ alkylene; each $L^D$ is independently absent or $C_{1-4}$ alkylene;

$L^3$ is $C_{1-4}$ alkylene, $-L^E-O-L^F-$, $-L^E-S-L^F$, $-L^E-NR^{11}-L^F-$, $-L^E-NR^{11}C(O)-L^F-$, or $-L^E-C(O)NR^{11}-L^F-$; wherein each $R^{11}$ is independently hydrogen or $C_{1-4}$ alkyl; each $L^E$ is independently absent or $C_{1-4}$ alkylene; each $L^F$ is independently absent or $C_{1-4}$ alkylene;

X is N or $C-R^X$; wherein $R^X$ is hydrogen, $C_{1-4}$ alkyl, $C_{1-4}$ haloalkyl, halo, $-OR^3$, $-SR^3$, $-N(R^3)_2$, $-NO_2$ or $-CN$; wherein each $R^3$ is independently hydrogen or $C_{1-4}$ alkyl;

Y is N or $C-R^Y$; wherein $R^Y$ is hydrogen, $C_{1-4}$ alkyl, $C_{1-4}$ haloalkyl, halo, $-OR^4$, $-SR^4$, $-N(R^4)_2$, $-NO_2$ or $-CN$; wherein each $R^4$ is independently hydrogen or $C_{1-4}$ alkyl;

Z is N or $C-R^Z$; wherein $R^Z$ is hydrogen, $C_{1-4}$ alkyl, $C_{1-4}$ haloalkyl, halo, $-OR^5$, $-SR^5$, $-N(R^5)_2$, $-NO_2$ or $-CN$; wherein each $R^5$ is independently hydrogen or $C_{1-4}$ alkyl;

E is N or $C-R^E$; wherein $R^E$ is hydrogen, $C_{1-4}$ alkyl, $C_{1-4}$ haloalkyl, halo, $-OR^6$, $-SR^6$, $-N(R^6)_2$, $-NO_2$ or $-CN$; wherein each $R^6$ is independently hydrogen or $C_{1-4}$ alkyl;

each $R^A$ is independently $C_{1-4}$ alkyl, $C_{1-4}$ haloalkyl, halo, $-OR^7$, $-SR^7$, $-N(R^7)_2$, $-NO_2$ or $-CN$; wherein each $R^7$ is independently hydrogen or $C_{1-4}$ alkyl;

each $R^B$ is independently $C_{1-4}$ alkyl, $C_{1-4}$ haloalkyl, halo, $-OR^8$, $-SR^8$, $-N(R^8)_2$, $-NO_2$ or $-CN$; wherein each $R^8$ is independently hydrogen or $C_{1-4}$ alkyl;

each $R^C$ is independently $C_{1-4}$ alkyl, $C_{1-4}$ haloalkyl, halo, —$OR^9$, —$SR^9$, —$N(R^9)_2$, —$NO_2$, —CN, —$C(O)N(R^9)_2$ or —$NR^9C(O)R^{10}$; wherein each $R^9$ is independently hydrogen, $C_{1-4}$ alkyl or aryl; $R^{10}$ is $C_{1-4}$ alkyl or aryl;

m is 0, 1, 2, 3, or 4;

n is 0, 1, 2, 3, or 4; and p is 0, 1, 2, 3, or 4;

provided that at least one of X, Y, Z and E is N;

or a pharmaceutically acceptable salt thereof.

The invention also provides a pharmaceutical composition comprising a compound of formula I or a pharmaceutically acceptable salt thereof, and a pharmaceutically acceptable carrier.

The invention also provides a method for treating cancer in an animal (e.g., a mammal, such as a human) comprising administering a compound of formula I or a pharmaceutically acceptable salt thereof to the animal.

The invention also provides processes and intermediates disclosed herein that are useful for preparing a compound of formula I or a salt thereof.

DETAILED DESCRIPTION

The term "alkyl", by itself or as part of another substituent, means, unless otherwise stated, a straight or branched chain hydrocarbon radical, having the number of carbon atoms designated (i.e., $C_{1-4}$ means one to four carbons). Non limiting examples of "alkyl" include methyl, ethyl, propyl, isopropyl, butyl, iso-butyl, sec-butyl.

The term "alkylene" by itself or as part of another substituent means a divalent radical derived from an alkane (including straight and branched alkanes), as exemplified by —$CH_2CH_2CH_2CH_2$— and —$CH(CH_3)CH_2CH_2$—.

The term "halo" means fluoro, chloro, bromo, or iodo.

The term "haloalkyl" means an alkyl that is optionally substituted with one or more (e.g., 1, 2, 3, 4, or 5) halo. Non limiting examples of "haloalkyl" include iodomethyl, bromomethyl, chloromethyl, fluoromethyl, trifluoromethyl, 2-chloroethyl, 2-fluoroethyl, 2,2,2-trifluoroethyl 2,2-difluoroethyl and pentafluoroethyl.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1, 2, 3, 4-tetrahydronaphthyl, anthracenyl, and the like.

The term "heteroaryl" as used herein refers to a 3-6 membered single aromatic ring that has at least one (e.g., 1, 2, 3 or 4) atom other than carbon in the ring, wherein the atom is selected from the group consisting of oxygen, nitrogen and sulfur; "heteroaryl" also includes 7-20 membered multiple condensed ring systems that have at least one such aromatic ring, which multiple condensed ring systems are further described below. The rings of the multiple condensed ring system can be connected to each other via fused, spiro and bridged bonds when allowed by valency requirements. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

The term "carbocycle" refers to a single saturated (i.e., cycloalkyl) or a single partially unsaturated (e.g., cycloalkenyl, cycloalkadienyl, etc.) ring having 3 to 7 carbon atoms (i.e. $(C_3-C_7)$carbocycle). The term "carbocycle" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, spiro[4.5]decane, etc), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" may also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl and cycloheptyl.

The term "heterocycle" refers to a saturated or partially unsaturated ring system radical having the overall having from 3-20 ring atoms that contain from one to ten heteroatoms selected from N, O, and S. Unless otherwise stated, a "heterocycle" ring can be a monocyclic, a bicyclic, spirocyclic or a polycylic ring system. Non limiting examples of "heterocycle" rings include pyrrolidine, piperidine, N-methylpiperidine, imidazolidine, pyrazolidine, butyrolactam, valerolactam, imidazolidinone, hydantoin, dioxolane, phthalimide, piperidine, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, tropane, 2-azaspiro[3.3] heptane, (1R,5S)-3-azabicyclo[3.2.1]octane, (1s,4s)-2-azabicyclo[2.2.2]octane, (1R,4R)-2-oxa-5-azabicyclo[2.2.2] octane and the like. A "heterocycle" group can be attached to the remainder of the molecule through one or more ring carbons or heteroatoms.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

In one embodiment, the compound is a compound of formula Ia:

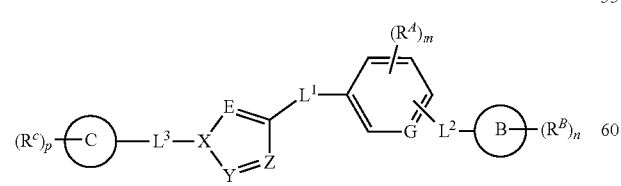

Ia wherein G is N or CH;
m is 0, 1, 2, or 3;
or a pharmaceutically acceptable salt thereof.

In one embodiment, the compound is a compound of formula Ib:

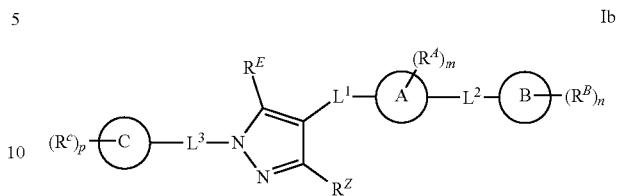

Ib or a pharmaceutically acceptable salt thereof.

In one embodiment, the compound is a compound of formula Ic:

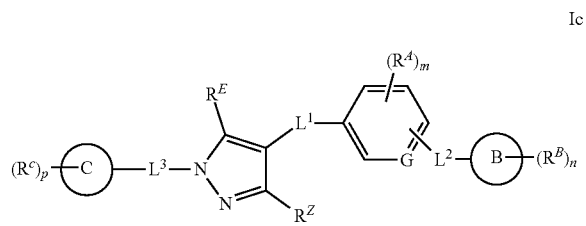

Ic wherein G is N or CH;
m is 0, 1, 2, or 3;
or a pharmaceutically acceptable salt thereof.
In one embodiment, $R^Z$ is $C_{1-4}$ alkyl.
In one embodiment, $R^Z$ is methyl.
In one embodiment, $R^E$ is $C_{1-4}$ alkyl.
In one embodiment, $R^E$ is methyl.
In one embodiment, m is 0.
In one embodiment, ring B is phenyl, pyridyl, cyclohexyl or naphthalenyl.
In one embodiment, each $R^B$ is independently $C_{1-4}$ alkyl, $C_{1-4}$ haloalkyl, halo, —$OR^8$, —$NO_2$ or CN; wherein $R^8$ is hydrogen or $C_{1-4}$ alkyl.
In one embodiment, each $R^B$ is independently $CH_3$, —$OCH_3$, —Cl, —CN, —$NO_2$, or $CF_3$.
In one embodiment, n is 0, 1, or 2.
In one embodiment, the group

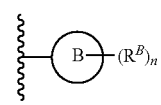

is selected from the group consisting of:

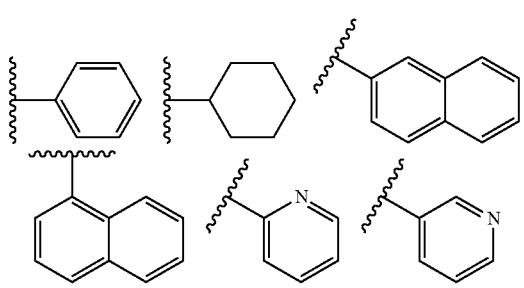

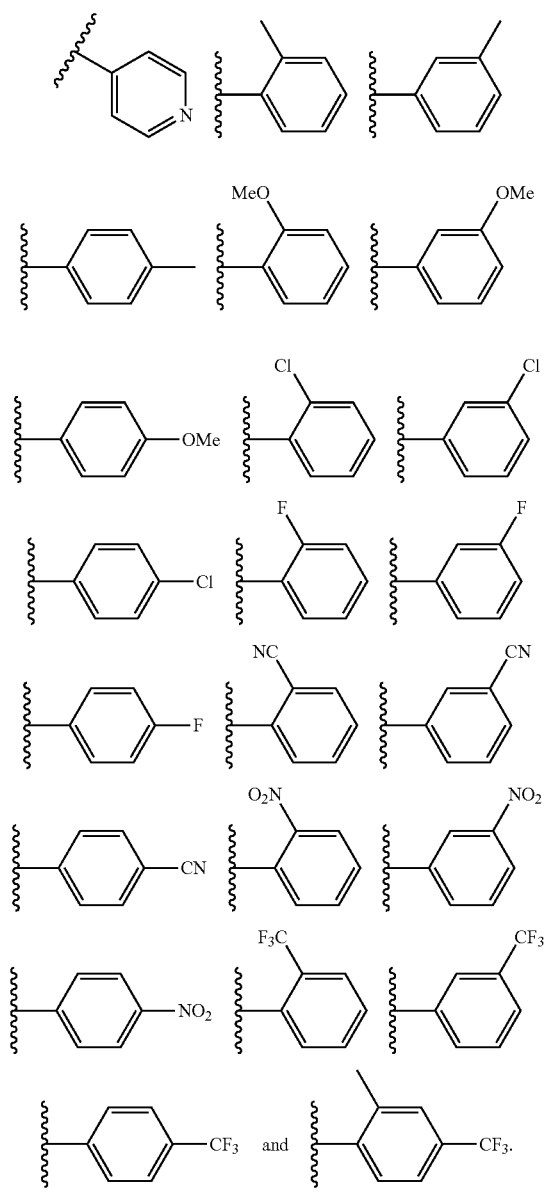

In one embodiment, ring C is phenyl or pyridyl.

In one embodiment, each $R^C$ is independently —$N(R^9)_2$, —$NO_2$, —$C(O)N(R^9)_2$ or —$NR^9C(O)R^{10}$; wherein each $R^9$ is independently hydrogen, $C_{1-4}$ alkyl or aryl; $R^{10}$ is $C_{1-4}$ alkyl or aryl.

In one embodiment, each $R^C$ is independently $C(O)NH_2$, —$C(O)NHMe$, —$C(O)N(Me)_2$, —$C(O)NHEt$, —$C(O)NH^iPr$, —$C(O)NHPh$, —$NO_2$, —$NH_2$, or —$NHC(O)Me$.

In one embodiment, p is 0 or 1.

In one embodiment, the group

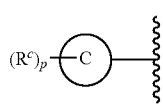

is selected from the group consisting of:

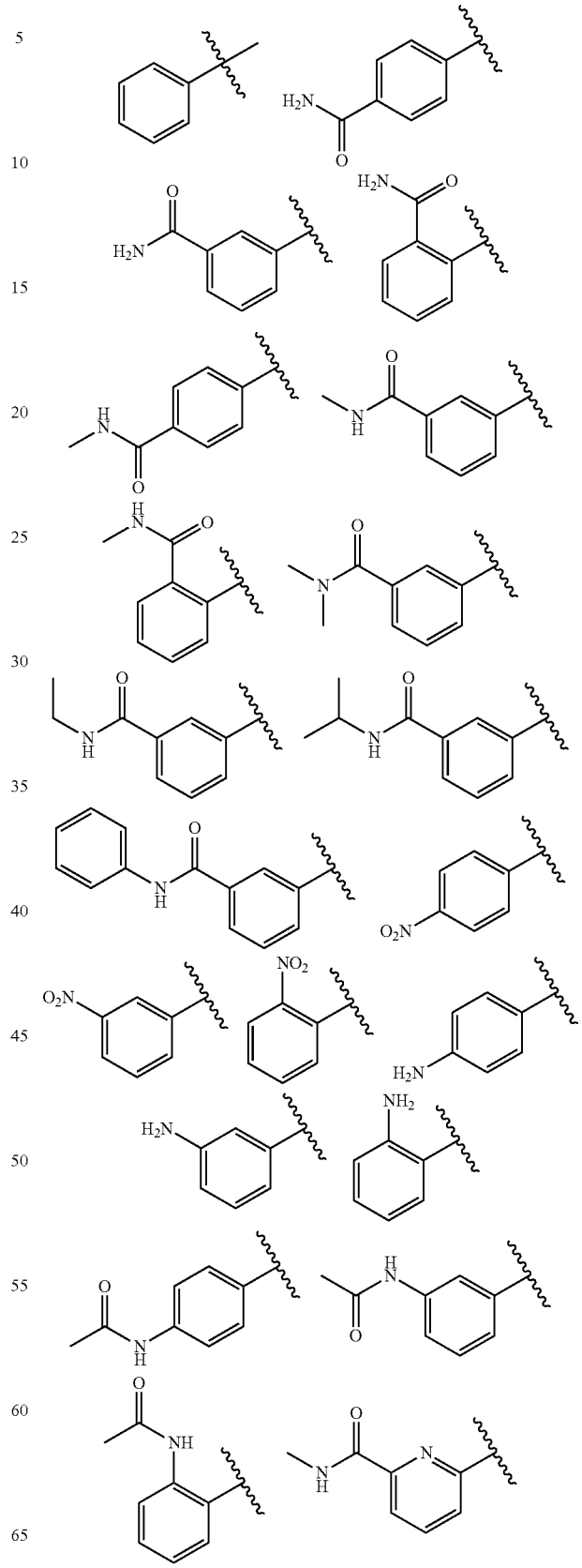

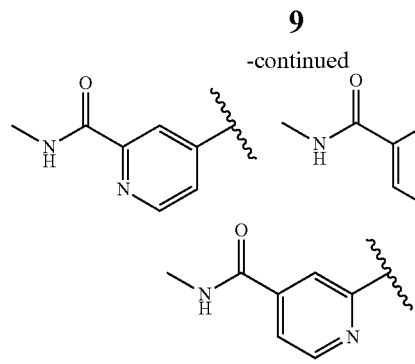
and

In one embodiment, $L^1$ is -$L^A$-$NR^1$-$L^B$-, -$L^A$-$NR^1C(O)$-$L^B$-, or -$L^A$-$NR^1SO_2$-$L^B$-; wherein each $R^1$ is independently hydrogen or $C_{1-4}$ alkyl; each $L^A$ is independently absent or $C_{1-4}$ alkylene; each $L^B$ is independently absent or $C_{1-4}$ alkylene.

In one embodiment, $L^1$ is —NMeC(O)—, —NHC(O)—, —NHCH$_2$—, or —NHSO$_2$—.

In one embodiment, $L^1$ is —NHC(O)—.

In one embodiment, $L^2$ is $C_{1-4}$ alkylene, -$L^C$-$NR^2$-$L^D$-, -$L^C$-O-$L^D$-, -$L^C$-S-$L^D$, or -$L^C$-(CO)$NR^2$-$L^D$-; wherein each $R^2$ is independently hydrogen or $C_{1-4}$ alkyl; each $L^C$ is independently absent or $C_{1-4}$ alkylene; each $L^D$ is independently absent or $C_{1-4}$ alkylene.

In one embodiment, $L^2$ is —CH$_2$O—, —CH(CH$_3$)O—, —CH$_2$S—, —CH$_2$NH—, —CH$_2$CH$_2$—, —(CO)NH—, —OCH$_2$—, or —O—.

In one embodiment, $L^2$ is —CH$_2$O—.

In one embodiment, $L^3$ is $C_{1-4}$ alkylene.

In one embodiment, $L^3$ is —CH$_2$— or —CH(CH$_3$)—.

In one embodiment, the invention provides a compound selected from the group consisting of:

A1

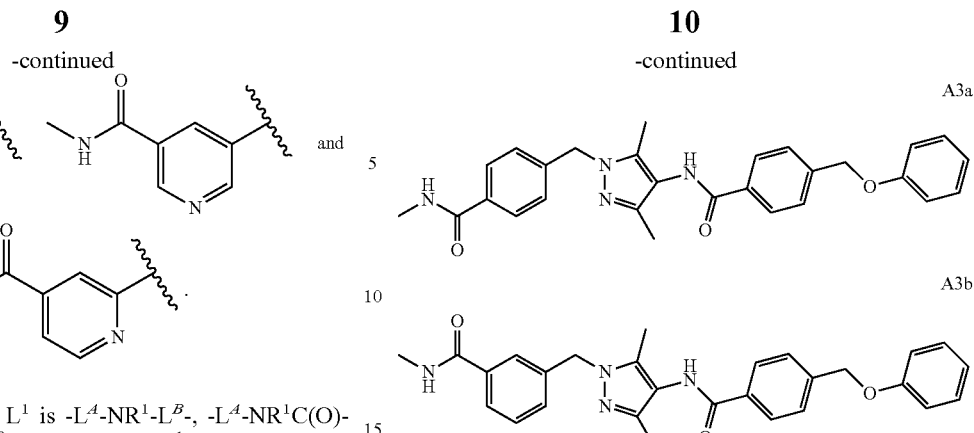

A2a

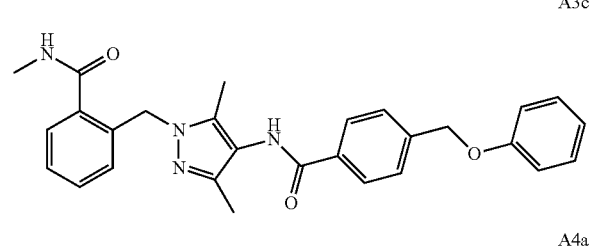

A2b

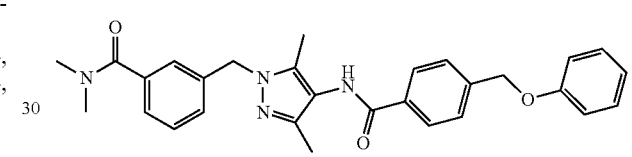

A2c

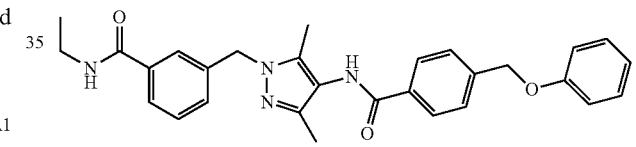

A3a

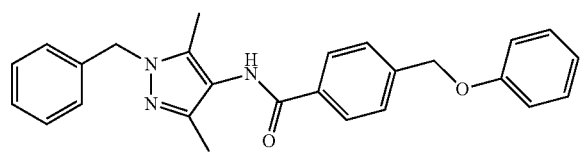

A3b

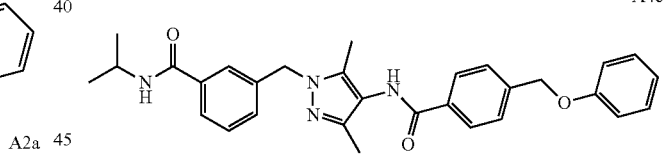

A3c

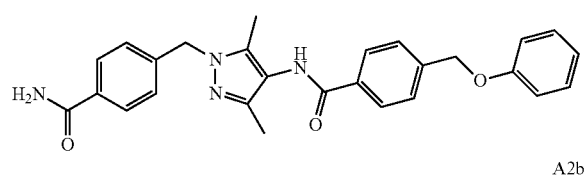

A4a

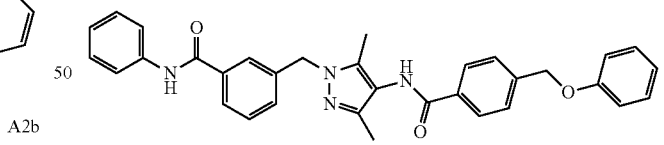

A4b

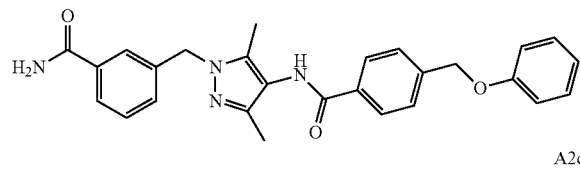

A4c

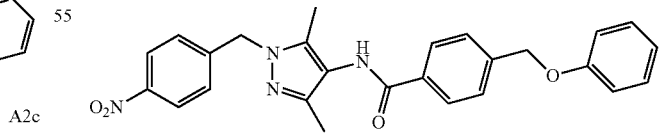

A4d

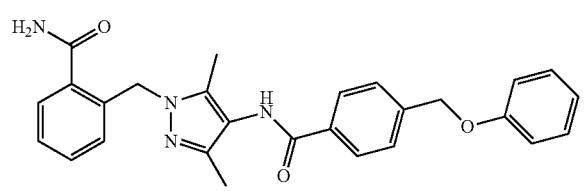

A5a

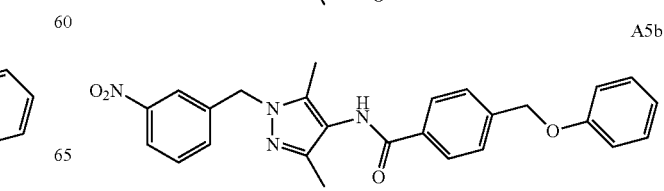

A5b

-continued

A5c, A6a, A6b, A6c, A7a, A7b, A7c, B1, B2

-continued

B3, C1, C2, C3, C4, C5, C6, C7, D1

D2
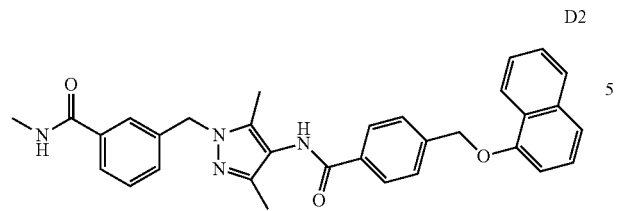
D3a
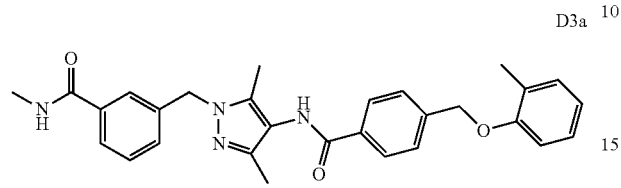
D3b
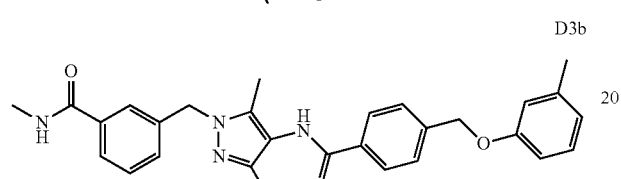
D3c
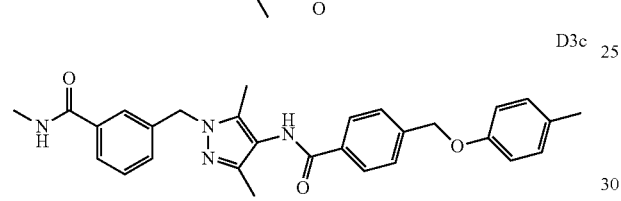
D4a
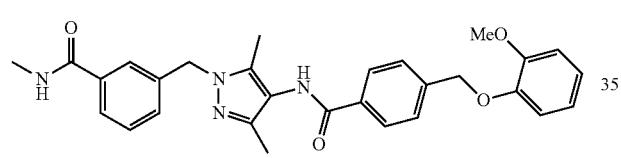
D4b
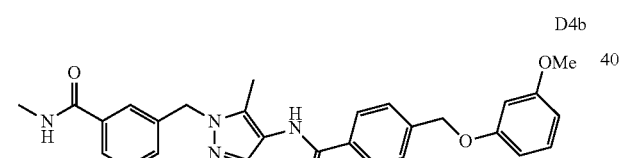
D4c
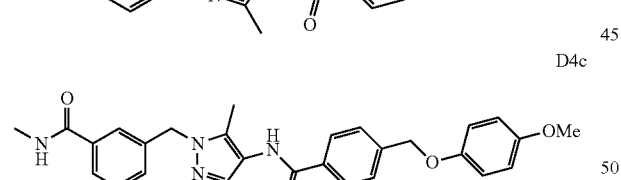
D5a
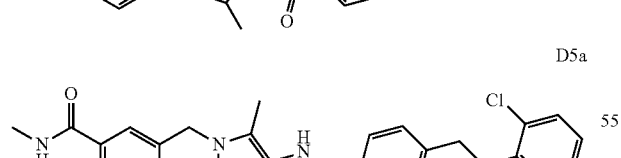
D5b
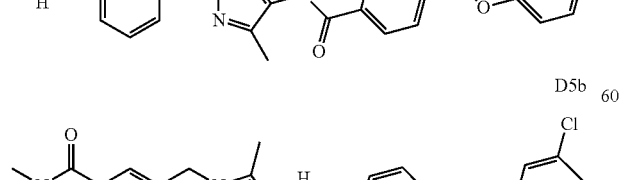
D5c
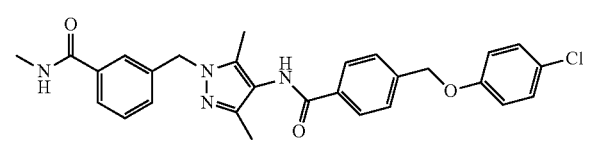
D6a
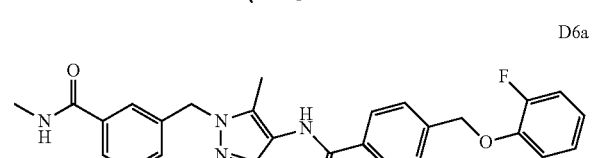
D6b
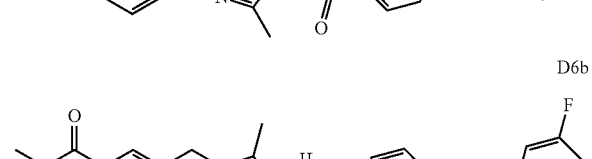
D6c
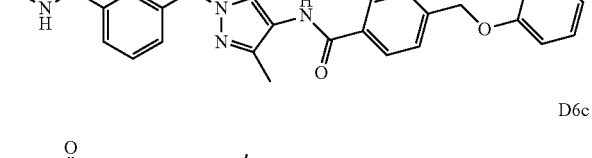
D7a
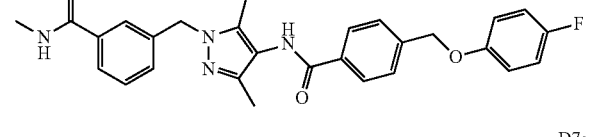
D7b
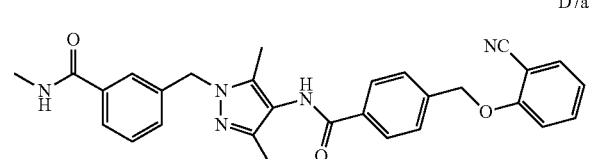
D7c
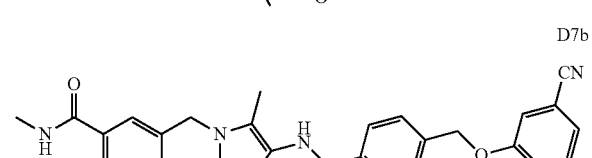
D8a
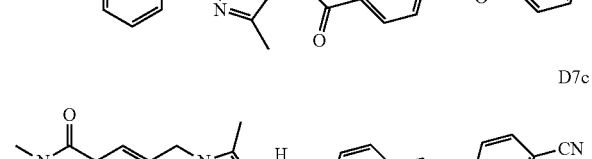
D8b
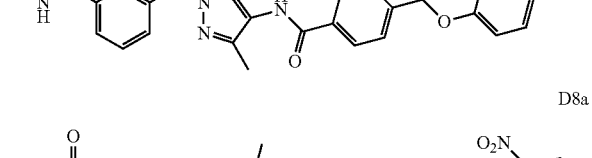

D8c
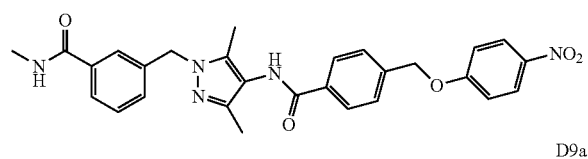
D9a
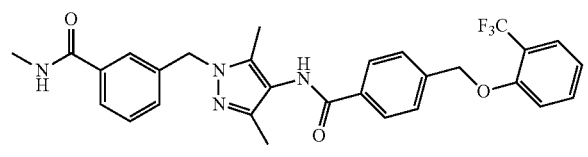
D9b
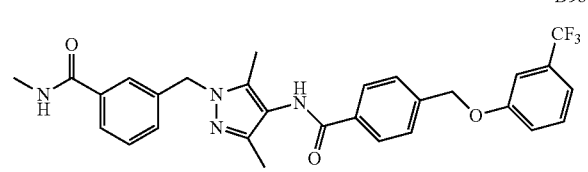
D9c
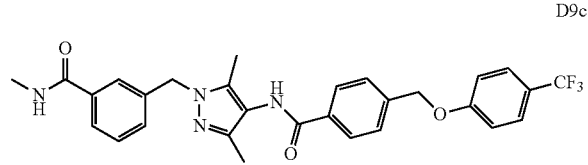
D10
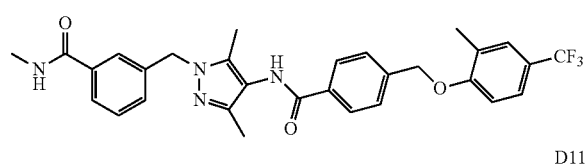
D11
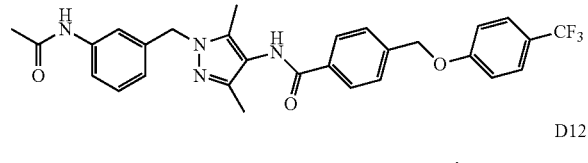
D12
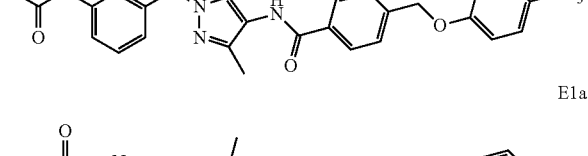
E1a
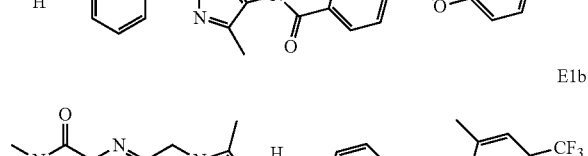
E1b
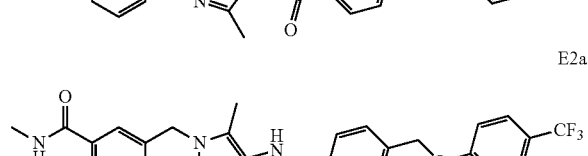
E2a
E2b
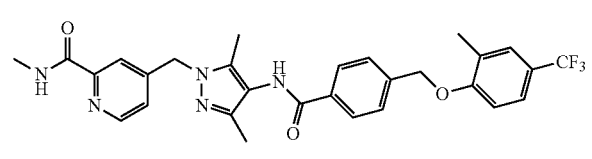
E3a
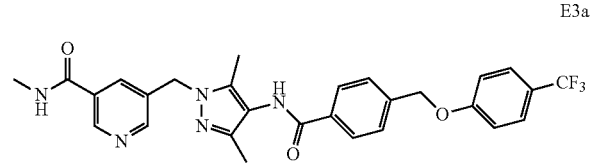
E3b
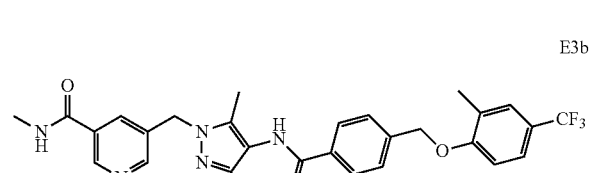
E4a
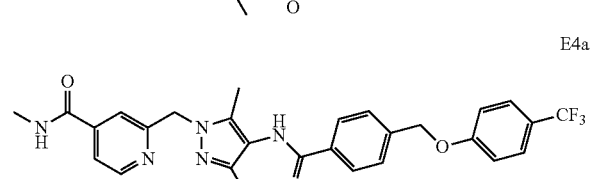
E4b
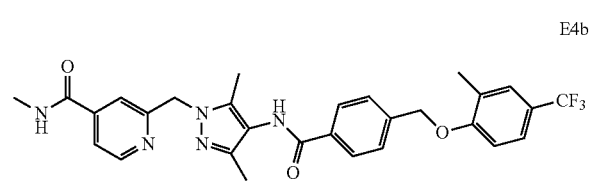
E5a
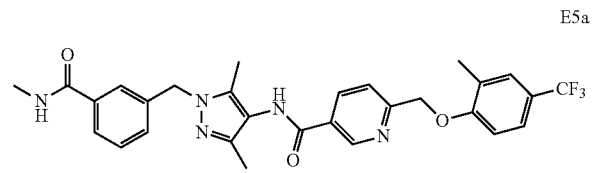
E5b
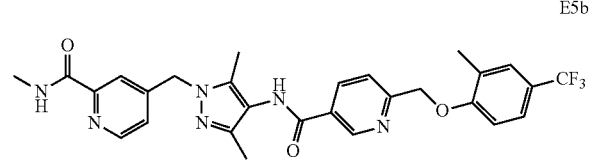
E6a
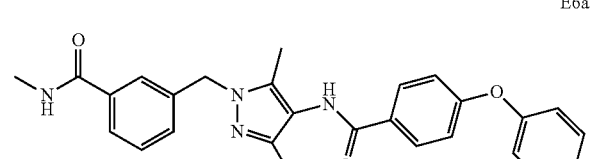
E6b
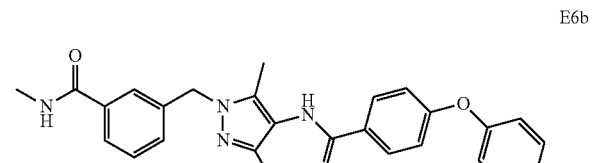

-continued

E6c
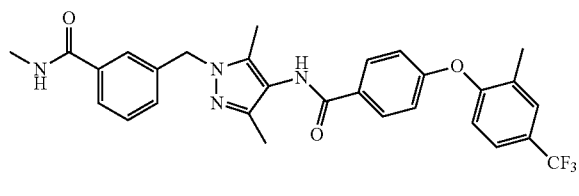

E7a
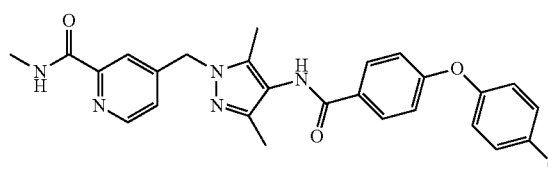

E7b
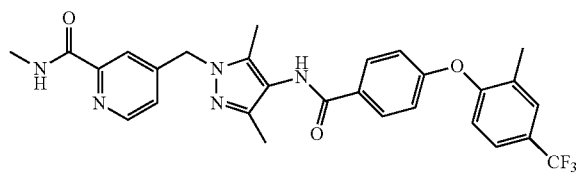

F1
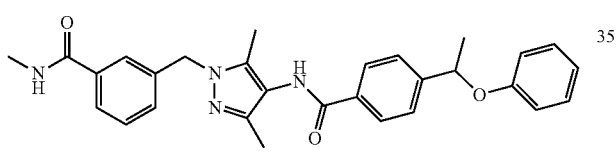

F2
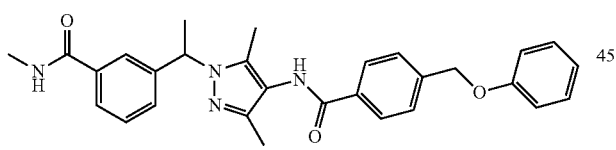

F3
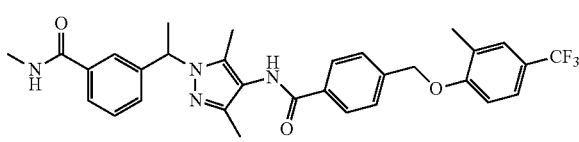

F4
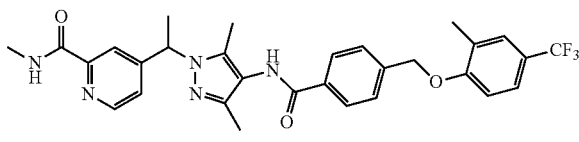

-continued

G1
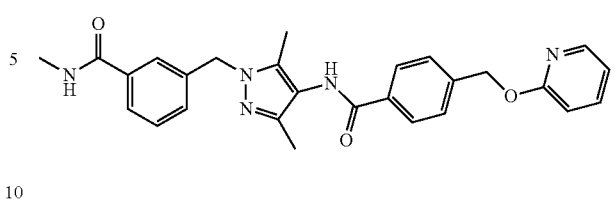

G2
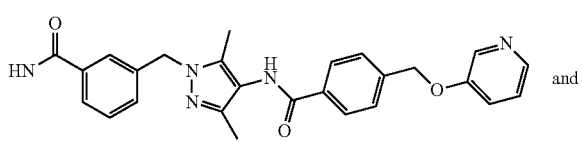 and

G3
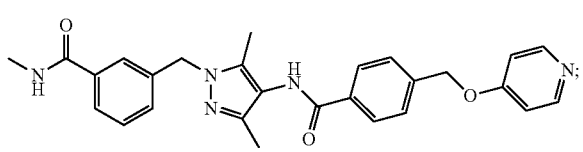

or a pharmaceutically acceptable salt thereof.

In one embodiment, the cancer is selected from pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.

In one embodiment, the cancer is pancreatic cancer.

The invention also provides a method for inhibiting cancer cell growth in an animal comprising administering an inhibitory effective amount of a compound of formula I or a pharmaceutically acceptable salt thereof, to the animal.

The invention also provides a compound of formula I or a pharmaceutically acceptable salt thereof for use in the prophylactic or therapeutic inhibition of cancer cell growth.

The invention also provides the use of a compound of formula I or a pharmaceutically acceptable salt thereof for the manufacture of a medicament for the inhibition of cancer cell growth.

In one embodiment, the cancer cell is pancreatic cancer cell.

Processes and intermediates useful for preparing compounds of formula I are provided as further embodiments of the invention and are illustrated by the following procedures in which the meanings of the generic radicals are as given above unless otherwise qualified.

Compounds of formula I may be prepared by the process illustrated in Schemes 1-8.

Scheme 1. Synthetic route to compounds A1, A2a-A2c, A3a-A3c, and A4a-A4d: (a) Cs₂CO₃, DMF; (b) NaBH₄, NiCl₂·6H₂O; (c) 4-(phenoxymethyl)benzoic acid, EDC, DMF/CH₂Cl₂; (d) NaOH, MeOH, H₂O; (e) 7N methanolic NH₃, 70° C.; (f) MeNH₂, EtOH, 70° C.; (g) amine, HBTU, Et₃N, DMF/CH₂Cl₂.
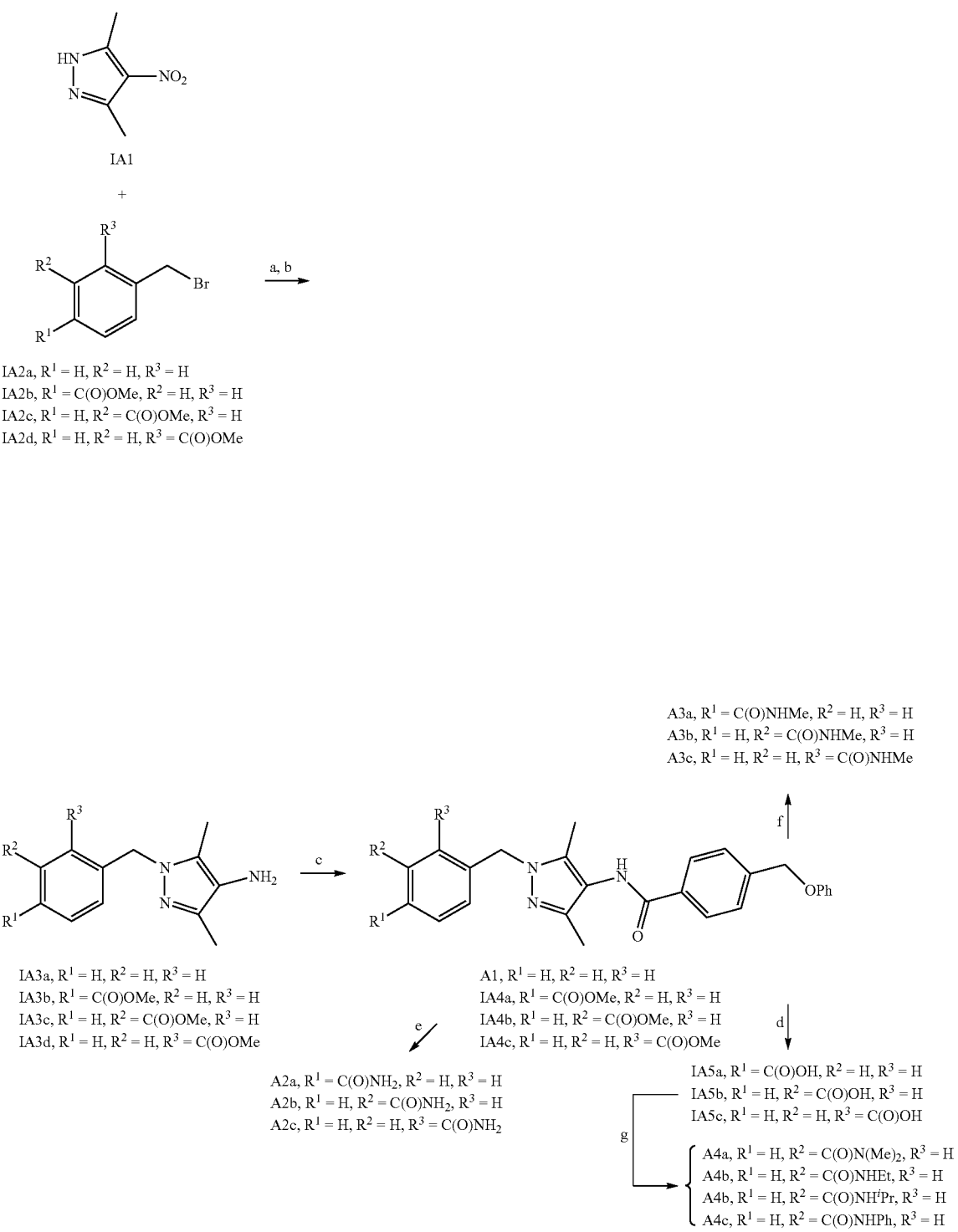

Scheme 2. Synthetic route to compounds A5a-A5c, A6a-A6c, and A7a-A7c:

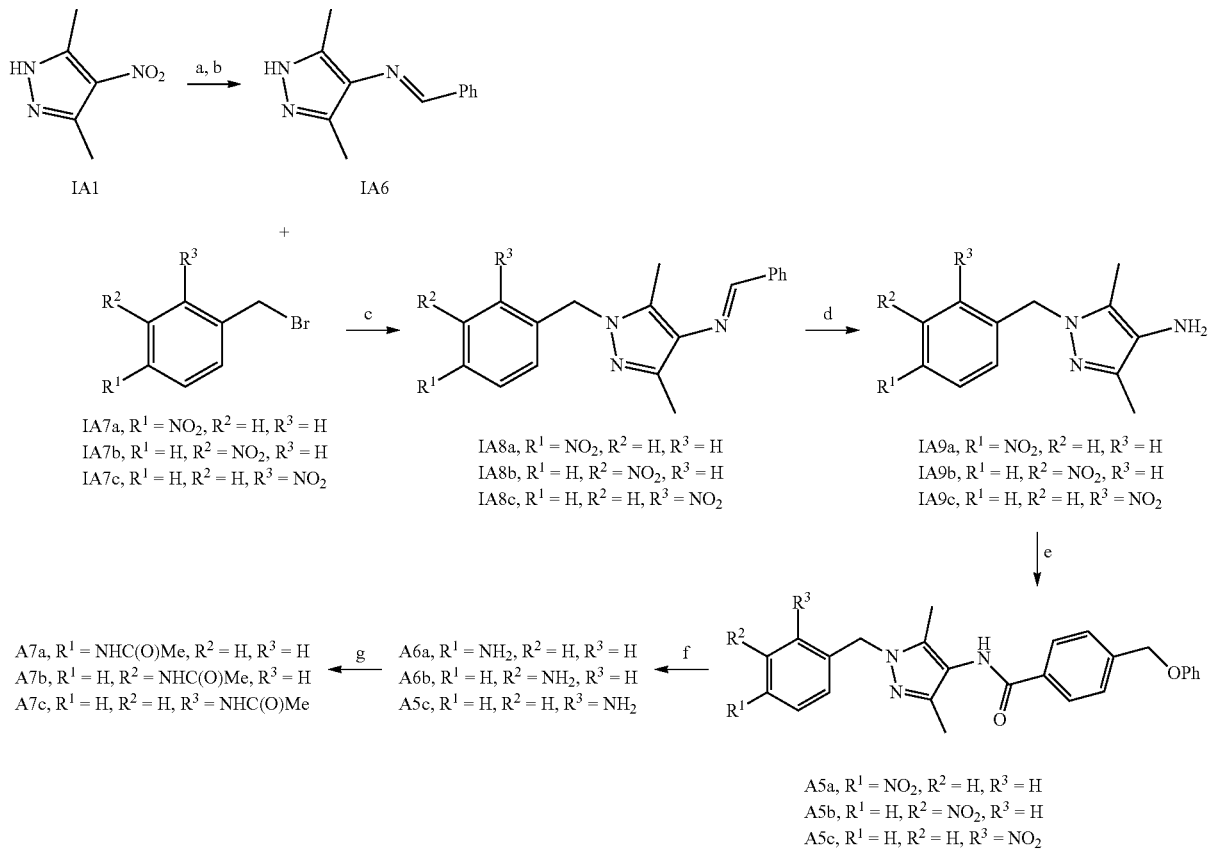

(a) H₂, Pd/C, MeOH; (b) benzaldehyde, reflux; (c) KO'Bu, DMF; (d) 1N HCl, MeOH; (e) 4-(phenoxymethyl)benzoic acid, EDC, DMF/CH₂Cl₂; (f) NaHB₄, NiCl₂·6H₂O, MeOH; (g) Ac₂O, Et₃N, CH₂Cl₂.

Scheme 3. Synthetic route to compounds B1-B3: (a) MeI, LDA, THF, 0° C.; (b) MeNH₂, EtOH, 80° C.; (c) IA2c, Cs₂CO₃, DMF; (d) MeNH₂, EtOH, 70° C.; (e) NaBH₄, NiCl₂·6H₂O, MeOH; (f) 4-(phenoxymethyl)benzaldehyde, CH₂Cl₂; then NaBH₄, MeOH, 0° C.; (g) 4-(phenoxymethyl)benzenesulfonyl chloride, Et₃N, THF.

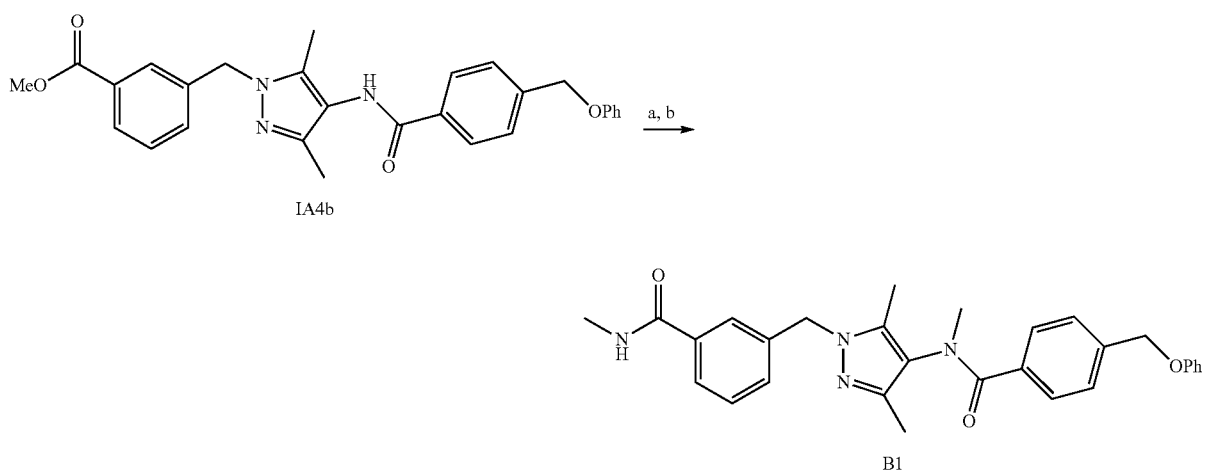

23                                                                              24
-continued
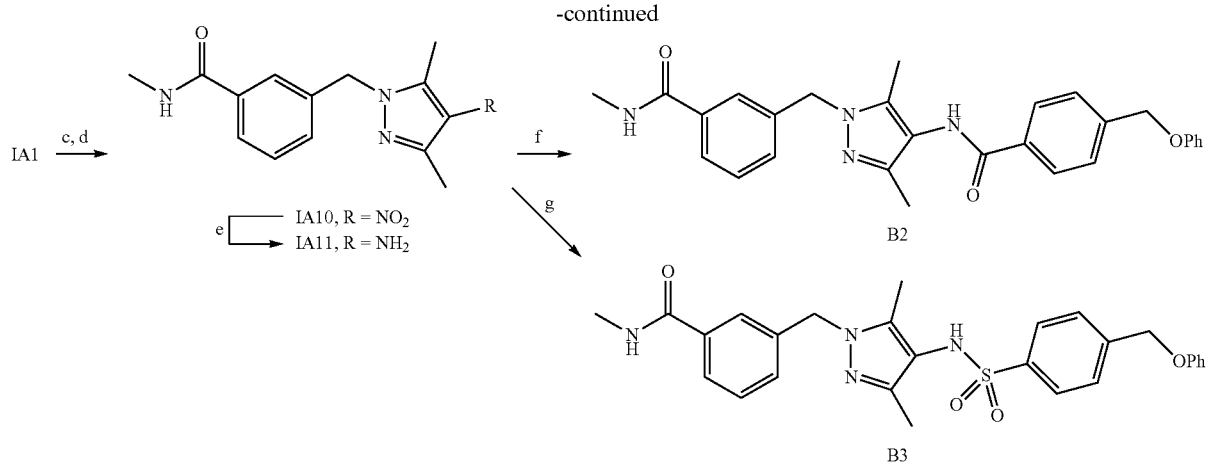
Scheme 4: Synthetic route to compounds C1-C7:
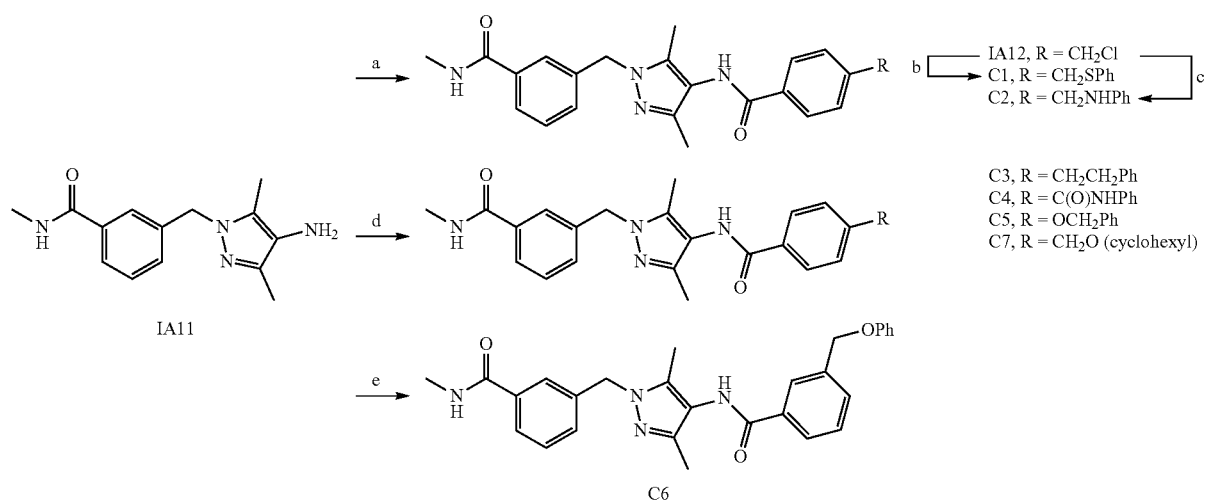
C3, R = CH$_2$CH$_2$Ph
C4, R = C(O)NHPh
C5, R = OCH$_2$Ph
C7, R = CH$_2$O (cyclohexyl)
(a) 4-(chloromethyl)benzoyl chloride, Et$_3$N, CH$_2$Cl$_2$; (b) thiophenol, Cs$_2$CO$_3$, DMF, 50° C.; (c) aniline, DIPEA, DMF, 80° C.; (d) carboxylic acid, EDC or HBTU; (e) 3-(phenoxymethyl)benzoic acid, EDC.
Scheme 5. Synthetic route to compounds D1-D12 and G1-G3:
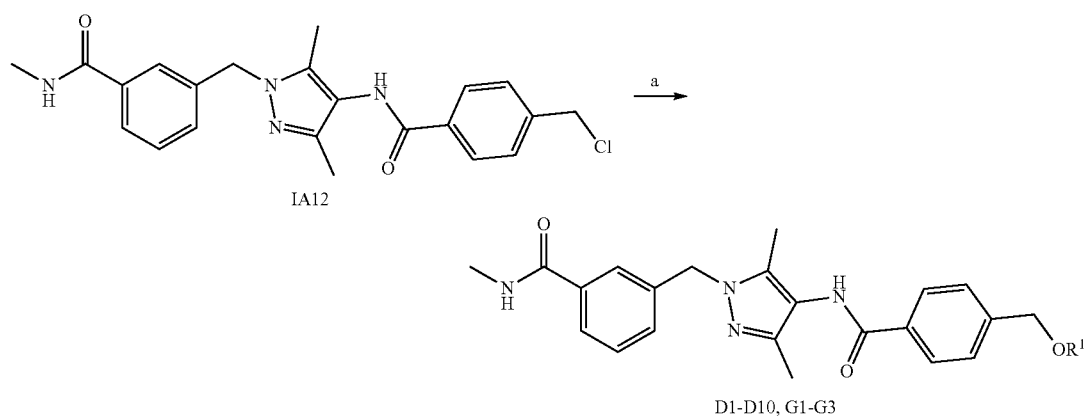

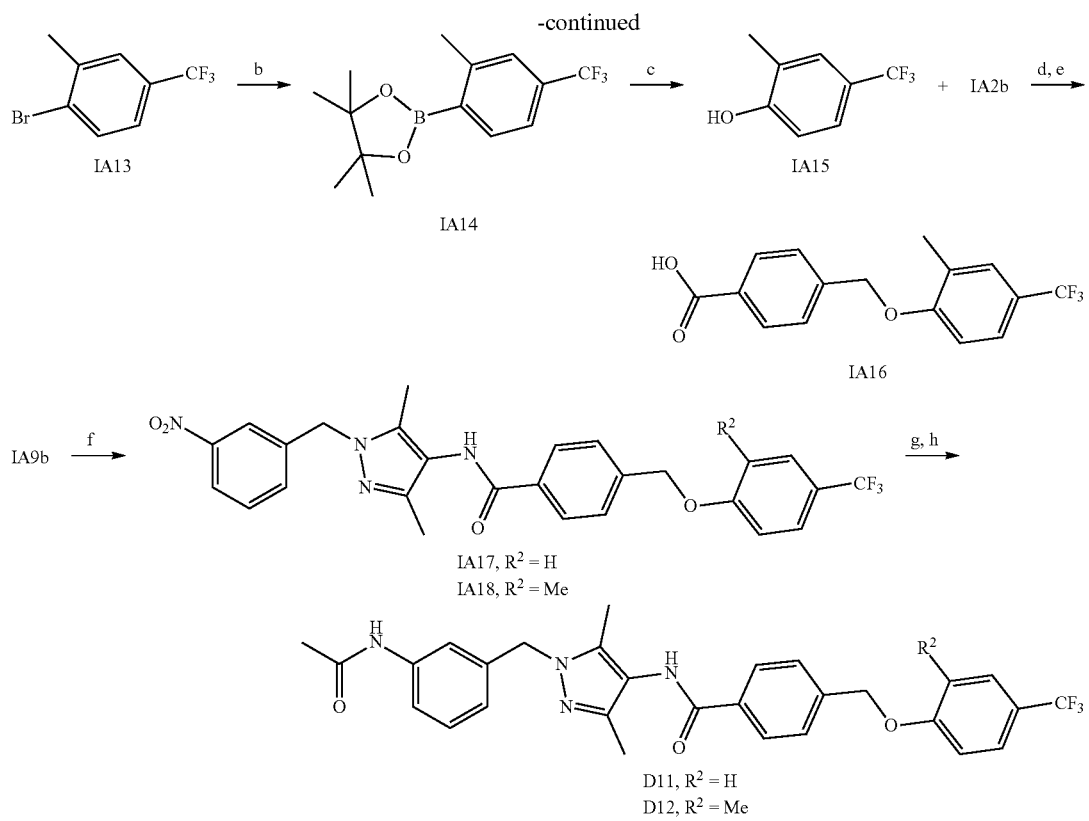
(a) ArOH, Cs₂CO₃, DMF, 50° C.; (b) bis(pinacolato)diboron, Pd(dppf)Cl₂, KOAc, DMSO, 80° C.; (c) mCPBA, EtOH, H₂O; (d) Cs₂CO₃, DMF, 80° C.; (e) NaOH, MeOH, H₂O; (f) carboxylic acid, EDC; (g) NaBH₄, NiCl₂•6H₂O, MeOH; (h) Ac₂O, Et₃N, CH₂Cl₂.
Scheme 6. Synthetic route to compounds E1a, E1b, E2a, E2b, E3a, E3b, E4a and E4b:
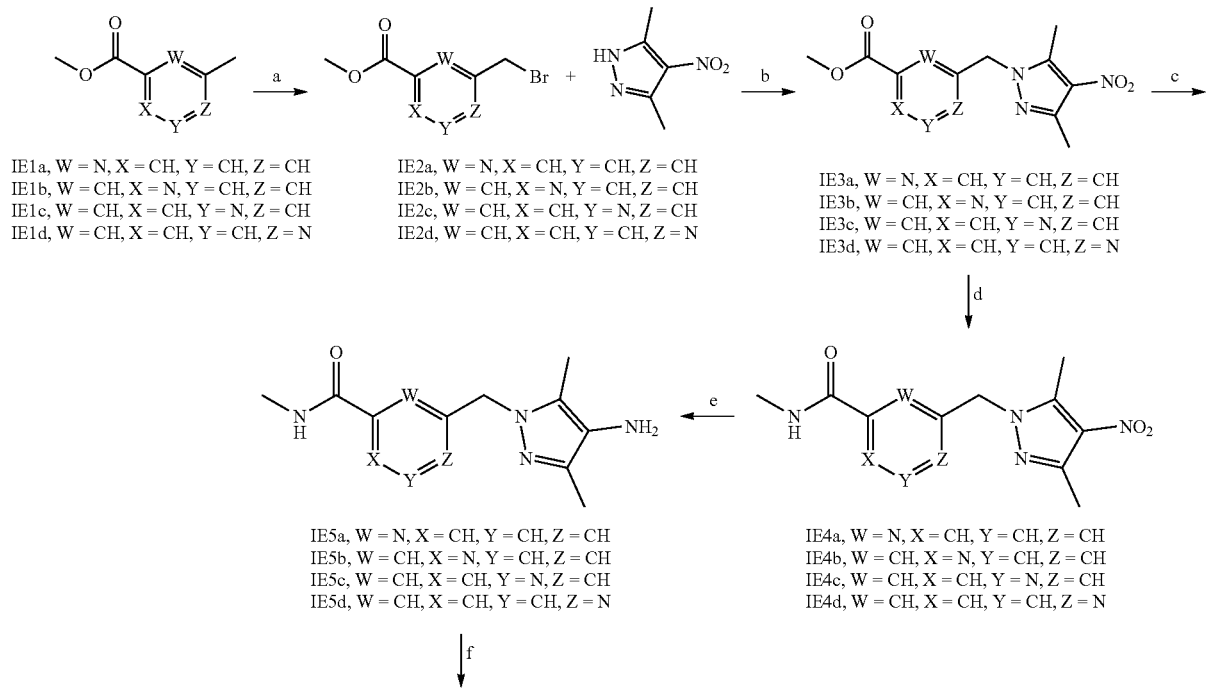

-continued

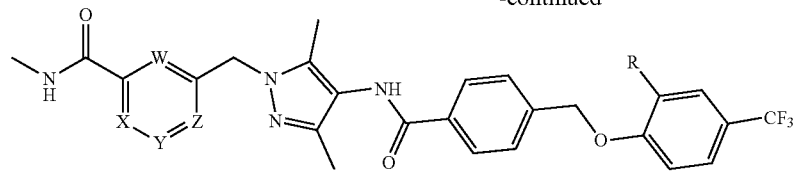

E1a, W = N, X = CH, Y = CH, Z = CH, R = H
E1b, W = N, X = CH, Y = CH, Z = CH, R = Me
E2a, W = CH, X = N, Y = CH, Z = CH, R = H
E2b, W = CH, X = N, Y = CH, Z = CH, R = Me
E3a, W = CH, X = CH, Y = N, Z = CH, R = H
E3b, W = CH, X = CH, Y = N, Z = CH, R = Me
E4a, W = CH, X = CH, Y = CH, Z = N, R = H
E4b, W = CH, X = CH, Y = CH, Z = N, R = Me (a) NBS, AIBN, CCl$_4$, 70° C.; (b) KOtBu, DMF; (c) MeNH$_2$, EtOH, 70° C.; (d) NaBH$_4$, NiCl$_2$•6H$_2$O, MeOH; (e) EDC, carboxylic acid.

Scheme 7. Synthetic route to compounds E5a, E5b, E6a-E6c, E7a, and E7b: (a) NBS, AIBN, CCl$_4$, 70° C.; (b) Cs$_2$CO$_3$, DMF; (c) DMF; (c) NaOH, MeOH/H$_2$O; (d) CuI, picolinic acid, K$_3$PO$_4$, DMSO, 90° C.; (e) NaOH, MeOH/H$_2$O; (f) EDC, IE9; (g) EDC, carboxylic acid.

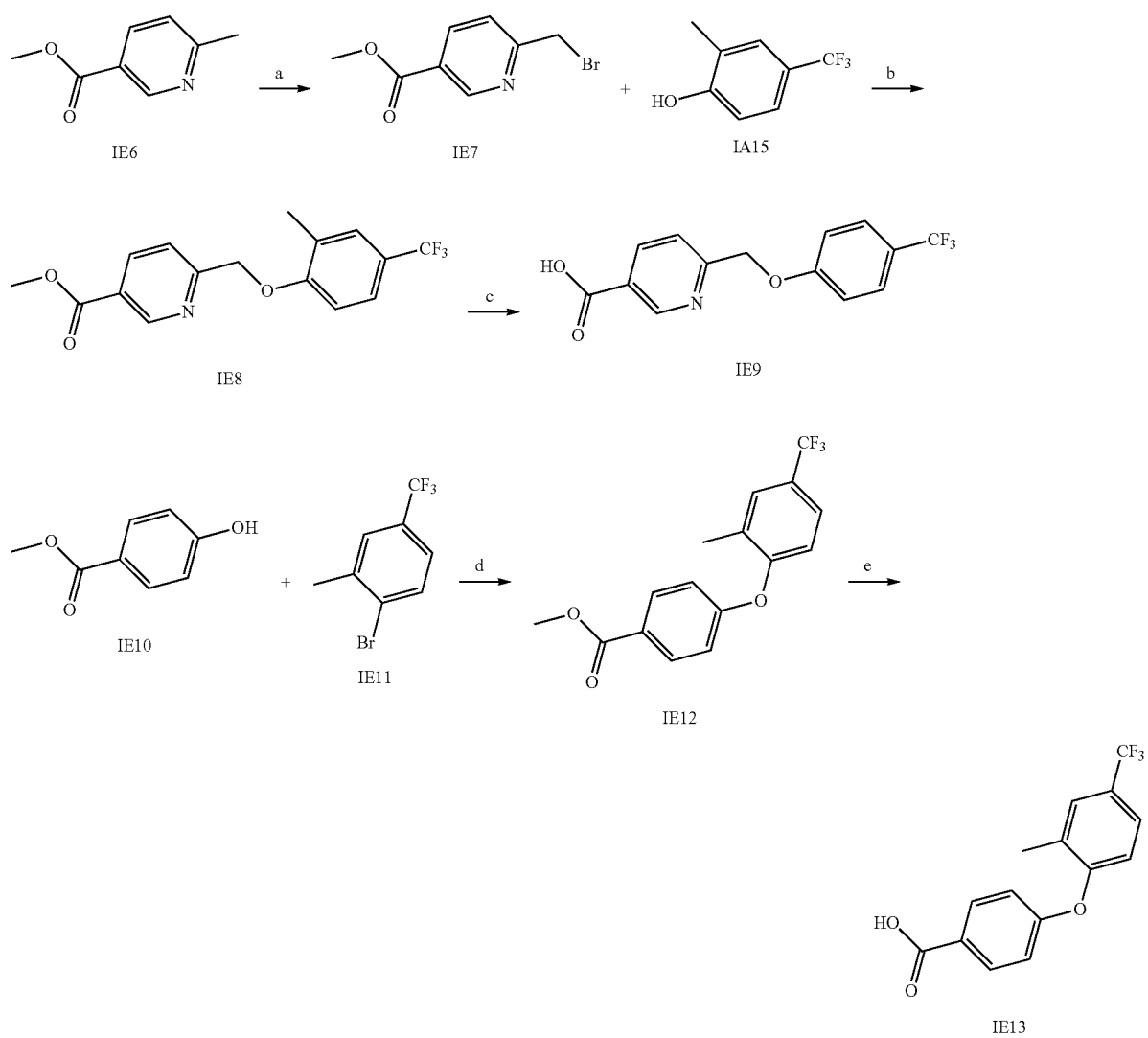

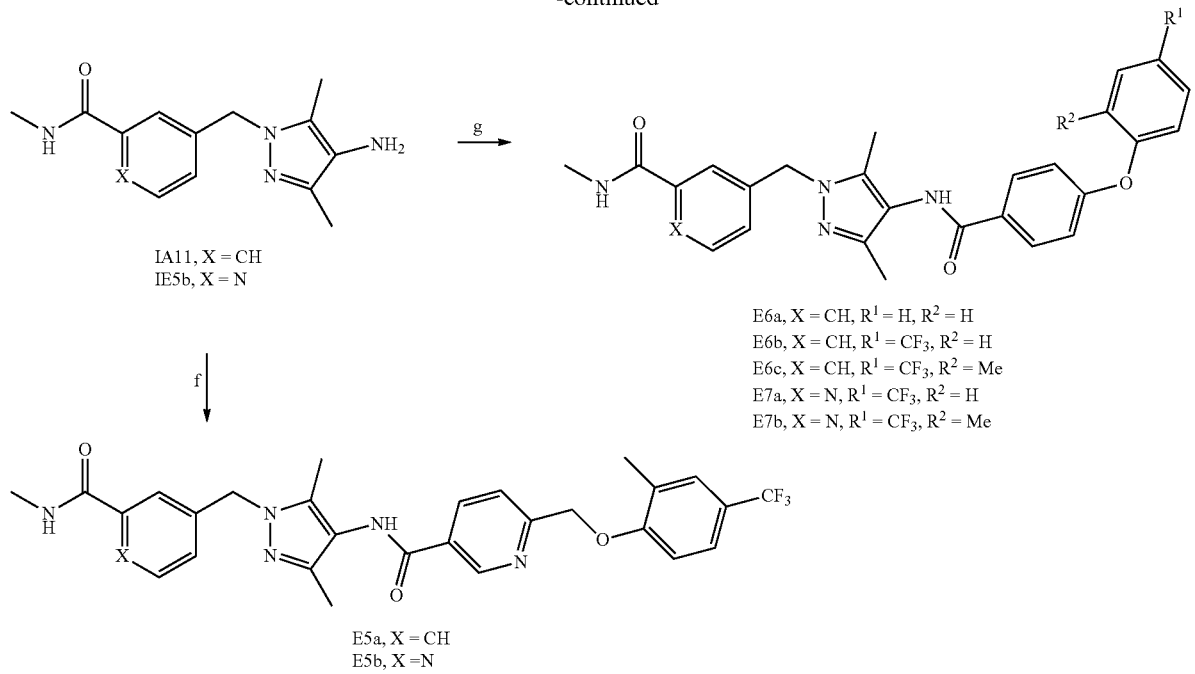

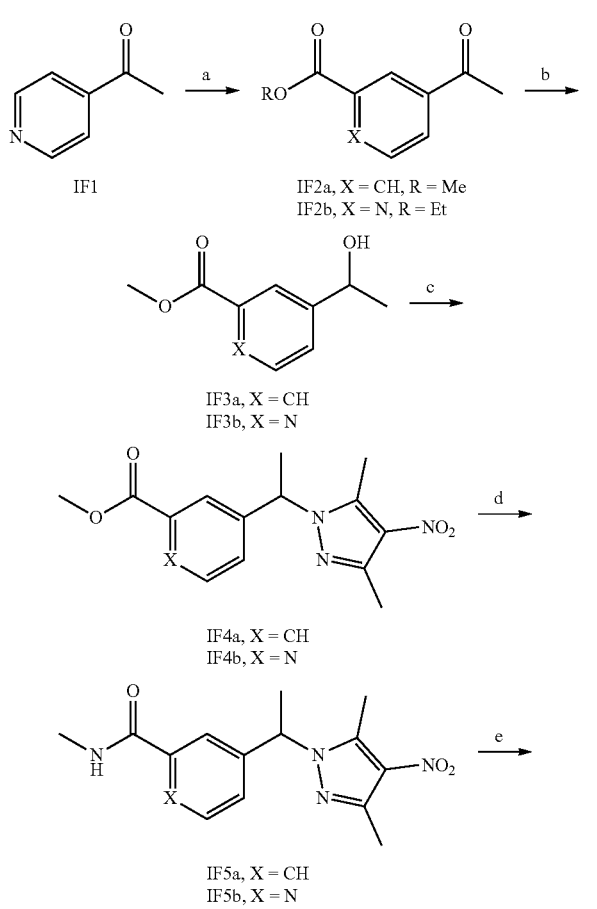

Scheme 8. Synthetic route to compounds F-F4:

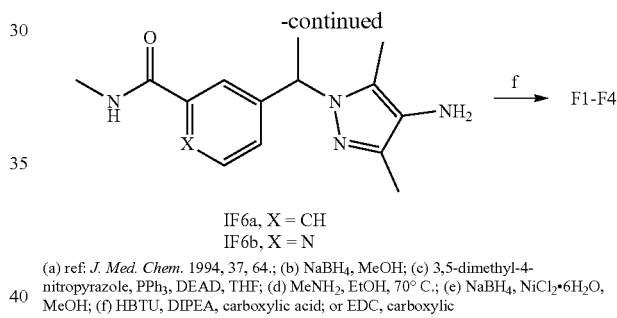

(a) ref: *J. Med. Chem.* 1994, 37, 64.; (b) NaBH$_4$, MeOH; (c) 3,5-dimethyl-4-nitropyrazole, PPh$_3$, DEAD, THF; (d) MeNH$_2$, EtOH, 70° C.; (e) NaBH$_4$, NiCl$_2$•6H$_2$O, MeOH; (f) HBTU, DIPEA, carboxylic acid; or EDC, carboxylic In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1

Synthesis of N-(1-Benzyl-3,5-dimethyl-1H-pyrazol-4-yl)-4-(phenoxymethyl)benzamide (A1)

Step 1. Synthesis of 1-Benzyl-3,5-dimethyl-1H-pyrazol-4-amine (IA3a)

To a solution of 3,5-dimethyl-4-nitropyrazole (IA1, 1.41 g, 10 mmol) in DMF (30 mL) were added benzyl bromide (IA2a, 2.05 g, 12 mmol) and $Cs_2CO_3$ (6.52 g, 20 mmol) and the mixture was allowed to stir at rt for 24 h. The reaction was quenched with water (50 mL) and the mixture was extracted with EtOAc. The organic phase was washed with water and brine, dried over anhydrous $Na_2SO_4$, and concentrated in vacuo. After purification by flash column chromatography (0-50% EtOAc/hexanes), 1-benzyl-3,5-dimethyl-4-nitro-1H-pyrazole was obtained as a white solid (1.39 g, 60%). $^1$H NMR (CDCl$_3$, 600 MHz) δ 7.37-7.28 (m, 3H), 7.16-7.12 (m, 2H), 5.26 (s, 2H), 2.56 (s, 3H), 2.55 (s, 3H). HRMS (ESI$^+$) calcd for $C_{12}H_{14}N_3O_2$ (M+H)$^+$ 232.1081, found 232.1079.

This nitro compound (1.39 g, 6.0 mmol) and $NiCl_2 \cdot 6H_2O$ (2.85 g, 12 mmol) were then dissolved in MeOH (70 mL). $NaBH_4$ (907 mg, 24 mmol) was slowly added to the above solution and the mixture was allowed to stir at rt for 3 h. The reaction was quenched with saturated $NH_4Cl$ (50 mL) and the mixture was extracted with EtOAc. The organic phase was washed with water and brine, dried over anhydrous $K_2CO_3$, and concentrated in vacuo. The residue was purified by flash column chromatography (0-60% EtOAc/hexanes) to afford compound IA3a as a brown oil (1.00 g, 50% over two steps). $^1$H NMR (CDCl$_3$, 600 MHz) δ 7.32-7.25 (m, 2H), 7.24-7.20 (m, 1H), 7.07-7.03 (m, 2H), 5.16 (s, 2H), 2.20 (s, 3H), 2.04 (s, 3H). HRMS (ESI$^+$) $C_{12}H_{16}N_3$ (M+H)$^+$ 202.1339, found 202.1342.

Step 2. Synthesis of N-(1-Benzyl-3,5-dimethyl-1H-pyrazol-4-yl)-4-(phenoxymethyl)benzamide (A1)

To a solution of 4-(phenoxymethyl)-benzoic acid (55 mg, 0.24 mmol) and EDC (46 mg, 0.24 mmol) in DMF/CH$_2$Cl$_2$ (1:1, 10 mL) was added amine IA3a (40 mg, 0.20 mmol) and the mixture was allowed to stir at rt for 12 h. After the solvents were removed, the residue was diluted with EtOAc (30 mL), H$_2$O (10 mL) and saturated NaHCO$_3$ (10 mL). After separation, the organic layer was washed with brine (20 mL) and concentrated. The residue was purified by flash column chromatography (0-10% MeOH/CH$_2$Cl$_2$) to give compound A1 as a white solid (85 mg, 90%). $^1$H NMR (CDCl$_3$, 600 MHz) δ 7.90 (d, J=8.4 Hz, 2H), 7.55 (d, J=7.2 Hz, 2H), 7.33-7.27 (m, 4H), 7.27-7.21 (m, 2H), 7.12 (d, J=7.8 Hz, 2H), 7.00-6.95 (m, 3H), 5.23 (s, 2H), 5.15 (s, 2H), 2.21 (s, 3H), 2.10 (s, 3H). HRMS (ESI$^+$) $C_{26}H_{26}N_3O_2$ (M+H)$^+$ 412.2020, found 412.2022.

Example 2

Synthesis of N-(1-(4-Carbamoylbenzyl)-3,5-dimethyl-1H-pyrazol-4-yl)-4-(phenoxymethyl)benzamide (A2a)

Step 1. Synthesis of Methyl 4-((4-Amino-3,5-dimethyl-1H-pyrazol-1-yl)methyl)benzoate (IA3b)

Intermediate IA3b was prepared with bromide IA2b, in a fashion similar to the one described for intermediate IA3a. Brown oil, 788 mg, 91% yield. $^1$H NMR (CDCl$_3$, 600 MHz) δ 7.96 (d, J=7.8 Hz, 2H), 7.08 (d, J=7.8 Hz, 2H), 5.21 (s, 2H), 3.9 (s, 3H), 2.20 (s, 3H), 2.03 (s, 3H). HRMS (ESI$^+$) calcd for $C_{14}H_{18}N_3O_2$ (M+H)$^+$ 260.1394, found 260.1395.

Step 2. Synthesis of Methyl 4-((3,5-Dimethyl-4-(4-(phenoxymethyl)benzamido)-1H-pyrazol-1-yl)methyl)benzoate (IA4a)

Compound IA4a was prepared from IA3b, via an EDC-mediated amide formation in a fashion similar to the one described for compound A1. White solid, 300 mg, 64% yield. $^1$H NMR (DMSO-d$_6$, 600 MHz) δ 9.56 (s, 1H), 7.97 (d, J=8.4 Hz, 2H), 7.88 (d, J=7.8 Hz, 1H), 7.83 (s, 1H), 7.56 (d, J=7.8 Hz, 2H), 7.51 (dd, J=7.5, 7.5 Hz, 1H), 7.42 (d, J=8.4 Hz, 1H), 7.30 (dd, J=7.8, 7.8 Hz, 2H), 7.02 (d, J=7.8 Hz, 2H), 6.95 (dd, J=7.5, 7.5 Hz, 1H), 5.32 (s, 2H), 5.20 (s, 2H), 3.85 (s, 3H), 2.07 (s, 3H), 2.04 (s, 3H). HRMS (ESI$^+$) calcd for $C_{28}H_{28}N_3O_4$ (M+H)$^+$ 470.2080, found 470.2083.

Step 3. Synthesis of N-(1-(4-Carbamoylbenzyl)-3,5-dimethyl-1H-pyrazol-4-yl)-4-(phenoxymethyl)benzamide (A2a)

A solution of methyl ester IA4a (47 mg, 0.10 mmol) in NH$_3$/MeOH (~7 N, 5 mL) in a sealed tube was heated at 70° C. for 16 h. After the solvent was evaporated in vacuo, the residue was purified by flash column chromatography (0-20% MeOH/CH$_2$Cl$_2$) to afford compound A2a as a white solid (14 mg, 31%). $^1$H NMR (DMSO-d$_6$, 600 MHz) δ 9.55 (s, 1H), 7.97 (d, J=7.8 Hz, 2H), 7.92 (s, 1H), 7.83 (d, J=8.4 Hz, 2H), 7.56 (d, J=8.4 Hz, 2H), 7.34 (s, 1H), 7.30 (dd, J=7.8, 7.8 Hz, 2H), 7.18 (d, J=7.8 Hz, 2H), 7.02 (d, J=7.8 Hz, 2H), 6.95 (dd, J=7.5, 7.5 Hz, 1H), 5.29 (s, 2H), 5.20 (s, 2H), 2.06 (s, 3H), 2.04 (s, 3H). HRMS (ESI$^+$) calcd for $C_{27}H_{27}N_4O_3$ (M+H)$^+$ 455.2083, found 455.2087.

Example 3

Synthesis of N-(1-(3-Carbamoylbenzyl)-3,5-dimethyl-1H-pyrazol-4-yl)-4-(phenoxymethyl)benzamide (A2b)

Step 1. Synthesis of Methyl 3-((4-Amino-3,5-dimethyl-1H-pyrazol-1-yl)methyl)benzoate (IA3c)

Intermediate IA3c was prepared with bromide IA2c, in a fashion similar to the one described for intermediate IA3a. Brown oil, 683 mg, 81% yield. $^1$H NMR (CDCl$_3$, 600 MHz) δ 7.92 (d, J=7.8 Hz, 1H), 7.80 (s, 1H), 7.36 (dd, J=7.8, 7.8 Hz, 1H), 7.19 (d, J=7.2 Hz, 1H), 5.20 (s, 2H), 3.90 (s, 3H), 2.20 (s, 3H), 2.05 (s, 3H). HRMS (ESI$^+$) calcd for $C_{14}H_{18}N_3O_2$ (M+H)$^+$ 260.1394, found 260.1394.

Step 2. Synthesis of Methyl 3-((3,5-Dimethyl-4-(4-(phenoxymethyl)benzamido)-1H-pyrazol-1-yl)methyl)benzoate (IA4b)

Compound IA4b was prepared from IA3c, via an EDC-mediated amide formation in a fashion similar to the one described for compound A1. White solid, 200 mg, 40% yield. $^1$H NMR (CDCl$_3$, 600 MHz) δ 7.94 (d, J=8.4 Hz, 1H), 7.91 (d, J=8.4 Hz, 2H), 7.86 (s, 1H), 7.56 (d, J=8.4 Hz, 2H), 7.40 (dd, J=7.5, 7.5 Hz, 1H), 7.32-7.28 (m, 3H), 7.24-7.20 (m, 1H), 7.00-6.95 (m, 3H), 5.27 (s, 2H), 5.15 (s, 2H), 3.91

(s, 3H), 2.21 (s, 3H), 2.12 (s, 3H). HRMS (ESI$^+$) calcd for C$_{28}$H$_{28}$N$_3$O$_4$ (M+H)$^+$ 470.2080, found 470.2075.

Step 3. Synthesis N-(1-(3-Carbamoylbenzyl)-3,5-dimethyl-1H-pyrazol-4-yl)-4-phenoxymethyl)benzamide (A2b)

Compound A2b was prepared from IA4b, in a fashion similar to the one described for compound A2a. White solid, 23 mg, 50% yield. $^1$H NMR (DMSO-d$_6$, 600 MHz) δ 9.56 (s, 1H), 8.01-7.94 (m, 3H), 7.77 (d, J=7.8 Hz, 1H), 7.73 (s, 1H), 7.56 (d, J=8.4 Hz, 2H), 7.42 (dd, J=7.5, 7.5 Hz, 1H), 7.38 (s, 1H), 7.30 (dd, J=7.5, 7.5 Hz, 2H), 7.26 (d, J=7.8 Hz, 1H), 7.02 (d, J=7.8 Hz, 2H), 6.95 (dd, J=7.5, 7.5 Hz, 1H), 5.27 (s, 2H), 5.20 (s, 2H), 2.08 (s, 3H), 2.04 (s, 3H). HRMS (ESI$^+$) calcd for C$_{27}$H$_{27}$N$_4$O$_3$ (M+H)$^+$ 455.2083, found 455.2082.

Example 4

Synthesis of N-(1-(2-Carbamoylbenzyl)-3,5-dimethyl-1H-pyrazol-4-yl)-4-(phenoxymethyl)benzamide (A2c)

Step 1. Synthesis of Methyl 2-((4-Amino-3,5-dimethyl-1H-pyrazol-1-yl)methyl)benzoate (IA3d)

Compound IA3d was prepared with bromide IA2d, in a fashion similar to the one described for intermediate IA3a. Brown oil, 776 mg, 89% yield. $^1$H NMR (CDCl$_3$, 600 MHz) δ 8.00 (d, J=8.4 Hz, 1H), 7.38 (dd, J=7.2, 7.2 Hz, 1H), 7.29 (dd, J=7.8, 7.8 Hz, 1H), 7.78 (d, J=7.8 Hz, 1H), 5.61 (s, 2H), 3.93 (s, 3H), 2.22 (s, 3H), 2.03 (s, 3H). HRMS (ESI$^+$) calcd for C$_{14}$H$_{18}$N$_3$O$_2$ (M+H)$^+$ 260.1394, found 260.1396.

Step 2. Synthesis of Methyl 2-((3,5-Dimethyl-4-(4-(phenoxymethyl)benzamido)-1H-pyrazol-1-yl)methyl)benzoate (IA4c)

Compound IA4c was prepared from IA3d, in a fashion similar to the one described for compound A1. White solid, 776 mg, 89% yield. $^1$H NMR (DMSO-d$_6$, 600 MHz) δ 9.61 (s, 1H), 7.99 (d, J=7.8 Hz, 2H), 7.93 (d, J=7.2 Hz, 1H), 7.60-7.52 (m, 3H), 7.42 (dd, J=7.2, 7.2 Hz, 1H), 7.30 (dd, J=7.8, 7.8 Hz, 2H), 7.02 (d, J=7.8 Hz, 2H), 6.95 (dd, J=7.5, 7.5 Hz, 1H), 6.55 (d, J=7.2 Hz, 1H), 5.58 (s, 2H), 5.20 (s, 2H), 3.89 (s, 3H), 2.05 (s, 3H), 2.02 (s, 3H). HRMS (ESI$^+$) calcd for C$_{28}$H$_{28}$N$_3$O$_4$ (M+H)$^+$ 470.2080, found 470.2081.

Step 3. Synthesis of N-(1-(2-Carbamoylbenzyl)-3,5-dimethyl-1H-pyrazol-4-yl)-4-(phenoxymethyl)benzamide (A2c)

Compound A2c was prepared from IA4c, in a fashion similar to the one described for compound A2a. White solid, 13 mg, 29% yield. $^1$H NMR (DMSO-d$_6$, 600 MHz) δ 9.58 (s, 1H), 8.04 (s, 1H), 7.98 (d, J=7.8 Hz, 2H), 7.57 (d, J=7.8 Hz, 2H), 7.55-7.50 (m, 2H), 7.38 (dd, J=7.5, 7.5 Hz, 1H), 7.35-7.27 (m, 3H), 7.02 (d, J=7.8 Hz, 2H), 6.95 (dd, J=7.5, 7.5 Hz, 1H), 6.68 (d, J=7.8 Hz, 1H), 5.41 (s, 2H), 5.20 (s, 2H), 2.04 (s, 3H), 2.04 (s, 3H). HRMS (ESI$^+$) calcd for C$_{27}$H$_{27}$N$_4$O$_3$ (M+H)$^+$ 455.2083, found 455.2081.

Example 5

Synthesis of N-(3,5-Dimethyl-1-(4-(methylcarbamoyl)benzyl)-1H-pyrazol-4-yl)-4-(phenoxymethyl)benzamide (A3a)

A solution of methyl ester IA4a (47 mg, 0.10 mmol) in MeNH$_2$/EtOH (33 wt. %, 7 mL) in a sealed tube was heated at 70° C. for 24 h. After the solvent was evaporated in vacuo, the residue was purified by flash column chromatography (0-20% MeOH/CH$_2$Cl$_2$) to afford compound A3a as a white solid (32 mg, 68%). $^1$H NMR (DMSO-d$_6$, 600 MHz) δ 9.55 (s, 1H), 8.41-8.35 (m, 1H), 7.97 (d, J=8.4 Hz, 2H), 7.78 (d, J=8.4 Hz, 2H), 7.56 (d, J=7.8 Hz, 2H), 7.30 (dd, J=7.8, 7.8 Hz, 2H), 7.20 (d, J=7.8 Hz, 2H), 7.02 (d, J=7.8 Hz, 2H), 6.95 (dd, J=7.5, 7.5 Hz, 1H), 5.29 (s, 2H), 5.20 (s, 2H), 2.77 (d, J=4.8 Hz, 3H), 2.06 (s, 3H), 2.04 (s, 3H). HRMS (ESI$^+$) calcd for C$_{28}$H$_{29}$N$_4$O$_3$(M+H)$^+$ 469.2240, found 469.2241.

Example 6

Synthesis of 3-((3,5-Dimethyl-4-(4-(phenoxymethyl)benzamido)-1H-pyrazol-1-yl)methyl)-N-methylbenzamide (A3b)

Compound A3b was prepared from IA4b, in a fashion similar to the one described for compound A3a. White solid, 30 mg, 64% yield. $^1$H NMR (DMSO-d$_6$, 600 MHz) δ 9.56 (s, 1H), 8.47-8.40 (m, 1H), 7.97 (d, J=7.8 Hz, 2H), 7.72 (d, J=7.8 Hz, 1H), 7.69 (s, 1H), 7.56 (d, J=7.8 Hz, 2H), 7.43 (dd, J=7.4, 7.4 Hz, 1H), 7.33-7.24 (m, 3H), 7.02 (d, J=7.8 Hz, 2H), 6.95 (dd, J=7.5, 7.5 Hz, 1H), 5.28 (s, 2H), 5.20 (s, 2H), 2.78 (d, J=4.8 Hz, 3H), 2.07 (s, 3H), 2.04 (s, 3H). HRMS (ESI$^+$) calcd for C$_{28}$H$_{29}$N$_4$O$_3$(M+H)$^+$ 469.2240, found 469.2240.

Example 7

Synthesis of 2-((3,5-Dimethyl-4-(4-(phenoxymethyl)benzamido)-1H-pyrazol-1-yl)methyl)-N-methylbenzamide (A3c)

Compound A3c was prepared from IA4c, in a fashion similar to the one described for compound A3a. White solid, 13 mg, 28% yield. $^1$H NMR (DMSO-d$_6$, 600 MHz) δ 9.57 (s, 1H), 8.50-8.44 (m, 1H), 7.98 (d, J=7.8 Hz, 2H), 7.57 (d, J=7.8 Hz, 2H), 7.46 (d, J=7.2 Hz, 1H), 7.39 (dd, J=7.5, 7.5 Hz, 1H), 7.36-7.26 (m, 3H), 7.02 (d, J=7.8 Hz, 2H), 6.95 (dd, J=7.5, 7.5 Hz, 1H), 6.73 (d, J=7.8 Hz, 1H), 5.37 (s, 2H), 5.20 (s, 2H), 2.80 (d, J=3.6 Hz, 3H), 2.03 (s, 6H). HRMS (ESI$^+$) calcd for C$_{28}$H$_{29}$N$_4$O$_3$ (M+H)$^+$ 469.2240, found 469.2237.

Example 8

Synthesis of 3-((3,5-Dimethyl-4-(4-(phenoxymethyl)benzamido)-1H-pyrazol-1-yl)methyl)-N,N-dimethylbenzamide (A4a)

Step 1. Synthesis of 4-((3,5-Dimethyl-4-(4-(phenoxymethyl)benzamido)-1H-pyrazol-1-yl)methyl)benzoic Acid (IA5a)

To a solution of methyl ester IA4a (40 mg, 0.086 mmol) in H$_2$O/MeOH (1:1, 20 mL) was added NaOH (7 mg, 0.17 mmol) and the mixture was allowed to stir at rt for 12 h. After the MeOH was evaporated in vacuo, the residue was acidified with 1N HCl to pH=2 and the mixture was extracted with EtOAc. The organic phase was washed with water and brine, dried over anhydrous $Na_2SO_4$, and concentrated in vacuo to afford compound IA5a as a white solid (19 mg, 49%). $^1$H NMR (DMSO-$d_6$, 600 MHz) δ 12.93 (s, 1H), 9.56 (s, 1H), 7.97 (d, J=8.4 Hz, 2H), 7.92 (d, J=7.8 Hz, 2H), 7.56 (d, J=7.8 Hz, 2H), 7.30 (dd, J=7.8, 7.8 Hz, 2H), 7.24 (d, J=8.4 Hz, 2H), 7.02 (d, J=7.8 Hz, 2H), 6.95 (dd, J=7.5, 7.5 Hz, 1H), 5.32 (s, 2H), 5.20 (s, 2H), 2.06 (s, 3H), 2.04 (s, 3H). HRMS (ESI$^+$) calcd for $C_{27}H_{26}N_3O_4$ (M+H)$^+$ 456.1923, found 456.1924.

Step 2. Synthesis of 3-((3,5-Dimethyl-4-(4-(phenoxymethyl)benzamido)-1H-pyrazol-1-yl)methyl) benzoic Acid (IA5b)

Compounds IA5b was prepared from IA4b, in a fashion similar to the one described for compound IA5a. White solid, 23 mg, 59% yield. $^1$H NMR (DMSO-$d_6$, 600 MHz) δ13.01 (s, 1H), 9.56 (s, 1H), 7.97 (d, J=8.4 Hz, 2H), 7.85 (d, J=7.8 Hz, 1H), 7.78 (s, 1H), 7.56 (d, J=8.4 Hz, 2H), 7.49 (dd, J=7.5, 7.5 Hz, 1H), 7.40 (d, J=8.4 Hz, 1H), 7.30 (dd, J=7.5, 7.5 Hz, 2H), 7.02 (d, J=7.8 Hz, 2H), 6.95 (dd, J=7.5, 7.5 Hz, 1H), 5.31 (s, 2H), 5.20 (s, 2H), 2.07 (s, 3H), 2.04 (s, 3H). HRMS (ESI$^+$) calcd for $C_{27}H_{26}N_3O_4$ (M+H)$^+$ 456.1923, found 456.1925.

Step 3. Synthesis of 2-((3,5-Dimethyl-4-(4-(phenoxymethyl)benzamido)-1H-pyrazol-1-yl)methyl) benzoic Acid (IA5c)

Compounds IA5c was prepared from IA4c, in a fashion similar to the one described for compound IA5a. White solid, 17 mg, 43% yield. $^1$H NMR (DMSO-$d_6$, 600 MHz) δ 9.61 (s, 1H), 7.99 (d, J=8.4 Hz, 2H), 7.94 (d, J=7.2 Hz, 1H), 7.57 (d, J=7.8 Hz, 2H), 7.50 (dd, J=8.8, 7.8 Hz, 1H), 7.39 (dd, J=7.5, 7.5 Hz, 1H), 7.30 (dd, J=7.8, 7.8 Hz, 2H), 7.02 (d, J=7.8 Hz, 2H), 6.95 (dd, J=7.5, 7.5 Hz, 1H), 6.49 (d, J=7.8 Hz, 1H), 5.60 (s, 2H), 5.20 (s, 2H), 2.05 (s, 3H), 2.02 (s, 3H). HRMS (ESI$^+$) calcd for $C_{27}H_{26}N_3O_4$ (M+H)$^+$ 456.1923, found 456.1920.

Step 4. Synthesis of 3-((3,5-Dimethyl-4-(4-(phenoxymethyl)benzamido)-1H-pyrazol-1-yl)methyl)-N,N-dimethylbenzamide (A4a)

To a solution of compound IA5b (40 mg, 0.088 mmol), HBTU (40 mg, 0.11 mmol) and $Et_3N$ (25 μL, 0.18 mmol) in DMF/$CH_2Cl_2$ (1:1, 10 mL) was added dimethylamine (0.24 μL, 0.26 mmol) and the mixture was allowed to stir at rt for 12 h. After the solvents were removed, the residue was diluted with EtOAc (30 mL) and $H_2O$ (10 mL). After separation, the organic layer was washed with brine (20 mL) and concentrated. The residue was purified by flash column chromatography (0-15% MeOH/$CH_2Cl_2$) to give compound A4a as a white solid (40 mg, 94%). $^1$H NMR (CDCl$_3$, 600 MHz) δ 7.92 (d, J 7.8 Hz, 2H), 7.67 (s, 1H), 7.51 (d, J 7.8 Hz, 2H), 7.34-7.25 (m, 4H), 7.15-7.11 (m, 2H), 7.00-6.95 (m, 3H), 5.21 (s, 2H), 5.13 (s, 2H), 3.06 (s, 3H), 2.92 (s, 3H), 2.16 (s, 3H), 2.04 (s, 3H). HRMS (ESI$^+$) calcd for $C_{29}H_{31}N_4O_3$(M+H)$^+$ 483.2396, found 483.2410.

Example 9

Synthesis of 3-((3,5-Dimethyl-4-(4-(phenoxymethyl)benzamido)-1H-pyrazol-1-yl)methyl)-N-ethylbenzamide (A4b)

Compounds A4b was prepared from compound IA5b via a HBTU-mediated amide formation in a fashion similar to the one described for compound A4a. White solid, 28% yield. $^1$H NMR (CDCl$_3$, 600 MHz) δ 7.93 (d, J=8.4 Hz, 2H), 7.68 (d, J=7.2 Hz, 1H), 7.55 (d, J=7.2 Hz, 2H), 7.52 (s, 1H), 7.36 (dd, J=7.5, 7.5 Hz, 1H), 7.32-7.28 (m, 2H), 7.27 (s, 1H), 7.24 (d, J=7.8 Hz, 1H), 7.00-6.95 (m, 3H), 6.55-6.50 (m, 1H), 5.24 (s, 2H), 5.15 (s, 2H), 3.50-3.43 (m, 2H), 2.18 (s, 3H), 2.05 (s, 3H), 1.22 (t, J=7.2 Hz, 3H). HRMS (ESI$^+$) calcd for $C_{29}H_{31}N_4O_3$(M+H)$^+$ 483.2396, found 483.2395.

Example 10

Synthesis of 3-((3,5-Dimethyl-4-(4-(phenoxymethyl)benzamido)-1H-pyrazol-1-yl)methyl)-N-isopropylbenzamide (A4c)

Compounds A4c was prepared from compound IA5b via a HBTU-mediated amide formation in a fashion similar to the one described for compound A4a. White solid, 93% yield. H NMR (CDCl$_3$, 600 MHz) δ 7.91 (d, J=7.8 Hz, 2H), 7.66 (d, J=7.8 Hz, 1H), 7.57 (d, J=8.4 Hz, 2H), 7.40-7.36 (m, 2H), 7.30 (dd, J=8.1, 8.1 Hz, 2H), 7.24-7.22 (m, 2H), 7.00-6.96 (m, 3H), 6.09-6.05 (m, 1H), 5.28 (s, 2H), 5.16 (s, 2H), 4.32-4.24 (m, 1H), 2.21 (s, 3H), 2.10 (s, 3H), 1.25 (d, J=6.6 Hz, 6H). HRMS (ESI$^+$) calcd for $C_{30}H_{33}N_4O_3$ (M+H)$^+$ 497.2553, found 497.2558.

Example 11

Synthesis of 3-((3,5-Dimethyl-4-(4-(phenoxymethyl)benzamido)-1H-pyrazol-1-yl)methyl)-N-phenylbenzamide (A4d)

Compounds A4c was prepared from compound IA5b via a HBTU-mediated amide formation in a fashion similar to the one described for compound A4a. White solid, 49% yield. $^1$H NMR (CDCl$_3$, 600 MHz) δ 8.09 (s, 1H), 7.91 (d, J=8.4 Hz, 2H), 7.81 (d, J=7.8 Hz, 1H), 7.68 (d, J=7.8 Hz, 2H), 7.56 (d, J=7.8, Hz, 2H), 7.44 (dd, J=7.8, 7.8 Hz, 1H), 7.38 (s, 1H), 7.37-7.28 (m, 6H), 7.14 (dd, J=7.2, 7.2 Hz, 1H), 7.00-6.95 (m, 3H), 5.31 (s, 2H), 5.16 (s, 2H), 2.21 (s, 3H), 2.11 (s, 3H). HRMS (ESI$^+$) calcd for $C_{33}H_{31}N_4O_3$ (M+H)$^+$ 531.2396, found 531.2392.

Example 12

Synthesis of N-(3,5-Dimethyl-1-(4-nitrobenzyl)-1H-pyrazol-4-yl)-4-(phenoxymethyl)benzamide (A5a)

Step 1. Synthesis of (E)-N-(3,5-dimethyl-1H-pyrazol-4-yl)-1-phenylmethanimine (IA6)

To a solution of methyl 3,5-dimethyl-4-nitropyrazole (IA1, 2.82 g, 20 mmol) in MeOH (30 mL) was added Pd/C (280 mg, 10% yield and the mixture was allowed to shake under $H_2$ (50 psi) with a hydrogenator at rt for 12 h. The catalyst was removed by filtration over a layer of celite. To the resulting filtrate was added benzaldehyde (2.33 g, 22 mmol) and the mixture was heated at reflux for 4 h. After the solvent was evaporated in vacuo, the residue was purified by flash column chromatography (0-80% EtOAc/hexanes) to afford compound IA6 as yellow oil (3.5 g, 88% over two steps). $^1$H NMR (CDCl$_3$, 600 MHz) δ 8.53 (s, 1H), 7.86 (d, J=7.2 Hz, 2H), 7.49-7.40 (m, 3H), 2.42 (s, 3H), 2.41 (s, 3H). HRMS (ESI$^+$) calcd for $C_{12}H_{14}N_3$ (M+H)$^+$ 200.1182, found 200.1182.

Step 2. Synthesis of (E)-N-(3,5-Dimethyl-1-(4-nitrobenzyl)-1H-pyrazol-4-yl)-1-phenylmethanimine (IA8a)

To a solution of compound IA6 (400 mg, 2.0 mmol) in DMF (20 mL) were added KOtBu (518 mg, 2.40 mmol) and the mixture was allowed to stir at rt for 10 min. 4-Nitrobenzyl bromide (IA7a, 269 mg, 2.40 mmol) was then added and the reaction was allowed to stir at rt for additional 12 h. The reaction mixture was quenched with water (50 mL) and extracted with EtOAc. The organic phase was washed with water and brine, dried over anhydrous $Na_2SO_4$, and concentrated in vacuo. The residue was purified by flash column chromatography (0-80% EtOAc/hexanes) to afford compound IA8a as a gray solid (430 mg, 64%). $^1$H NMR (CDCl$_3$, 600 MHz) δ 8.54 (s, 1H), 8.18 (d, J=8.0 Hz, 2H), 7.88-7.84 (m, 2H), 7.48-7.42 (m, 3H), 7.24 (d, J=7.8 Hz, 2H), 5.34 (s, 2H), 2.43 (s, 3H), 2.29 (s, 3H). HRMS (ESI$^+$) calcd for $C_{19}H_{19}N_4O_2$ (M+H)$^+$ 335.1503, found 335.1501.

Step 3. Synthesis of 3,5-Dimethyl-1-(4-nitrobenzyl)-1H-pyrazol-4-amine (IA9a)

To a solution of imine IA8a (400 mg, 2.0 mmol) in MeOH (20 mL) were added 1 N HCl (5 mL) and the mixture was allowed to stir at rt for 4 h. After the MeOH was evaporated in vacuo, the aqueous phase was extracted with EtOAc to remove the byproduct benzaldehyde. The aqueous layer was basified with saturated NaHCO$_3$ and then extracted with EtOAc. The organic phase was washed with water and brine, dried over anhydrous $K_2CO_3$, and concentrated in vacuo to afford compound IA9a as a yellow oil (220 mg, 74%). $^1$H NMR (CDCl$_3$, 600 MHz) δ 8.15 (d, J=7.8 Hz, 2H), 7.16 (d, J=9.0 Hz, 2H), 5.25 (s, 2H), 2.21 (s, 3H), 2.06 (s, 3H). HRMS (ESI$^+$) calcd for $C_{12}H_{15}N_4O_2$ (M+H)$^+$ 247.1190, found 247.1190.

Step 4. Synthesis of N-(3,5-Dimethyl-1-(4-nitrobenzyl)-1H-pyrazol-4-yl)-4-(phenoxymethyl)benzamide (A5a)

Compounds A5a was prepared from intermediate IA9a, via an EDC-mediated amide formation in a fashion similar to the one described for compound A1. Light yellow solid, 180 mg, 50% yield. $^1$H NMR (CDCl$_3$, 600 MHz) δ 8.15 (d, J=7.8 Hz, 1H), 7.93 (d, J=8.4 Hz, 2H), 7.60-7.55 (m, 3H), 7.45 (dd, J=7.8 Hz, 1H), 7.33-7.27 (m, 3H), 7.01-6.95 (m, 3H), 6.64 (d, J=7.8 Hz, 1H), 5.66 (s, 2H), 5.17 (s, 2H), 2.23 (s, 3H), 2.13 (s, 3H). HRMS (ESI$^+$) calcd for $C_{26}H_{25}N_4O_4$ (M+H)$^+$ 457.1876, found 457.1879.

Example 13

Synthesis of N-(3,5-Dimethyl-1-(3-nitrobenzyl)-1H-pyrazol-4-yl)-4-(phenoxymethyl)benzamide (A5b)

Step 1. Synthesis of (E)-N-(3,5-Dimethyl-1-(3-nitrobenzyl)-1H-pyrazol-4-yl)-1-phenylmethanimine (IA8b)

Intermediate IA8b was prepared with bromide IA7b, in a fashion similar to the one described for intermediate IA8a. Gray solid, 420 mg, 63% yield. $^1$H NMR (CDCl$_3$, 600 MHz) δ 8.54 (s, 1H), 8.14 (d, J=8.4 Hz, 1H), 8.02 (s, 1H), 7.89-7.83 (m, 2H), 7.51 (dd, J=7.8, 7.8 Hz, 1H), 7.47-7.40 (m, 4H), 5.33 (s, 2H), 2.43 (s, 3H), 2.31 (s, 3H). HRMS (ESI$^+$) calcd for $C_{19}H_{19}N_4O_2$ (M+H)$^+$ 335.1503, found 335.1507.

Step 2. Synthesis of 3,5-Dimethyl-1-(3-nitrobenzyl)-1H-pyrazol-4-amine (IA9b)

Intermediate IA9b was prepared with bromide IA8b, in a fashion similar to the one described for intermediate IA9a. Yellow oil, 180 mg, 61% yield. $^1$H NMR (CDCl$_3$, 600 MHz) δ 8.11 (d, J=7.2 Hz, 1H), 7.93 (s, 1H), 7.47 (dd, J=7.8, 7.8 Hz, 1H), 7.34 (d, J=7.8 Hz, 1H), 5.25 (s, 2H), 2.21 (s, 3H), 2.08 (s, 3H). HRMS (ESI$^+$) calcd for $C_{12}H_{15}N_4O_2$ (M+H)$^+$ 247.1190, found 247.1193.

Step 3. Synthesis of N-(3,5-Dimethyl-1-(3-nitrobenzyl)-1H-pyrazol-4-yl)-4-(phenoxymethyl)benzamide (A5b)

Compounds A5b was prepared from intermediate IA9b, via an EDC-mediated amide formation in a fashion similar to the one described for compound A1. Light yellow solid, 180 mg, 54% yield. $^1$H NMR (CDCl$_3$, 600 MHz) δ 8.14 (d, J=8.4 Hz, 1H), 7.99 (s, 1H), 7.91 (d, J 7.8 Hz, 2H), 7.56 (d, J=7.8 Hz, 2H), 7.51 (dd, J=7.8, 7.8 Hz, 1H), 7.44 (d, J=7.8 Hz, 1H), 7.33-7.24 (m, 3H), 7.00-6.97 (m, 3H), 5.32 (s, 2H), 5.16 (s, 2H), 2.21 (s, 3H), 2.15 (s, 3H). HRMS (ESI$^+$) calcd for $C_{26}H_{25}N_4O_4$ (M+H)$^+$ 457.1876, found 457.1879.

Example 14

Synthesis of N-(3,5-Dimethyl-1-(2-nitrobenzyl)-1H-pyrazol-4-yl)-4-(phenoxymethyl)benzamide (A5c)

Step 1. Synthesis of (E)-N-(3,5-Dimethyl-1-(2-nitrobenzyl)-1H-pyrazol-4-yl)-1-phenylmethanimine (IA8c)

Intermediate IA8c was prepared with bromide IA7c, in a fashion similar to the one described for intermediate IA8a. Gray solid, 450 mg, 67% yield. $^1$H NMR (CDCl$_3$, 600 MHz) δ 8.58 (s, 1H), 8.17 (d, J=8.4 Hz, 1H), 7.91-7.85 (m, 2H), 7.53 (dd, J=7.2, 7.2 Hz, 1H), 7.50-7.41 (m, 4H), 6.56 (d, J=7.8 Hz, 1H), 5.68 (s, 2H), 2.44 (s, 3H), 2.29 (s, 3H). HRMS (ESI$^+$) calcd for $C_{19}H_{19}N_4O_2$ (M+H)$^+$ 335.1503, found 335.1505.

Step 2. Synthesis of 3,5-Dimethyl-1-(2-nitrobenzyl)-1H-pyrazol-4-amine (IA9c)

Intermediate IA9c was prepared with bromide IA8c, in a fashion similar to the one described for intermediate IA9a. Yellow oil, 200 mg, 65% yield. $^1$H NMR (CDCl$_3$, 600 MHz) δ 8.13 (d, J=7.8 Hz, 1H), 7.50 (dd, J=7.8, 7.8 Hz, 1H), 7.41 (dd, J=7.8, 7.8 Hz, 1H), 6.45 (d, J=7.8 Hz, 1H), 5.58 (s, 2H), 2.22 (s, 3H), 2.06 (s, 3H). HRMS (ESI$^+$) calcd for $C_{12}H_{15}N_4O_2$ (M+H)$^+$ 247.1190, found 247.1191.

Step 3. Synthesis of N-(3,5-Dimethyl-1-(2-nitrobenzyl)-1H-pyrazol-4-yl)-4-(phenoxymethyl)benzamide (A5c)

Compounds A5c was prepared from intermediate IA9c, via an EDC-mediated amide formation in a fashion similar to the one described for compound A1. Light yellow solid, 200 mg, 54% yield. $^1$H NMR (CDCl$_3$, 600 MHz) δ 8.18 (d, J=8.4 Hz, 2H), 7.91 (d, J=7.8 Hz, 2H), 7.56 (d, J=8.4 Hz, 2H), 7.32-7.27 (m, 3H), 7.26-7.23 (m, 2H), 7.00-6.95 (m, 3H), 5.32 (s, 2H), 5.15 (s, 2H), 2.21 (s, 3H), 2.12 (s, 3H). HRMS (ESI$^+$) calcd for $C_{26}H_{25}N_4O_4$ (M+H)$^+$457.1876, found 457.1878.

Example 15. Synthesis of N-(1-(4-Aminobenzyl)-3,5-dimethyl-1H-pyrazol-4-yl)-4-(phenoxymethyl)benzamide (A6a)

To a solution of compound A5a (180 mg, 0.39 mmol) and NiCl$_2$.6H$_2$O (188 mg, 0.79 mmol) in MeOH (20 mL) was slowly added NaBH$_4$ (60 mg, 1.6 mmol) and the mixture was allowed to stir at rt for 3 h. The reaction was quenched with saturated NH$_4$Cl (50 mL) and the mixture was extracted with EtOAc. The organic phase was washed with water and brine, dried over anhydrous K$_2$CO$_3$, and concentrated in vacuo to afford compound A6a as a light yellow solid (150 mg, 90%). $^1$H NMR (DMSO-d$_6$, 600 MHz) δ 9.49 (s, 1H), 7.96 (d, J=7.8 Hz, 2H), 7.56 (d, J=8.4 Hz, 2H), 7.30 (dd, J=8.1, 8.1 Hz, 2H), 7.02 (d, J=7.8 Hz, 2H), 6.95 (dd, J=7.2, 7.2, Hz, 1H), 6.87 (d, J=7.8 Hz, 2H), 6.50 (d, J=8.4 Hz, 2H), 5.19 (s, 2H), 5.02 (s, 2H), 5.00 (s, 2H), 2.05 (s, 3H), 2.01 (s, 3H). HRMS (ESI$^+$) calcd for $C_{26}H_{27}N_4O_2$ (M+H)$^+$ 427.2134, found 427.2134.

Example 16

Synthesis of N-(1-(3-Aminobenzyl)-3,5-dimethyl-1H-pyrazol-4-yl)-4-(phenoxymethyl)benzamide (A6b)

Compounds A6b was prepared from A5b, in a fashion similar to the one described for compound A6a. White solid, 100 mg, 60% yield. $^1$H NMR (CDCl$_3$, 600 MHz) δ 7.90 (d, J=8.4 Hz, 2H), 7.54 (d, J=8.4 Hz, 2H), 7.32-7.24 (m, 3H), 7.08 (dd, J=7.8, 7.8 Hz, 1H), 7.00-6.94 (m, 3H), 6.56 (d, J=7.8 Hz, 1H), 6.52 (d, J=7.8 Hz, 1H), 6.41 (s, 1H), 5.15 (s, 2H), 5.12 (s, 2H), 3.67 (br s, 2H), 2.20 (s, 3H), 2.10 (s, 3H). HRMS (ESI$^+$) calcd for $C_{26}H_{27}N_4O_2$ (M+H)$^+$ 427.2134, found 427.2137.

Example 17

Synthesis of N-(1-(2-Aminobenzyl)-3,5-dimethyl-1H-pyrazol-4-yl)-4-(phenoxymethyl)benzamide (A6c)

Compounds A6b was prepared from A5b, in a fashion similar to the one described for compound A6a. White solid, 120 mg, 72% yield. $^1$H NMR (CDCl$_3$, 600 MHz) δ 7.87 (d, J=7.8 Hz, 2H), 7.54 (d, J=8.4 Hz, 2H), 7.30 (dd, J=8.4, 8.4 Hz, 2H), 7.14-7.07 (m, 3H), 7.00-6.94 (m, 3H), 6.68 (dd, J=7.2, 7.2 Hz, 1H), 6.65 (d, J=8.4 Hz, 1H), 5.15 (s, 2H), 5.12 (s, 2H), 4.65 (br s, 2H), 2.18 (s, 3H), 2.17 (s, 3H). HRMS (ESI$^+$) calcd for $C_{26}H_{27}N_4O_2$ (M+H)$^+$ 427.2134, found 427.2134.

Example 18

Synthesis of N-(1-(4-Acetamidobenzyl)-3,5-dimethyl-1H-pyrazol-4-yl)-4-(phenoxymethyl)benzamide (A7a)

To a solution of amine A6a (50 mg, 0.12 mmol) and Et$_3$N (33 μL, 0.23 mmol) in anhydrous CH$_2$Cl$_2$ (10 mL) was added acetic anhydride (17 μL, 0.18 mmol) and the mixture was allowed to stir at rt for 12 h. After the solvents were removed, the residue was diluted with EtOAc (30 mL), H$_2$O (10 mL) and saturated NaHCO$_3$ (10 mL). After separation, the organic layer was washed with brine (20 mL) and concentrated. The residue was purified by flash column chromatography (0-15% MeOH/CH$_2$Cl$_2$) to give compound A7a as a white solid (30 mg, 55%). $^1$H NMR (DMSO-d$_6$, 600 MHz) δ 9.93 (s, 1H), 9.52 (s, 1H), 7.96 (d, J=7.8 Hz, 2H), 7.56 (d, J=7.8 Hz, 2H), 7.52 (d, J=7.8 Hz, 2H), 7.30 (dd, J=7.5, 7.5 Hz, 2H), 7.09 (d, J=8.4 Hz, 2H), 7.02 (d, J=7.2 Hz, 2H), 6.95 (dd, J=7.5, 7.5, Hz, 1H), 5.20 (s, 2H), 5.15 (s, 2H), 2.06 (s, 3H), 2.02 (s, 6H). HRMS (ESI$^+$) calcd for $C_{28}H_{29}N_4O_3$ (M+H)$^+$469.2240, found 469.2241.

Example 19

Synthesis of N-(1-(3-Acetamidobenzyl)-3,5-dimethyl-1H-pyrazol-4-yl)-4-(phenoxymethyl)benzamide (A7b)

Compounds A7b was prepared from A6b, in a fashion similar to the one described for compound A7a. White solid, 35 mg, 64% yield. $^1$H NMR (CDCl$_3$, 600 MHz) δ 8.67 (s, 1H), 7.91 (d, J=7.8 Hz, 2H), 7.76 (s, 1H), 7.72 (d, J=8.4 Hz, 1H), 7.50 (d, J=7.2 Hz, 2H), 7.32-7.27 (m, 2H), 7.25 (dd, J=8.1, 8.1 Hz, 1H), 7.02-6.94 (m, 4H), 6.89 (d, J=7.8 Hz, 1H), 5.17 (s, 2H), 5.12 (s, 2H), 2.10 (s, 3H), 2.09 (s, 3H), 2.07 (s, 3H). HRMS (ESI$^+$) calcd for $C_{28}H_{29}N_4O_3$(M+H)$^+$ 469.2240, found 469.2245.

Example 20

Synthesis of N-(1-(2-Acetamidobenzyl)-3,5-dimethyl-1H-pyrazol-4-yl)-4-(phenoxymethyl)benzamide (A7c)

Compounds A7c was prepared from A6c, in a fashion similar to the one described for compound A7a. White solid, 30 mg, 55% yield. $^1$H NMR (CDCl$_3$, 600 MHz) δ 10.48 (s, 1H), 8.10 (d, J=7.8 Hz, 1H), 7.88 (d, J=7.8 Hz, 2H), 7.54 (d, J=8.4 Hz, 2H), 7.33-7.23 (m, 5H), 7.05 (dd, J=7.5, 7.5 Hz, 1H), 7.00-6.94 (m, 3H), 5.14 (s, 2H), 5.12 (s, 2H), 2.27 (s, 3H), 2.23 (s, 3H), 2.18 (s, 3H). HRMS (ESI$^+$) calcd for $C_{28}H_{29}N_4O_3$(M+H)$^+$ 469.2240, found 469.2242.

Example 21

Synthesis of N-(3,5-Dimethyl-1-(3-(methylcarbamoyl)benzyl)-1H-pyrazol-4-yl)-N-methyl-4-(phenoxymethyl)benzamide (B1)

To a solution of compound IA4b (50 mg, 0.11 mmol) in THF (2 mL) at 0° C. was added LDA (1 M in THF, 0.2 mL) dropwise. After MeI (76 mg, 0.54 mmol) was added, the resulting mixture was allowed to stir at 0° C. for 3 h. The reaction was quenched with saturated NH$_4$Cl and extracted with EtOAc. The organic phase was washed with water, brine, dried over anhydrous Na$_2$SO$_4$, and concentrated in vacuo. The residue was dissolved in a solution of MeNH$_2$ (33 wt. % in absolute ethanol), and the solution was heated at 80° C. overnight. After cooled to rt, the reaction mixture was concentrated and the residue was purified by flash column chromatography (60-80% EtOAc/hexanes) to afford B1 as a white solid (3.7 mg, 7% over two steps). $^1$H NMR (CDCl$_3$, 600 MHz) δ 7.56 (s, 1H), 7.51 (d, J=7.6 Hz, 1H), 7.32-7.23 (m, 7H), 6.98 (t, J=7.4 Hz, 1H), 6.94 (d, J=7.5 Hz, 2H), 6.66 (d, J=7.6 Hz, 1H), 6.05 (br s, 1H), 5.15 (d, J=16.0 Hz, 1H), 5.07 (d, J=16.0 Hz, 1H), 5.00 (s, 2H), 3.32 (s, 3H), 2.98 (d, J=4.7 Hz, 3H), 2.17 (s, 3H), 1.82 (s, 3H). HRMS (ESI$^+$) calcd for $C_{29}H_{31}N_4O_3$ (M+H)$^+$ 483.2391, found 483.2382.

Example 22

Synthesis of 3-((3,5-Dimethyl-4-((4-(phenoxymethyl)benzyl)amino)-1H-pyrazol-1-yl)methyl)-N-methylbenzamide (B2)

Step 1. Synthesis of 3-((3,5-Dimethyl-4-nitro-1H-pyrazol-1-yl)methyl)-N-methylbenzamide (IA10

To a solution of 3,5-dimethyl-4-nitropyrazole (IA1, 2.0 g, 14.2 mmol) in DMF (100 mL) were added methyl 3-(bromomethyl)benzoate (IA2c, 3.90 g, 17.0 mmol) and $Cs_2CO_3$ (9.23 g, 28.3 mmol) and the mixture was allowed to stir at rt for 12 h. The reaction was quenched with water (50 mL) and the mixture was extracted with EtOAc. The organic phase was washed with water and brine, dried over anhydrous $Na_2SO_4$, and concentrated in vacuo. The residue was then dissolved in MeNH$_2$/EtOH (33 wt. %, 25 mL) in a sealed tube and heated at 70° C. for 24 h. After the solvent was evaporated in vacuo, the residue was purified by flash column chromatography (0-20% MeOH/CH$_2$Cl$_2$) to afford compound IA10 as a light yellow solid (1.45 g, 36% over two steps). $^1$H NMR (CDCl$_3$, 600 MHz) δ 7.68-7.62 (m, 2H), 7.42 (dd, J=7.2, 7.2 Hz, 1H), 7.25 (d, J=7.8 Hz, 1H), 6.14 (br s, 1H), 5.29 (s, 2H), 3.01 (d, J=4.2 Hz, 3H), 2.57 (s, 3H), 2.54 (s, 3H). HRMS (ESI$^+$) calcd for $C_{14}H_{17}N_4O_3$ (M+H)$^+$289.1295, found 289.1291.

Step 2. Synthesis of 3-((4-Amino-3,5-dimethyl-1H-pyrazol-1-yl)methyl)-N-methylbenzamide (IA11)

Compound IA11 was prepared from intermediate IA10 via a NaBH$_4$/NiCl$_2$-mediated reduction in a fashion similar to the one described for compound IA3a. Yellow oil, 900 mg, 72% yield. $^1$H NMR (CDCl$_3$, 600 MHz) δ 7.63 (d, J=7.8 Hz, 1H), 7.49 (s, 1H), 7.33 (dd, J=7.8, 7.8 Hz, 1H), 7.14 (d, J=7.8 Hz, 1H), 6.32 (br s, 1H), 5.17 (s, 2H), 2.97 (d, J=4.8 Hz, 3H), 2.19 (s, 3H), 2.04 (s, 3H). HRMS (ESI$^+$) calcd for $C_{14}H_{19}N_4O$ (M+H)$^+$ 259.1553, found 259.1549.

Step 3. Synthesis of 3-((3,5-Dimethyl-4-((4-(phenoxymethyl)benzyl)amino)-1H-pyrazol-1-yl)methyl)-N-methylbenzamide (B2)

A solution of intermediate IA11 (40 mg, 0.16 mmol) and 4-(phenoxymethyl)benzaldehyde (33 mg, 0.16 mmol) in CH$_2$Cl$_2$ (3 mL) was allowed to stir at rt overnight. After the solvent was removed, the residue was redissolved in MeOH (3 mL) and the solution was cooled at 0° C. After NaBH$_4$ (11 mg, 0.29 mmol) was added, the reaction mixture was allowed to stir at 0° C. for 2 h before quenched with Saturated NH$_4$Cl. The mixture was then extracted with EtOAc and the organic phase was washed with water, brine, dried over anhydrous Na$_2$SO$_4$, and concentrated in vacuo. The residue was purified by flash column chromatography using (60-80% EtOAc/hexanes) to afford B2 as a yellow solid (15 mg, 21%). $^1$H NMR (CDCl$_3$, 600 MHz) δ 7.61 (d, J=7.6 Hz, 1H), 7.49 (s, 1H), 7.36-7.33 (m, 3H), 7.29-7.24 (m, 4H), 7.07 (d, J=7.6 Hz, 1H), 6.97-6.93 (m, 3H), 6.10 (br s, 1H), 5.16 (s, 2H), 5.04 (s, 2H), 3.98 (s, 2H), 2.98 (d, J=4.7 Hz, 3H), 2.15 (s, 3H), 1.84 (s, 3H). HRMS (ESI$^+$) calcd for $C_{28}H_{31}N_4O_2$ (M+H)$^+$ 455.2442, found 455.2434.

Example 23

Synthesis of 3-((3,5-Dimethyl-4-((4-(phenoxymethyl)phenyl)sulfonamido)-1H-pyrazol-1-yl)methyl)-N-methylbenzamide (B3)

To a solution of intermediate IA11 (37 mg, 0.14 mmol) in THF (3 mL) was added Et$_3$N (82 μL, 0.57 mmol) and 4-(phenoxymethyl)benzenesulfonyl chloride (61 mg, 0.22 mmol). After the reaction mixture was allowed to stir at rt overnight and then quenched with saturated NH$_4$Cl, the mixture was extracted with EtOAc. The organic phase was washed with water, brine, dried over anhydrous Na$_2$SO$_4$, and concentrated in vacuo. The residue was purified by flash column chromatography using (0-10% MeOH/CH$_2$Cl$_2$) to afford B3 as a yellow solid (25 mg, 34%). $^1$H NMR (CDCl$_3$, 600 MHz) δ 7.70 (d, J=8.2 Hz, 2H), 7.66 (d, J=7.6 Hz, 1H), 7.50 (d, J=8.2 Hz, 2H), 7.38 (t, J=7.9 Hz, 1H), 7.33 (s, 1H), 7.29-7.26 (m, 2H), 7.17 (d, J=7.6 Hz, 1H), 6.97 (t, J=7.1 Hz, 1H), 6.92 (d, J=8.2 Hz, 2H), 6.31-6.26 (m, 1H), 6.24 (s, 1H), 5.18 (s, 2H), 5.12 (s, 2H), 2.95 (d, J=4.8 Hz, 3H), 1.86 (s, 3H), 1.66 (s, 3H). HRMS (ESI$^+$) calcd for $C_{27}H_{29}N_4O_4S$ (M+H)$^+$ 505.1904, found 505.1902.

Example 24

Synthesis of 3-((3,5-Dimethyl-4-(4-((phenylthio)methyl)benzamido)-1H-pyrazol-1-yl)methyl)-N-methylbenzamide (C1)

Step 1. Synthesis of 3-((4-(4-(Chloromethyl)benzamido)-3,5-dimethyl-1H-pyrazol-1-yl)methyl)-N-methylbenzamide (IA12)

To a solution of amine IA11 (900 mg, 3.49 mmol) and Et$_3$N (1.00 mL, 7.00 mmol) in anhydrous CH$_2$Cl$_2$ (100 mL) was added 4-(chloromethyl)benzoyl chloride (790 mg, 4.19 mmol) and the mixture was allowed to stir at rt for 12 h. After the solvents were removed, the residue was diluted with EtOAc (50 mL) and H$_2$O (50 mL). After separation, the organic layer was washed with brine (20 mL) and concentrated. The residue was purified by flash column chromatography (0-15% MeOH/CH$_2$Cl$_2$) to give compound IA12 as a white solid (1.10 g, 61%). $^1$H NMR (CDCl$_3$, 600 MHz) δ 7.92 (d, J=7.8 Hz, 2H), 7.71 (d, J=7.8 Hz, 1H), 7.60 (s, 1H), 7.51 (d, J=7.8 Hz, 2H), 7.37 (dd, J=7.2, 7.2 Hz, 1H), 7.29-7.25 (m, 1H), 7.19 (s, 1H), 6.75 (br s, 1H), 5.25 (s, 2H), 4.64 (s, 2H), 2.96 (d, J=4.2 Hz, 3H), 2.17 (s, 3H), 2.05 (s, 3H). HRMS (ESI$^+$) calcd for $C_{22}H_{24}ClN_4O_2$(M+H)$^+$ 411.1582, found 411.1580.

Step 2. Synthesis of 3-((3,5-Dimethyl-4-(4-((phenylthio)methyl)benzamido)-1H-pyrazol-1-yl)methyl)-N-methylbenzamide (C1)

To a solution of compound IA12 (30 mg, 0.073 mmol) in DMF (5 mL) was added Cs$_2$CO$_3$ (36 mg, 0.11 mmol) and thiophenol (8.9 mg, 0.080 mmol) and the reaction mixture was allowed to stir at 50° C. for 14 h. After cooled to rt, the solution was diluted with saturated NH$_4$Cl and extracted with EtOAc. The organic phase was washed with water, brine, dried over anhydrous Na$_2$SO$_4$, and concentrated in vacuo. The residue was purified by flash column chromatography (0-15% MeOH/CH$_2$Cl$_2$) to afford C1 as a white solid (10 mg, 28%). $^1$H NMR (CDCl$_3$, 600 MHz) δ 7.82 (d, J=7.8 Hz, 2H), 7.72 (d, J=7.2 Hz, 1H), 7.45-7.41 (m, 1H), 7.40-7.33 (m, 4H), 7.32-7.29 (m, 1H), 7.29-7.24 (m, 3H), 7.22-7.14 (m, 2H), 6.67-6.60 (m, 1H), 5.26 (s, 2H), 4.15 (s, 2H), 2.97 (d, J=4.8 Hz, 3H), 2.17 (s, 3H), 2.05 (s, 3H). HRMS (ESI$^+$) calcd for $C_{28}H_{29}N_4O_2S$ (M+H)$^+$ 485.2011, found 485.2011.

Example 25

Synthesis of 3-((3,5-Dimethyl-4-(4-((phenylamino)methyl)benzamido)-1H-pyrazol-1-yl)methyl)-N-methylbenzamide (C2)

To a solution of compound IA12 (41 mg, 0.10 mmol) in DMF (1 mL) was added DIPEA (70 µL, 0.40 mmol) and aniline (37 mg, 0.40 mmol). The reaction mixture was allowed to stir at 80° C. for 7 h. After cooled to rt, the solution was diluted with saturated NH$_4$Cl and extracted with EtOAc. The organic phase was washed with water, brine, dried over anhydrous Na$_2$SO$_4$, and concentrated in vacuo. The residue was purified by flash column chromatography (60-80% EtOAc/hexanes) to afford C2 as a white solid (32 mg, 68%). $^1$H NMR (CDCl$_3$, 600 MHz) δ 7.88 (d, J=8.2 Hz, 2H), 7.70 (d, J=7.7 Hz, 1H), 7.57 (s, 1H), 7.47 (d, J=8.2 Hz, 2H), 7.36 (t, J=7.7 Hz, 1H), 7.25 (d, J=7.7 Hz, 1H), 7.18-7.14 (m, 3H), 6.75 (br s, 1H), 6.72 (t, J=7.4 Hz, 1H), 6.61 (d, J=7.9 Hz, 2H), 5.23 (s, 2H), 4.42 (s, 2H), 4.23 (br s, 1H), 2.95 (d, J=4.8 Hz, 3H), 2.16 (s, 3H), 2.04 (s, 3H). HRMS (ESI$^+$) calcd for $C_{28}H_{30}N_5O_2$ (M+H)$^+$ 468.2394, found 468.2402.

Example 26

Synthesis of 3-((3,5-Dimethyl-4-(4-phenethylbenzamido)-1H-pyrazol-1-yl)methyl)-N-methylbenzamide (C3)

Compounds C3 was prepared from intermediate IA11 via an EDC- or HBTU-mediated amide formation in a fashion similar to the one described for compound A1 or A4a. White solid, 19 mg, 27% yield. $^1$H NMR (CDCl$_3$, 600 MHz) δ 7.82 (d, J=7.9 Hz, 2H), 7.74 (d, J=7.9 Hz, 1H), 7.39 (t, J=7.7 Hz, 1H), 7.32 (s, 1H), 7.30-7.26 (m, 5H), 7.21 (t, J=7.7 Hz, 1H), 7.17 (d, J=7.7 Hz, 2H), 7.13 (s, 1H), 6.63 (q, J=4.2 Hz, 1H), 5.28 (s, 2H), 3.03-2.93 (m, 7H), 2.20 (s, 3H), 2.07 (s, 3H). HRMS (ESI$^+$) calcd for $C_{29}H_{31}N_4O_2$ (M+H)$^+$ 467.2442, found 467.2444.

Example 27

Synthesis of N$^1$-(3,5-Dimethyl-1-(3-(methylcarbamoyl)benzyl)-1H-pyrazol-4-yl)-N$^4$-phenylterephthalamide (C4)

Compounds C3 was prepared from intermediate IA11 via an EDC- or HBTU-mediated amide formation in a fashion similar to the one described for compound A1 or A4a. White solid, 19 mg, 27% yield. $^1$H NMR (DMSO-d6, 600 MHz) δ 10.34 (s, 1H), 9.71 (s, 1H), 8.42 (q, J=4.1 Hz, 1H), 8.07 (dd, J$_1$=11.9 Hz, J$_2$=8.7 Hz, 4H), 7.78 (d, J=7.6 Hz, 2H), 7.71 (d, J=7.6 Hz, 1H), 7.67 (s, 1H), 7.42 (t, J=7.9 Hz, 1H), 7.35 (t, J=7.9 Hz, 2H), 7.25 (d, J=7.6 Hz, 1H), 7.11 (t, J=7.4 Hz, 1H), 5.27 (s, 2H), 2.76 (d, J=4.6 Hz, 3H), 2.08 (s, 3H), 2.04 (s, 3H). HRMS (ESI$^+$) calcd for $C_{28}H_{28}N_5O_3$ (M+H)$^+$ 482.2187, found 482.2179.

Example 28

Synthesis of 3-((4-(4-(Benzyloxy)benzamido)-3,5-dimethyl-1H-pyrazol-1-yl)methyl)-N-methylbenzamide (C5)

Compounds C3 was prepared from intermediate IA11 via an EDC- or HBTU-mediated amide formation in a fashion similar to the one described for compound A1 or A4a. White solid, 26 mg, 57% yield. $^1$H NMR (CDCl$_3$, 600 MHz,) δ 7.89 (d, J=8.7 Hz, 2H), 7.70 (d, J=7.6 Hz, 1H), 7.59 (s, 1H), 7.43 (d, J=7.4 Hz, 2H), 7.40 (t, J=7.4 Hz, 2H), 7.34 (t, J=7.4 Hz, 2H), 7.24 (d, J=7.6 Hz, 1H), 7.15 (s, 1H), 7.03 (d, J=8.7 Hz, 2H), 6.88-6.84 (m, 1H), 5.22 (s, 2H), 5.13 (s, 2H), 2.94 (d, J=4.7 Hz, 3H), 2.15 (s, 3H), 2.02 (s, 3H). HRMS (ESI$^+$) calcd for $C_{28}H_{29}N_4O_3$ (M+H)$^+$ 469.2234, found 469.2244.

Example 29

Synthesis of N-(3,5-Dimethyl-1-(3-(methylcarbamoyl)benzyl)-1H-pyrazol-4-yl)-3-(phenoxymethyl)benzamide (C6)

Compounds C3 was prepared from intermediate IA11 via an EDC- or HBTU-mediated amide formation in a fashion similar to the one described for compound A1 or A4a. White solid, 27 mg, 51% yield. $^1$H NMR (CDCl$_3$, 600 MHz) δ 8.01 (s, 1H), 7.88 (d, J=7.6 Hz, 1H), 7.70 (d, J=7.6 Hz, 1H), 7.65-7.61 (m, 2H), 7.50 (t, J=7.6 Hz, 1H), 7.35 (t, J=7.6 Hz, 1H), 7.30 (t, J=7.7 Hz, 2H), 7.25 (d, J=7.7 Hz, 1H), 7.18 (s, 1H), 7.00-6.96 (m, 3H), 6.76-6.71 (m, 1H), 5.23 (s, 2H), 5.12 (s, 2H), 2.95 (d, J=4.7 Hz, 3H), 2.17 (s, 3H), 2.04 (s, 3H). HRMS (ESI$^+$) calcd for $C_{28}H_{29}N_4O_3$ (M+H)$^+$ 469.2234, found 469.2241.

Example 30

Synthesis of 3-((4-(4-((Cyclohexyloxy)methyl)benzamido)-3,5-dimethyl-1H-pyrazol-1-yl)methyl)-N-methylbenzamide (C7)

Compounds C3 was prepared from intermediate IA11 via an EDC- or HBTU-mediated amide formation in a fashion similar to the one described for compound A1 or A4a. White solid, 9.3 mg, 17% yield. $^1$H NMR (DMSO-d$_6$, 600 MHz) δ 9.52 (s, 1H), 8.46-8.40 (m, 1H), 7.93 (d, J=8.4 Hz, 2H), 7.72 (d, J=7.8 Hz, 1H), 7.68 (s, 1H), 7.45-7.40 (m, 3H), 7.26 (d, J=7.8 Hz, 1H), 5.27 (s, 2H), 4.56 (s, 2H), 3.38-3.33 (m, 1H), 2.77 (d, J=4.8 Hz, 3H), 2.07 (s, 3H), 2.03 (s, 3H), 1.91-1.84 (m, 2H), 1.70-1.64 (m, 2H), 1.33-1.20 (m, 6H). HRMS (ESI$^+$) calcd for $C_{28}H_{35}N_4O_3$ (M+H)$^+$ 475.2709, found 475.2707.

Example 31

Synthesis of 3-((3,5-Dimethyl-4-(4-((naphthalen-2-yloxy)methyl)benzamido)-1H-pyrazol-1-yl)methyl)-N-methylbenzamide (D1)

To a solution of compound IA12 (30 mg, 0.073 mmol) in DMF (5 mL) was added Cs$_2$CO$_3$ (36 mg, 0.11 mmol) and 2-naphthol (12 mg, 0.080 mmol) and the reaction mixture was allowed to stir at 50° C. for 14 h. After cooled to rt, the solution was diluted with saturated NH$_4$Cl and extracted with EtOAc. The organic phase was washed with water, brine, dried over anhydrous Na$_2$SO$_4$, and concentrated in vacuo. The residue was purified by flash column chromatography (0-15% MeOH/CH$_2$Cl$_2$) to afford D1 as a white solid (5.0 mg, 13%). $^1$H NMR (CDCl$_3$, 600 MHz) δ 8.00 (d, J=7.8 Hz, 2H), 7.77 (dd, J=6.9, 6.9 Hz, 2H), 7.73 (dd, J=7.5, 7.5 Hz, 2H), 7.66 (d, J=7.8 Hz, 2H), 7.59 (s, 1H), 7.46-7.39 (m, 2H), 7.34-7.29 (m, 3H), 7.24 (d, J=8.4 Hz, 1H), 5.33 (s, 2H), 5.31 (s, 2H), 2.91 (s, 3H), 2.18 (s, 3H), 2.15 (s, 3H). HRMS (ESI$^+$) calcd for C$_{32}$H$_{31}$N$_4$O$_3$ (M+H)$^+$ 519.2396, found 519.2398.

Example 32

Synthesis of 3-((3,5-Dimethyl-4-(4-((naphthalen-1-yloxy)methyl)benzamido)-1H-pyrazol-1-yl)methyl)-N-methylbenzamide (D2)

Compound D2 was prepared from intermediate IA12 via a displacement reaction by a phenol in a fashion similar to the one described for compound D1. Light yellow solid, 18 mg, 48% yield. $^1$H NMR (CDCl$_3$, 600 MHz) δ 8.35 (d, J=8.4 Hz, 1H), 7.96 (d, J=7.2 Hz, 2H), 7.82 (d, J=7.8 Hz, 1H), 7.72 (d, J=7.8 Hz, 1H), 7.65 (d, J=8.4 Hz, 2H), 7.53-7.48 (m, 2H), 7.47-7.43 (m, 2H), 7.40-7.33 (m, 2H), 7.28-7.25 (m, 1H), 7.17 (s, 1H), 6.86 (d, J=7.2 Hz, 1H), 6.65-6.60 (m, 1H), 5.34 (s, 2H), 5.27 (s, 2H), 2.98 (d, J=4.8 Hz, 3H), 2.20 (s, 3H), 2.07 (s, 3H). HRMS (ESI$^+$) calcd for C$_{32}$H$_{31}$N$_4$O$_3$ (M+H)$^+$ 519.2396, found 519.2392.

Example 33

Synthesis of 3-((3,5-Dimethyl-4-(4-((o-tolyloxy)methyl)benzamido)-1H-pyrazol-1-yl)methyl)-N-methylbenzamide (D3a)

Compound D3a was prepared from intermediate IA12 via a displacement reaction by a phenol in a fashion similar to the one described for compound D1. White solid, 20 mg, 57% yield. $^1$H NMR (CDCl$_3$, 600 MHz) δ 7.91 (d, J=7.8 Hz, 2H), 7.74 (d, J=7.2 Hz, 1H), 7.56 (d, J=8.4 Hz, 2H), 7.40 (dd, J=8.1, 8.1 Hz, 1H), 7.30-7.27 (m, 2H), 7.15 (s, 1H), 7.09 (d, J=7.8 Hz, 2H), 6.87 (d, J=7.8 Hz, 2H), 6.59-6.53 (m, 1H), 5.29 (s, 2H), 5.13 (s, 2H), 3.00 (d, J=4.8 Hz, 3H), 2.29 (s, 3H), 2.21 (s, 3H), 2.09 (s, 3H). HRMS (ESI$^+$) calcd for C$_{29}$H$_{31}$N$_4$O$_3$ (M+H)$^+$ 483.2396, found 483.2396.

Example 34

Synthesis of 3-((3,5-Dimethyl-4-(4-((m-tolyloxy)methyl)benzamido)-1H-pyrazol-1-yl)methyl)-N-methylbenzamide (D3b)

Compound D3b was prepared from intermediate IA12 via a displacement reaction by a phenol in a fashion similar to the one described for compound D1. White solid, 25 mg, 71% yield. $^1$H NMR (CDCl$_3$, 600 MHz) δ 7.93 (d, J=8.4 Hz, 2H), 7.70 (d, J=7.8 Hz, 1H), 7.60 (s, 1H), 7.54 (d, J=7.8 Hz, 2H), 7.36 (dd, J=7.8, 7.8 Hz, 1H), 7.26-7.23 (m, 1H), 7.20-7.15 (m, 2H), 6.82-6.78 (m, 2H), 6.78-6.72 (m, 2H), 5.24 (s, 2H), 5.13 (s, 2H), 2.96 (d, J=4.8 Hz, 3H), 2.33 (s, 3H), 2.17 (s, 3H), 2.04 (s, 3H). HRMS (ESI$^+$) calcd for C$_{29}$H$_{31}$N$_4$O$_3$(M+H)$^+$483.2396, found 483.2393.

Example 35

Synthesis of 3-((3,5-Dimethyl-4-(4-((p-tolyloxy)methyl)benzamido)-1H-pyrazol-1-yl)methyl)-N-methylbenzamide (D3c)

Compound D3c was prepared from intermediate IA12 via a displacement reaction by a phenol in a fashion similar to the one described for compound D1. White solid, 13 mg, 37% yield. $^1$H NMR (CDCl$_3$, 600 MHz) δ 7.95 (d, J=7.8 Hz, 2H), 7.70 (d, J=7.8 Hz, 1H), 7.64 (s, 1H), 7.56 (d, J=7.8 Hz, 2H), 7.36 (dd, J=7.8, 7.8 Hz, 1H), 7.26-7.23 (m, 1H), 7.20-7.17 (m, 2H), 7.14 (dd, J=7.5, 7.5 Hz, 1H), 6.90 (dd, J=7.8, 7.8 Hz, 1H), 6.85 (d, J=8.4 Hz, 1H), 6.80-6.75 (m, 1H), 5.23 (s, 2H), 5.16 (s, 2H), 2.95 (d, J=4.2 Hz, 3H), 2.31 (s, 3H), 2.16 (s, 3H), 2.04 (s, 3H). HRMS (ESI$^+$) calcd for C$_{29}$H$_{31}$N$_4$O$_3$ (M+H)$^+$ 483.2396, found 483.2398.

Example 36

Synthesis of 3-((4-(4-((2-Methoxyphenoxy)methyl)benzamido)-3,5-dimethyl-1H-pyrazol-1-yl)methyl)-N-methylbenzamide (D4a)

Compound D4a was prepared from intermediate IA12 via a displacement reaction by a phenol in a fashion similar to the one described for compound D1. White solid, 22 mg, 60% Yield. $^1$H NMR (CDCl$_3$, 600 MHz) δ 7.91 (d, J=8.4 Hz, 2H), 7.72 (d, J=7.8 Hz, 1H), 7.56 (d, J=8.4 Hz, 2H), 7.44 (s, 1H), 7.38 (dd, J=7.5, 7.5 Hz, 1H), 7.28-7.26 (m, 1H), 7.16 (s, 1H), 6.98-6.92 (m, 2H), 6.89-6.83 (m, 2H), 6.68-6.62 (m, 1H), 5.26 (s, 2H), 5.24 (s, 2H), 3.91 (s, 3H), 2.98 (d, J=4.8 Hz, 3H), 2.19 (s, 3H), 2.06 (s, 3H). HRMS (ESI$^+$) calcd for C$_{29}$H$_{31}$N$_4$O$_4$ (M+H)$^+$ 499.2345, found 499.2348.

Example 37

Synthesis of 3-((4-(4-((3-Methoxyphenoxy)methyl)benzamido)-3,5-dimethyl-1H-pyrazol-1-yl)methyl)-N-methylbenzamide (D4b)

Compound D4b was prepared from intermediate IA12 via a displacement reaction by a phenol in a fashion similar to the one described for compound D1. White solid, 26 mg, 71% yield. $^1$H NMR (CDCl$_3$, 600 MHz) δ 7.94 (d, J=8.4 Hz, 2H), 7.75 (s, 1H), 7.69 (d, J=7.2 Hz, 1H), 7.53 (d, J=8.4 Hz, 2H), 7.34 (dd, J=7.8, 7.8 Hz, 1H), 7.24 (d, J=7.2 Hz, 1H), 7.21-7.16 (m, 2H), 6.86-6.81 (m, 1H), 6.56 (d, J=8.4 Hz, 1H), 6.55-6.52 (m, 2H), 5.21 (s, 2H), 5.12 (s, 2H), 3.78 (s, 3H), 2.94 (d, J=4.8 Hz, 3H), 2.14 (s, 3H), 2.02 (s, 3H). HRMS (ESI$^+$) calcd for C$_{29}$H$_{31}$N$_4$O$_4$(M+H)$^+$ 499.2345, found 499.2350.

Example 38

Synthesis of 3-((4-(4-((4-Methoxyphenoxy)methyl)benzamido)-3,5-dimethyl-1H-pyrazol-1-yl)methyl)-N-methylbenzamide (D4c)

Compound D4c was prepared from intermediate IA12 via a displacement reaction by a phenol in a fashion similar to the one described for compound D1. White solid, 28 mg, 77% yield. $^1$H NMR (CDCl$_3$, 600 MHz) δ 7.92 (d, J=7.2 Hz, 2H), 7.74 (d, J=7.2 Hz, 1H), 7.56 (d, J=7.8 Hz, 2H), 7.40 (dd, J=7.8, 7.8 Hz, 1H), 7.31-7.27 (m, 2H), 7.15 (s, 1H), 6.91 (d, J=8.4 Hz, 2H), 6.84 (d, J=7.8 Hz, 2H), 6.58-6.53 (m, 1H), 5.29 (s, 2H), 5.11 (s, 2H), 3.77 (s, 3H), 3.00 (d, J=4.2 Hz, 3H), 2.21 (s, 3H), 2.09 (s, 3H). HRMS (ESI$^+$) calcd for C$_{29}$H$_{31}$N$_4$O$_4$ (M+H)$^+$ 499.2345, found 499.2349.

Example 39

Synthesis of 3-((4-(4-((2-Chlorophenoxy)methyl)benzamido)-3,5-dimethyl-1H-pyrazol-1-yl)methyl)-N-methylbenzamide (D5a)

Compound D5a was prepared from intermediate IA12 via a displacement reaction by a phenol in a fashion similar to the one described for compound D1. White solid, 15 mg, 41% yield. $^1$H NMR (CDCl$_3$, 600 MHz) δ 7.94 (d, J=8.4 Hz, 2H), 7.73 (d, J=7.8 Hz, 1H), 7.61 (d, J=8.4 Hz, 2H), 7.42-7.36 (m, 3H), 7.29-7.26 (m, 1H), 7.20 (dd, J=7.8, 7.8 Hz, 1H), 7.16 (s, 1H), 6.97-6.91 (m, 2H), 6.63-6.58 (m, 1H), 5.28 (s, 2H), 5.24 (s, 2H), 2.99 (d, J=4.8 Hz, 3H), 2.20 (s, 3H), 2.08 (s, 3H). HRMS (ESI$^+$) calcd for C$_{28}$H$_{28}$ClN$_4$O$_3$ (M+H)$^+$ 503.1850, found 503.1846.

Example 40

Synthesis of 3-((4-(4-((3-Chlorophenoxy)methyl) benzamido)-3,5-dimethyl-1H-pyrazol-1-yl)methyl)-N-methylbenzamide (D5b)

Compound D5b was prepared from intermediate IA12 via a displacement reaction by a phenol in a fashion similar to the one described for compound D1. White solid, 36 mg, 95% yield. $^1$H NMR (CDCl$_3$, 600 MHz) δ 7.94 (d, J=7.8 Hz, 2H), 7.72 (d, J=8.4 Hz, 1H), 7.55 (d, J=7.8 Hz, 2H), 7.41 (s, 1H), 7.39 (dd, J=7.8, 7.8 Hz, 1H), 7.28-7.25 (m, 1H), 7.21 (dd, J=8.4, 8.4 Hz, 1H), 7.17 (s, 1H), 7.00-6.95 (m, 2H), 6.88-6.84 (m, 1H), 6.64-6.57 (m, 1H), 5.27 (s, 2H), 5.14 (s, 2H), 2.99 (d, J=4.8 Hz, 3H), 2.20 (s, 3H), 2.07 (s, 3H). HRMS (ESI$^+$) calcd for C$_{28}$H$_{28}$ClN$_4$O$_3$(M+H)$^+$ 503.1850, found 503.1857.

Example 41

Synthesis of 3-((4-(4-((4-Chlorophenoxy)methyl) benzamido)-3,5-dimethyl-1H-pyrazol-1-yl)methyl)-N-methylbenzamide (D5c)

Compound D5c was prepared from intermediate IA12 via a displacement reaction by a phenol in a fashion similar to the one described for compound D1. White solid, 30 mg, 82% yield. $^1$H NMR (CDCl$_3$, 600 MHz) δ 7.93 (d, J=7.8 Hz, 2H), 7.73 (d, J=7.2 Hz, 1H), 7.55 (d, J=7.2 Hz, 2H), 7.39 (dd, J=7.8, 7.8 Hz, 1H), 7.34 (s, 1H), 7.10-7.22 (m, 3H), 7.17 (s, 1H), 6.90 (d, J=7.8 Hz, 2H), 6.60-6.54 (m, 1H), 5.29 (s, 2H), 5.13 (s, 2H), 2.99 (d, J=4.8 Hz, 3H), 2.20 (s, 3H), 2.08 (s, 3H). HRMS (ESI$^+$) calcd for C$_{28}$H$_{28}$ClN$_4$O$_3$(M+H)$^+$ 503.1850, found 503.1858.

Example 42

Synthesis of 3-((4-(4-((2-Fluorophenoxy)methyl) benzamido)-3,5-dimethyl-1H-pyrazol-1-yl)methyl)-N-methylbenzamide (D6a)

Compound D6a was prepared from intermediate IA12 via a displacement reaction by a phenol in a fashion similar to the one described for compound D1. White solid, 21 mg, 59% yield. $^1$H NMR (600 MHz, CDCl$_3$) δ 7.92 (d, J=7.8 Hz, 2H), 7.73 (d, J=7.2 Hz, 1H), 7.58 (d, J=8.4 Hz, 2H), 7.39 (dd, J=7.8, 7.8 Hz, 1H), 7.35 (s, 1H), 7.27 (d, J=7.8 Hz, 1H), 7.16 (s, 1H), 7.11 (dd, J=12.0, 7.8 Hz, 1H), 7.04 (dd, J=7.8, 7.8 Hz, 1H), 6.99 (dd, J=8.4, 8.4 Hz, 1H), 6.94 (dd, J=12.6, 7.8 Hz, 1H), 6.60-6.57 (m, 1H), 5.28 (s, 2H), 5.23 (s, 2H), 2.99 (d, J=4.8 Hz, 3H), 2.20 (s, 3H), 2.08 (s, 3H). HRMS (ESI$^+$) calcd for C$_{28}$H$_{28}$ClN$_4$O$_3$(M+H)$^+$487.2145, found 487.2146.

Example 43

Synthesis of 3-((4-(4-((3-Fluorophenoxy)methyl) benzamido)-3,5-dimethyl-1H-pyrazol-1-yl)methyl)-N-methylbenzamide (D6b)

Compound D6b was prepared from intermediate IA12 via a displacement reaction by a phenol in a fashion similar to the one described for compound D1. White solid, 24 mg, 67% yield. $^1$H NMR (CDCl$_3$, 600 MHz) δ 7.93 (d, J=7.8 Hz, 2H), 7.73 (d, J=7.8 Hz, 1H), 7.56 (d, J=7.2 Hz, 2H), 7.39 (dd, J=8.1, 8.1 Hz, 1H), 7.35 (s, 1H), 7.28 (d, J=7.2 Hz, 1H), 7.23 (dd, J=7.8, 7.8 Hz, 1H), 7.17 (s, 1H), 6.76 (d, J=8.4 Hz, 1H), 6.72-6.66 (m, 2H), 6.60-6.54 (m, 1H), 5.28 (s, 2H), 5.14 (s, 2H), 2.99 (d, J=4.8 Hz, 3H), 2.21 (s, 3H), 2.08 (s, 3H).

HRMS (ESI$^+$) calcd for C$_{28}$H$_{28}$FN$_4$O$_3$(M+H)$^+$ 487.2145, found 487.2141.

Example 44

Synthesis of 3-((4-(4-((4-Fluorophenoxy)methyl) benzamido)-3,5-dimethyl-1H-pyrazol-1-yl)methyl)-N-methylbenzamide (D6c)

Compound D6c was prepared from intermediate IA12 via a displacement reaction by a phenol in a fashion similar to the one described for compound D1. White solid, 12 mg, 34% yield. $^1$H NMR (CDCl$_3$, 600 MHz) δ 7.93 (d, J=7.8 Hz, 2H), 7.73 (d, J=7.8 Hz, 1H), 7.55 (d, J=7.2 Hz, 2H), 7.42-7.35 (m, 2H), 7.29-7.26 (m, 1H), 7.17 (s, 1H), 6.99 (dd, J=8.4, 8.4 Hz, 2H), 6.94-6.88 (m, 2H), 6.63-6.56 (m, 1H), 5.28 (s, 2H), 5.12 (s, 2H), 2.99 (d, J=4.2 Hz, 3H), 2.20 (s, 3H), 2.08 (s, 3H). HRMS (ESI$^+$) calcd for C$_{28}$H$_{28}$FN$_4$O$_3$ (M+H)$^+$ 487.2145, found 487.2147.

Example 45

Synthesis of 3-((4-(4-((2-Cyanophenoxy)methyl) benzamido)-3,5-dimethyl-1H-pyrazol-1-yl)methyl)-N-methylbenzamide (D7a)

Compound D7a was prepared from intermediate IA12 via a displacement reaction by a phenol in a fashion similar to the one described for compound D1. White solid, 30 mg, 83% yield. $^1$H NMR (CDCl$_3$, 600 MHz) δ 7.95 (d, J=8.4 Hz, 2H), 7.84 (s, 1H), 7.70 (d, J=7.8 Hz, 1H), 7.60 (d, J=7.2 Hz, 1H), 7.57 (d, J=8.4 Hz, 2H), 7.52 (dd, J=7.8, 7.8 Hz, 1H), 7.35 (dd, J=7.8, 7.8 Hz, 1H), 7.24 (d, J=7.8 Hz, 1H), 7.19 (s, 1H), 7.05 (dd, J=7.5, 7.5 Hz, 1H), 7.00 (d, J=8.4 Hz, 1H), 6.83-6.77 (m, 1H), 5.27 (s, 2H), 5.22 (s, 2H), 2.94 (d, J=4.8 Hz, 3H), 2.15 (s, 3H), 2.03 (s, 3H). HRMS (ESI$^+$) calcd for C$_{29}$H$_{28}$N$_5$O$_3$(M+H)$^+$494.2192, found 494.2188.

Example 46

Synthesis of 3-((4-(4-((3-Cyanophenoxy)methyl) benzamido)-3,5-dimethyl-1H-pyrazol-1-yl)methyl)-N-methylbenzamide (D7b)

Compound D7b was prepared from intermediate IA12 via a displacement reaction by a phenol in a fashion similar to the one described for compound D1. White solid, 28 mg, 78% yield. $^1$H NMR (CDCl$_3$, 600 MHz) δ 7.98 (d, J=8.4 Hz, 2H), 7.79 (s, 1H), 7.69 (d, J=7.2 Hz, 1H), 7.53 (d, J=8.4 Hz, 2H), 7.39 (dd, J=8.1, 8.1 Hz, 1H), 7.34 (dd, J=7.8, 7.8 Hz, 1H), 7.27 (d, J=5.4 Hz, 1H), 7.24 (d, J=7.8 Hz, 1H), 7.22-7.18 (m, 3H), 6.85-6.80 (m, 1H), 5.22 (s, 2H), 5.17 (s, 2H), 2.94 (d, J=4.8 Hz, 3H), 2.15 (s, 3H), 2.03 (s, 3H). HRMS (ESI$^+$) calcd for C$_{29}$H$_{28}$N$_5$O$_3$(M+H)$^+$ 494.2192, found 494.2195.

Example 47

Synthesis of 3-((4-(4-((4-Cyanophenoxy)methyl)benzamido)-3,5-dimethyl-1H-pyrazol-1-yl)methyl)-N-methylbenzamide (D7c)

Compound D7c was prepared from intermediate IA12 via a displacement reaction by a phenol in a fashion similar to the one described for compound D1. White solid, 28 mg, 78% yield. $^1$H NMR (CDCl$_3$, 600 MHz) δ 7.95 (d, J=8.4 Hz, 2H), 7.72 (d, J=7.8 Hz, 1H), 7.60 (d, J=8.4 Hz, 2H), 7.55 (d, J=7.8 Hz, 2H), 7.42-7.34 (m, 2H), 7.28 (d, J=7.8 Hz, 1H), 7.18 (s, 1H), 7.03 (d, J=9.0 Hz, 2H), 6.58-6.54 (m, 1H), 5.28 (s, 2H), 5.21 (s, 2H), 2.99 (d, J=4.8 Hz, 3H), 2.20 (s, 3H), 2.08 (s, 3H). HRMS (ESI$^+$) calcd for C$_{29}$H$_{28}$N$_5$O$_3$(M+H)$^+$ 494.2192, found 494.2186.

Example 48

Synthesis of 3-((3,5-Dimethyl-4-(4-((2-nitrophenoxy)methyl)benzamido)-1H-pyrazol-1-yl)methyl)-N-methylbenzamide (D8a)

Compound D8a was prepared from intermediate IA12 via a displacement reaction by a phenol in a fashion similar to the one described for compound D1. White solid, 9.0 mg, 24% yield. $^1$H NMR (CDCl$_3$, 600 MHz) δ 7.94 (d, J=8.4 Hz, 2H), 7.89 (dd, J=8.1, 1.5 Hz, 1H), 7.73 (d, J=7.8 Hz, 1H), 7.61 (d, J=8.4 Hz, 2H), 7.53 (dd, J=7.8, 7.8 Hz, 1H), 7.43 (s, 1H), 7.39 (dd, J=7.8, 7.8 Hz, 1H), 7.29-7.26 (m, 1H), 7.17 (s, 1H), 7.13 (d, J=8.4 Hz, 1H), 7.08 (dd, J=7.5, 7.5 Hz, 1H), 6.62-6.56 (m, 1H), 5.31 (s, 2H), 5.28 (s, 2H), 2.99 (d, J=4.8 Hz, 3H), 2.20 (s, 3H), 2.08 (s, 3H). HRMS (ESI$^+$) calcd for C$_{28}$H$_{28}$N$_5$O$_5$ (M+H)$^+$ 514.2090, found 514.2092.

Example 49

Synthesis of 3-((3,5-Dimethyl-4-(4-((3-nitrophenoxy)methyl)benzamido)-1H-pyrazol-1-yl)methyl)-N-methylbenzamide (D8b)

Compound D8b was prepared from intermediate IA12 via a displacement reaction by a phenol in a fashion similar to the one described for compound D1. White solid, 14 mg, 37% yield. $^1$H NMR (CDCl$_3$, 600 MHz) δ 7.97 (d, J=7.2 Hz, 2H), 7.86 (d, J=7.8 Hz, 1H), 7.81 (s, 1H), 7.71 (d, J=7.8 Hz, 1H), 7.57 (d, J=7.8 Hz, 2H), 7.54-7.50 (m, 1H), 7.46 (dd, J=8.1, 8.1 Hz, 1H), 7.37 (dd, J=7.5, 7.5 Hz, 1H), 7.31 (dd, J=8.4, 1.2 Hz, 1H), 7.28-7.26 (m, 1H), 7.18 (s, 1H), 6.67-6.62 (m, 1H), 5.26 (s, 2H), 5.23 (s, 2H), 2.98 (d, J=4.8 Hz, 3H), 2.18 (s, 3H), 2.06 (s, 3H). HRMS (ESI$^+$) calcd for C$_{28}$H$_{28}$N$_5$O$_5$ (M+H)$^+$ 514.2090, found 514.2093.

Example 50

Synthesis of 3-((3,5-Dimethyl-4-(4-((4-nitrophenoxy)methyl)benzamido)-1H-pyrazol-1-yl)methyl)-N-methylbenzamide (D8c)

Compound D8c was prepared from intermediate IA12 via a displacement reaction by a phenol in a fashion similar to the one described for compound D1. White solid, 23 mg, 61% yield. $^1$H NMR (CDCl$_3$, 600 MHz) δ 8.21 (d, J=9.0 Hz, 2H), 7.99 (d, J=7.8 Hz, 2H), 7.72 (s, 1H), 7.69 (d, J=7.2 Hz, 1H), 7.54 (d, J=8.4 Hz, 2H), 7.35 (dd, J=8.1, 8.1 Hz, 1H), 7.25 (d, J=7.8 Hz, 1H), 7.20 (s, 1H), 7.04 (d, J=9.0 Hz, 2H), 6.79-6.73 (m, 1H), 5.25 (s, 2H), 5.23 (s, 2H), 2.95 (d, J=4.8 Hz, 3H), 2.15 (s, 3H), 2.04 (s, 3H). HRMS (ESI$^+$) calcd for C$_{28}$H$_{28}$N$_5$O$_5$ (M+H)$^+$ 514.2090, found 514.2088.

Example 51

Synthesis of 3-((3,5-Dimethyl-4-(4-((2-(trifluoromethyl)phenoxy)methyl)benzamido)-1H-pyrazol-1-yl)methyl)-N-methylbenzamide (D9a)

Compound D9a was prepared from intermediate IA12 via a displacement reaction by a phenol in a fashion similar to the one described for compound D1. White solid, 31 mg, 79% yield. $^1$H NMR (CDCl$_3$, 600 MHz) δ 7.96 (d, J=8.4 Hz, 2H), 7.82 (s, 1H), 7.69 (d, J=7.2 Hz, 1H), 7.61 (d, J=7.8 Hz, 1H), 7.55 (d, J=7.8 Hz, 2H), 7.48 (dd, J=8.1, 8.1 Hz, 1H), 7.33 (dd, J=7.8, 7.8 Hz, 1H), 7.23 (d, J=7.2 Hz, 1H), 7.18 (s, 1H), 7.06-7.00 (m, 2H), 6.89-6.83 (m, 1H), 5.24 (s, 2H), 5.20 (s, 2H), 2.93 (d, J=4.8 Hz, 3H), 2.14 (s, 3H), 2.02 (s, 3H). HRMS (ESI$^+$) calcd for C$_{29}$H$_{28}$F$_3$N$_4$O$_3$(M+H)$^+$ 537.2114, found 537.2108.

Example 52

Synthesis of 3-((3,5-Dimethyl-4-(4-((3-(trifluoromethyl)phenoxy)-methyl)benzamido)-1H-pyrazol-1-yl)methyl)-N-methylbenzamide (D9b)

Compound D9b was prepared from intermediate IA12 via a displacement reaction by a phenol in a fashion similar to the one described for compound D1. White solid, 17 mg, 43% yield. $^1$H NMR (CDCl$_3$, 600 MHz) δ 7.96 (d, J=7.2 Hz, 2H), 7.71 (d, J=7.8 Hz, 1H), 7.60-7.53 (m, 3H), 7.41 (dd, J=7.8, 7.8 Hz, 1H), 7.37 (dd, J=7.5, 7.5 Hz, 1H), 7.28-7.21 (m, 3H), 7.18 (s, 1H), 7.14 (d, J=7.8 Hz, 1H), 6.73-6.68 (m, 1H), 5.25 (s, 2H), 5.18 (s, 2H), 2.97 (d, J=4.8 Hz, 3H), 2.18 (s, 3H), 2.05 (s, 3H). HRMS (ESI$^+$) calcd for C$_{29}$H$_{28}$F$_3$N$_4$O$_3$ (M+H)$^+$ 537.2114, found 537.2112.

Example 53

Synthesis of 3-((3,5-Dimethyl-4-(4-((4-(trifluoromethyl)phenoxy)-methyl)benzamido)-1H-pyrazol-1-yl)methyl)-N-methylbenzamide (D9c)

Compound D9c was prepared from intermediate IA12 via a displacement reaction by a phenol in a fashion similar to the one described for compound D1. White solid, 7.0 mg, 18% yield. $^1$H NMR (CDCl$_3$, 600 MHz) δ 7.94 (d, J=8.4 Hz, 2H), 7.73 (d, J=7.8 Hz, 1H), 7.56 (d, J=8.4 Hz, 4H), 7.40 (dd, J=8.1, 8.1 Hz, 1H), 7.32 (s, 1H), 7.28 (d, J=7.2 Hz, 1H), 7.17 (s, 1H), 7.04 (d, J=9.0 Hz, 2H), 6.58-6.53 (m, 1H), 5.29 (s, 2H), 5.20 (s, 2H), 3.00 (d, J=4.8 Hz, 3H), 2.21 (s, 3H), 2.09 (s, 3H). HRMS (ESI$^+$) calcd for C$_{29}$H$_{28}$F$_3$N$_4$O$_3$(M+H)$^+$ 537.2114, found 537.2119.

Example 54

Synthesis of 3-((3,5-Dimethyl-4-(4-((2-methyl-4-(trifluoromethyl)phenoxy)-methyl)benzamido)-1H-pyrazol-1-yl)methyl)-N-methylbenzamide (D10)

Compound D10 was prepared from intermediate IA12 via a displacement reaction by a phenol in a fashion similar to the one described for compound D1. White solid, 14 mg, 16% yield. $^1$H NMR (CDCl$_3$, 600 MHz) δ 7.96 (d, J=7.8 Hz, 2H), 7.71 (d, J=7.8 Hz, 1H), 7.56 (d, J=7.2 Hz, 2H), 7.52 (s, 1H), 7.44-7.40 (m, 2H), 7.37 (d, J=7.5, 7.5 Hz, 1H), 7.29-

7.26 (m, 1H), 7.17 (s, 1H), 6.89 (d, J=9.0 Hz, 1H), 6.67 (d, J=3.6 Hz, 1H), 5.26 (s, 2H), 5.21 (s, 2H), 2.97 (d, J=4.8 Hz, 3H), 2.34 (s, 3H), 2.18 (s, 3H), 2.06 (s, 3H). HRMS (ESI$^+$) calcd for $C_{30}H_{30}F_3N_4O_3$ (M+H)$^+$ 551.2270, found 551.2265.

Example 55

Synthesis of N-(1-(3-Acetamidobenzyl)-3,5-dimethyl-1H-pyrazol-4-yl)-4-((4-(trifluoromethyl)phenoxy)methyl)benzamide (D11)

Step 1. Synthesis of N-(3,5-Dimethyl-1-(3-nitrobenzyl)-1H-pyrazol-4-yl)-4-((4-(trifluoromethyl)phenoxy)methyl)benzamide (IA17)

Compound IA17 was prepared from intermediate IA9b and 4-((4-(trifluoromethyl)phenoxy)methyl)benzoic acid via an EDC-mediated amide formation in a fashion similar to the one described for compound A1. Yellow solid, 110 mg, 42% yield. $^1$H NMR (CDCl$_3$, 600 MHz) δ 8.14 (d, J=8.4 Hz, 1H), 7.99 (s, 1H), 7.93 (d, J=7.2 Hz, 2H), 7.60-7.54 (m, 4H), 7.52 (dd, J=7.8, 7.8 Hz, 1H), 7.45 (d, J=7.8 Hz, 1H), 7.28 (s, 1H), 7.03 (d, J=8.4 Hz, 2H), 5.32 (s, 2H), 5.20 (s, 2H), 2.22 (s, 3H), 2.15 (s, 3H). HRMS (ESI$^+$) calcd for $C_{27}H_{24}F_3N_4O_4$ (M+H)$^+$ 525.1744, found 525.1743.

Step 2. Synthesis of N-(1-(3-Acetamidobenzyl)-3,5-dimethyl-1H-pyrazol-4-yl)-4-((4-(trifluoromethyl)phenoxy)methyl)benzamide (D1)

Compound D11 was prepared from intermediate IA17 through a NaBH$_4$/NiCl$_2$-mediated reduction followed by an acetylation reaction in a fashion similar to the one described for compound A7a. White solid, 10 mg, 18% yield. $^1$H NMR (CDCl$_3$, 600 MHz) δ 8.34 (s, 1H), 7.94 (d, J=8.4 Hz, 2H), 7.65 (s, 1H), 7.55 (d, J=8.4 Hz, 2H), 7.51 (d, J=7.8 Hz, 2H), 7.26-7.23 (m, 2H), 7.06 (s, 1H), 7.02 (d, J=8.4 Hz, 2H), 6.89 (d, J=7.2 Hz, 1H), 5.18 (s, 2H), 5.17 (s, 2H), 2.12 (s, 3H), 2.10 (s, 3H), 2.08 (s, 3H). HRMS (ESI$^+$) calcd for $C_{29}H_{28}F_3N_4O_3$ (M+H)$^+$ 537.2114, found 537.2110.

Example 56

Synthesis of N-(1-(3-Acetamidobenzyl)-3,5-dimethyl-1H-pyrazol-4-yl)-4-((2-methyl-4-(trifluoromethyl)phenoxy)methyl)benzamide (D12)

Step 1. Synthesis of 4,4,5,5-Tetramethyl-2-(2-methyl-4-(trifluoromethyl)phenyl)-1,3,2-dioxaborolane (IA14)

A flask charged with Pd(dppf)Cl$_2$ (44 mg, 0.06 mmol), KOAc (589 mg, 6.0 mmol), and bis(pinacolato)diboron (559 mg, 2.2 mmol) was flushed with nitrogen. DMSO (10 mL) and 4-bromo-3-methylbenzotrifluoride (IA13, 280 mg, 2.0 mmol) were then added. After being stirred at 80° C. for 24 h, the reaction mixture was extracted with EtOAc. The organic layer was washed with water and dried over anhydrous Na$_2$SO$_4$. After filtration, the filtrate was concentrated in vacuo and the residue was purified by flash column chromatography (0-50% EtOAc/hexanes) to give compound IA14 as a colorless oil (380 mg, 66%). $^1$H NMR (CDCl$_3$, 600 MHz) δ 7.84 (d, J=7.8 Hz, 1H), 7.42-7.37 (m, 2H), 2.58 (s, 3H), 1.35 (s, 12H).

Step 2. Synthesis of 2-Methyl-4-(trifluoromethyl)phenol (IA15)

To a solution of compound IA14 (380 mg, 1.33 mmol) in EtOH/H$_2$O (2:1, 6 mL) was added mCPBA (252 mg, 1.46 mmol) and the mixture was allowed to stir at rt for 12 h. After the solvents were removed, the residue was diluted with EtOAc (20 mL), H$_2$O (10 mL) and saturated NaHCO$_3$ (10 mL). After separation, the organic layer was washed with brine (20 mL) and concentrated. The residue was purified by flash column chromatography (0-50% EtOAc/hexanes) to give phenol IA15 as a white solid (180 mg, 77%). $^1$H NMR (CDCl$_3$, 600 MHz) δ 7.55 (s, 1H), 7.51 (d, J=7.8 Hz, 1H), 7.19 (d, J=7.8 Hz, 1H), 2.10 (s, 3H). HRMS (ESI) calcd for $C_8H_6F_3O$ (M−H)$^−$ 175.0376, found 175.0378.

Step 3. Synthesis of 4-((2-Methyl-4-(trifluoromethyl)phenoxy)methyl)benzoic Acid (IA16)

To a solution of methyl 4-(bromomethyl)benzoate (IA2b, 220 mg, 0.88 mmol) in DMF (10 mL) was added Cs$_2$CO$_3$ (573 mg, 1.76 mmol) and 2-methyl-4-trifluoromethylphenol (IA15, 170 mg, 0.97 mmol) and the reaction mixture was allowed to stir at 80° C. for 12 h. After cooled to rt, the solution was diluted with saturated NH$_4$Cl and extracted with EtOAc. The organic phase was washed with water, brine, dried over anhydrous Na$_2$SO$_4$, and concentrated in vacuo. The residue was dissolved in MeOH (20 mL) and 1 N NaOH (10 mL). The reaction mixture was allowed to stir at rt for 12 h. Upon removal of MeOH, aqueous phase was acidified with 1 N HCl to pH=3. Aqueous solution was extracted with EtOAc, The organic phase was washed with water, brine, dried over anhydrous Na$_2$SO$_4$, and concentrated in vacuo. The residue was purified by flash column chromatography (0-15% MeOH/CH$_2$Cl$_2$) to afford acid IA16 as a white solid (130 mg, 45% over two steps). $^1$H NMR (DMSO-d$_6$, 600 MHz) δ 7.97 (d, J=8.4 Hz, 2H), 7.58 (d, J=7.2 Hz, 2H), 7.55 (s, 1H), 7.52 (d, J=8.4 Hz, 1H), 7.17 (d, J=7.8 Hz, 1H), 5.31 (s, 2H), 2.29 (s, 3H). HRMS (ESI$^−$) calcd for $C_{16}H_{12}F_3O_3$ (M−H)$^−$ 309.0744, found 309.0739.

Step 4. Synthesis of N-(3,5-Dimethyl-1-(3-nitrobenzyl)-1H-pyrazol-4-yl)-4-((2-methyl-4-(trifluoromethyl)phenoxy)methyl)benzamide (IA18)

Compound IA18 was prepared from intermediate IA9b and 4-((2-methyl-4-(trifluoromethyl)phenoxy)methyl)benzoic acid (IA16) via an EDC-mediated amide formation in a fashion similar to the one described for compound A1. Yellow solid, 75 mg, 50% yield. $^1$H NMR (CDCl$_3$, 600 MHz) δ 8.15 (d, J=8.4 Hz, 1H), 8.00 (s, 1H), 7.94 (d, J=8.4 Hz, 2H), 7.65 (s, 1H), 7.57 (d, J=8.4 Hz, 2H), 7.52 (dd, J=7.8, 7.8 Hz, 1H), 7.46 (d, J=7.8 Hz, 1H), 7.43-7.39 (m, 2H), 7.29 (s, 1H), 7.90 (d, J=8.4 Hz, 1H), 5.33 (s, 2H), 5.22 (s, 2H), 2.34 (s, 3H), 2.22 (s, 3H), 2.16 (s, 3H). HRMS (ESI$^+$) calcd for $C_{28}H_{26}F_3N_4O_4$ (M+H)$^+$ 539.1901, found 539.1906.

Step 5. Synthesis of N-(1-(3-Acetamidobenzyl)-3,5-dimethyl-1H-pyrazol-4-yl)-4-((2-methyl-4-(trifluoromethyl)phenoxy)methyl)benzamide (D12)

Compound D12 was prepared from intermediate IA18 through a NaBH$_4$/NiCl$_2$-mediated reduction followed by an acetylation reaction in a fashion similar to the one described for compound A7a. White solid, 6.0 mg, 14% yield. $^1$H NMR (CDCl$_3$, 600 MHz) δ 8.18 (s, 1H), 7.94 (d, J=8.4 Hz, 2H), 7.64 (d, J=8.4 Hz, 1H), 7.57 (s, 1H), 7.53 (d, J=7.8 Hz, 2H), 7.44-7.37 (m, 2H), 7.26-7.22 (m, 1H), 7.07 (s, 1H), 6.92-6.84 (m, 2H), 5.19 (s, 4H), 2.32 (s, 3H), 2.14 (s, 3H), 2.11 (s, 3H), 2.09 (s, 3H). HRMS (ESI$^+$) calcd for C$_{30}$H$_{30}$F$_3$N$_4$O$_3$ (M+H)$^+$ 551.2270, found 551.2270.

Example 57

Synthesis of 6-((3,5-Dimethyl-4-(4-((4-(trifluoromethyl)phenoxy)methyl)-benzamido-1H-pyrazol-1-yl)methyl)-N-methylpicolinamide (E1a)

Step 1. Synthesis of Methyl 6-((3,5-Dimethyl-4-nitro-1H-pyrazol-1-yl)methyl)picolinate (IE3a)

A solution of IE1a (600 mg, 4.0 mmol), NBS (712 mg, 4.0 mmol) and AIBN (131 mg, 0.8 mmol) in CCl$_4$ (15 mL) was heated at 70° C. for 2 h. After the solvent was evaporated in vacuo, the residue was purified by flash column chromatography (0-50% EtOAc/hexanes) to afford an inseparable mixture of IE2a and IE1a. To a solution of 3,5-dimethyl-4-nitropyrazole (141 mg, 1.0 mmol) and KO$^t$Bu (135 mg, 1.2 mmol) in DMF (5 ml) was added the above mixture and the reaction mixture was allowed to stir rt for 12 h. The reaction was quenched with NH$_4$Cl (sat.) and EtOAc (50 mL) was added. The organic layer was separated, washed with H$_2$O (150 mL) and brine (100 mL), and concentrated in vacuo. The residue was purified by flash column chromatography (0-80% EtOAc/hexanes) to afford compound IE3a as a light yellow oil (230 mg, 79%). $^1$H NMR (CDCl$_3$, 600 MHz) δ 8.08 (d, J=7.8 Hz, 1H), 7.84 (dd, J=7.8, 7.8 Hz, 1H), 7.14 (d, J=7.8 Hz, 1H), 5.49 (s, 2H), 4.02 (s, 3H), 2.63 (s, 3H), 2.55 (s, 3H). HRMS (ESI$^+$) calcd for C$_{13}$H$_{15}$N$_4$O$_4$ (M+H)$^+$ 291.1093, found 291.1098.

Step 2. Synthesis of 6-((3,5-Dimethyl-4-nitro-1H-pyrazol-1-yl)methyl)-N-methylpicolinamide (IE4a)

A solution of methyl ester IE3a (200 mg, 0.69 mmol) in MeNH$_2$/EtOH (5 mL) in a sealed tube was heated at 70° C. for 24 h. After the solvent was evaporated in vacuo, the residue was purified by flash column chromatography (0-15% MeOH/CH$_2$Cl$_2$) to afford compound IE4a as a light yellow solid (130 mg, 65%). $^1$H NMR (CDCl$_3$, 600 MHz) δ 8.16 (d, J=8.4 Hz, 1H), 7.85 (dd, J=8.1, 8.1 Hz, 1H), 7.78 (br s, 1H), 7.17 (d, J=7.8 Hz, 1H), 5.39 (s, 2H), 3.04 (d, J=4.8 Hz, 3H), 2.63 (s, 3H), 2.55 (s, 3H). HRMS (ESI$^+$) calcd for C$_{13}$H$_{16}$N$_5$O$_3$ (M+H)$^+$ 290.1253, found 290.1259.

Step 3. Synthesis of 6-((4-Amino-3,5-dimethyl-1H-pyrazol-1-yl)methyl)-N-methylpicolinamide (IE5a)

To a solution of compound IE4a (130 mg, 0.45 mmol) and NiCl$_2$.6H$_2$O (214 mg, 0.90 mmol) in MeOH (20 mL) was slowly added NaBH$_4$ (68 mg, 1.80 mmol) and the mixture was allowed to stir at rt for 3 h. The reaction was quenched with saturated NH$_4$Cl (50 mL) and the mixture was extracted with EtOAc. The organic phase was washed with water and brine and dried over anhydrous K$_2$CO$_3$. After filtration, the filtrate was concentrated in vacuo and the residue was purified by flash column chromatography (0-15% MeOH/CH$_2$Cl$_2$) to afford compound IE5a as a brown solid (90 mg, 77%). $^1$H NMR (CDCl$_3$, 600 MHz) δ 8.07 (d, J=7.2 Hz, 1H), 7.96 (br s, 1H), 7.74 (dd, J=7.2, 7.2 Hz, 1H), 6.87 (d, J=7.2 Hz, 1H), 5.29 (s, 2H), 3.04 (d, J=4.8 Hz, 3H), 2.31 (s, 3H), 2.08 (s, 3H). HRMS (ESI$^+$) calcd for C$_{13}$H$_{18}$N$_5$O (M+H)$^+$ 260.1511, found 260.1509.

Step 4. Synthesis of 6-((3,5-Dimethyl-4-(4-((4-(trifluoromethyl)phenoxy)methyl)benzamido)-1H-pyrazol-1-yl)methyl)-N-methylpicolinamide (E1a)

Compound E1a was prepared from amine IE5a and a proper carboxylic acid via an amide formation reaction (EDC coupling). White solid (7.5 mg, 9%). $^1$H NMR (CDCl$_3$, 600 MHz) δ 8.09 (d, J=7.8 Hz, 1H), 7.98 (d, J=4.2 Hz, 1H), 7.94 (d, J=8.4 Hz, 2H), 7.79 (dd, J=7.8, 7.8 Hz, 1H), 7.56 (d, J=7.8 Hz, 4H), 7.29 (s, 1H), 7.11 (d, J=7.8 Hz, 1H), 7.04 (d, J=8.4 Hz, 2H), 5.37 (s, 2H), 5.20 (s, 2H), 3.06 (d, J=4.8 Hz, 3H), 2.21 (s, 3H), 2.18 (s, 3H). HRMS (ESI$^+$) calcd for C$_{28}$H$_{27}$F$_3$N$_5$O$_3$(M+H)$^+$ 538.2066, found 538.2063.

Example 58

Synthesis of 6-((3,5-Dimethyl-4-(4-((2-methyl-4-(trifluoromethyl)phenoxy)methyl)benzamido)-1H-pyrazol-1-yl)methyl)-N-methylpicolinamide (E1b)

Compound E1b was prepared from amine IE5a and a proper carboxylic acid via an amide formation reaction (EDC coupling). White solid (17 mg, 40%). $^1$H NMR (CDCl$_3$, 600 MHz) δ 8.10 (d, J=7.8 Hz, 1H), 7.98 (br s, 1H), 7.95 (d, J=8.4 Hz, 2H), 7.80 (dd, J=8.4, 8.4 Hz, 1H), 7.57 (d, J=7.8 Hz, 2H), 7.44-7.39 (m, 2H), 7.26-7.23 (m, 1H), 7.12 (d, J=7.8 Hz, 1H), 6.90 (d, J=8.4 Hz, 1H), 5.38 (s, 2H), 5.22 (s, 2H), 3.06 (d, J=5.4 Hz, 3H), 2.34 (s, 3H), 2.22 (s, 3H), 2.18 (s, 3H). HRMS (ESI$^+$) calcd for C$_{29}$H$_{29}$F$_3$N$_5$O$_3$(M+H)$^+$ 552.2222, found 552.2230.

Example 59

Synthesis of 4-((3,5-Dimethyl-4-(4-((4-(trifluoromethyl)phenoxy)methyl)benzamido)-1H-pyrazol-1-yl)methyl)-N-methylpicolinamide (E2a)

Step 1. Synthesis of Methyl 4-((3,5-Dimethyl-4-nitro-1H-pyrazol-1-yl)methyl)picolinate (IE3b)

Compound IE3b was prepared in a fashion similar to the one described for compound IE3a. White solid (270 mg, 66%). $^1$H NMR (CDCl$_3$, 600 MHz) δ 8.74 (d, J=4.8 Hz, 1H), 7.92 (s, 1H), 7.19 (d, J=3.6 Hz, 1H), 5.34 (s, 2H), 4.02 (s, 3H), 2.58 (s, 3H), 2.55 (s, 3H). HRMS (ESI$^+$) calcd for C$_{13}$H$_{15}$N$_4$O$_4$ (M+H)$^+$ 291.1093, found 291.1098.

Step 2. Synthesis of 4-((3,5-Dimethyl-4-nitro-1H-pyrazol-1-yl)methyl)-N-methylpicolinamide (IE4b)

Compound IE4b was prepared in a fashion similar to the one described for compound IE4a. Whit solid (180 mg, 90%). $^1$H NMR (CDCl$_3$, 600 MHz) δ 8.52 (d, J=4.2 Hz, 1H), 8.01 (s, 1H), 7.98 (br s, 1H), 7.09 (d, J=3.6 Hz, 1H), 5.33 (s, 2H), 3.04 (d, J=5.4 Hz, 3H), 2.56 (s, 3H), 2.55 (s, 3H). HRMS (ESI$^+$) calcd for C$_{13}$H$_{16}$N$_5$O$_3$ (M+H)$^+$ 290.1253, found 290.1248.

Step 3. Synthesis of 4-((4-Amino-3,5-dimethyl-1H-pyrazol-1-yl)methyl)-N-methylpicolinamide (IE5b)

Compound IE5b was prepared in a fashion similar to the one described for compound IE5a. Brown solid (80 mg, 59%). $^1$H NMR (CDCl$_3$, 600 MHz) δ 8.43 (d, J=4.8 Hz, 1H), 7.99 (br s, 1H), 7.93 (s, 1H), 6.95 (d, J=4.8 Hz, 1H), 5.22 (s, 2H), 3.02 (d, J=5.4 Hz, 3H), 2.20 (s, 3H), 2.04 (s, 3H). HRMS (ESI⁺) calcd for $C_{13}H_{18}N_5O$ (M+H)⁺ 260.1511, found 260.1505.

Step 4. Synthesis of 4-((3,5-Dimethyl-4-(4-((4-(trifluoromethyl)phenoxy)methyl)benzamido)-1H-pyrazol-1-yl)methyl)-N-methylpicolinamide (E2a)

Compound E2a was prepared from amine IE5b and a proper carboxylic acid via an amide formation reaction (EDC coupling). White solid (11 mg, 13%). ¹H NMR (CDCl₃, 600 MHz) δ 8.48 (d, J=4.2 Hz, 1H), 8.00 (s, 1H), 7.94 (d, J=8.4 Hz, 2H), 7.91 (s, 1H), 7.56 (d, J=7.8 Hz, 4H), 7.31 (s, 1H), 7.08 (d, J=4.8 Hz, 1H), 7.04 (d, J=8.4 Hz, 2H), 5.30 (s, 2H), 5.20 (s, 2H), 3.02 (d, J=4.8 Hz, 3H), 2.21 (s, 3H), 2.10 (s, 3H). HRMS (ESI⁺) calcd for $C_{28}H_{27}F_3N_5O_3$ (M+H)⁺ 538.2066, found 538.2068.

Example 60

Synthesis of 4-((3,5-Dimethyl-4-(4-((2-methyl-4-(trifluoromethyl)phenoxy)methyl)benzamido)-1H-pyrazol-1-yl)methyl)-N-methylpicolinamide (E2b)

Compound E2b was prepared from amine IE5b and a proper carboxylic acid via an amide formation reaction (EDC coupling). White solid (16 mg, 16%). ¹H NMR (CDCl₃, 600 MHz) δ 8.47 (d, J=4.2 Hz, 1H), 8.01 (d, J=4.8 Hz, 1H), 7.95 (d, J=8.4 Hz, 2H), 7.91 (s, 1H), 7.56 (d, J=7.8 Hz, 2H), 7.44-7.38 (m, 3H), 7.08 (d, J=4.8 Hz, 1H), 6.90 (d, J=8.4 Hz, 1H), 5.29 (s, 2H), 5.21 (s, 2H), 3.02 (d, J=4.8 Hz, 3H), 2.34 (s, 3H), 2.20 (s, 3H), 2.10 (s, 3H). HRMS (ESI⁺) calcd for $C_{29}H_{29}F_3N_5O_3$ (M+H)⁺ 552.2222, found 552.2224.

Example 61

Synthesis of 5-((3,5-Dimethyl-4-(4-((4-(trifluoromethyl)phenoxy)methyl)benzamido)-1H-pyrazol-1-yl)methyl)-N-methylnicotinamide (E3a)

Step 1. Synthesis of Methyl 5-((3,5-Dimethyl-4-nitro-1H-pyrazol-1-yl)methyl)nicotinate (IE3c)

Compound IE3c was prepared in a fashion similar to the one described for compound IE3a. Light yellow oil (230 mg, 79%). ¹H NMR (CDCl₃, 600 MHz) δ 9.19 (s, 1H), 8.67 (s, 1H), 8.12 (s, 1H), 5.33 (s, 2H), 3.97 (s, 3H), 2.63 (s, 3H), 2.54 (s, 3H). HRMS (ESI⁺) calcd for $C_{13}H_{15}N_4O_4$ (M+H)⁺ 291.1093, found 291.1095.

Step 2. Synthesis of 5-((3,5-Dimethyl-4-nitro-1H-pyrazol-1-yl)methyl)-N-methylnicotinamide (IE4c)

Compound IE4c was prepared in a fashion similar to the one described for compound IE4a. White solid (150 mg, 75%). ¹H NMR (CDCl₃, 600 MHz) δ 8.89 (d, J=1.8 Hz, 1H), 8.60 (d, J=1.8 Hz, 1H), 7.97 (s, 1H), 6.21 (br s, 1H), 5.31 (s, 2H), 3.04 (d, J=4.8 Hz, 3H), 2.62 (s, 3H), 2.53 (s, 3H). HRMS (ESI⁺) calcd for $C_{13}H_{16}N_5O_3$ (M+H)⁺ 290.1253, found 290.1260.

Step 3. Synthesis of 5-((4-Amino-3,5-dimethyl-1H-pyrazol-1-yl)methyl)-N-methylnicotinamide (IE5c)

Compound IE5c was prepared in a fashion similar to the one described for compound IE5a. White solid (50 mg, 40%). ¹H NMR (CDCl₃, 600 MHz) δ 8.88 (s, 1H), 8.47 (s, 1H), 7.74 (s, 1H), 6.19 (br s, 1H), 5.25 (s, 2H), 3.10 (d, J=4.2 Hz, 3H), 2.20 (s, 3H), 2.06 (s, 3H). HRMS (ESI⁺) calcd for $C_{13}H_{18}N_5O$ (M+H)⁺ 260.1511, found 260.1511.

Step 4. Synthesis of 5-((3,5-Dimethyl-4-(4-((4-(trifluoromethyl)phenoxy)methyl)benzamido)-1H-pyrazol-1-yl)methyl)-N-methylnicotinamide (E3a)

Compound E3a was prepared from amine IE5c and a proper carboxylic acid via an amide formation reaction (EDC coupling). White solid (30 mg, 48%). ¹H NMR (CDCl₃, 600 MHz) δ 8.97 (s, 1H), 8.60 (s, 1H), 7.94 (d, J=8.4 Hz, 2H), 7.59-7.54 (m, 4H), 7.40 (s, 1H), 7.04 (d, J=9.0 Hz, 2H), 6.71 (br s, 1H), 5.32 (s, 2H), 5.22 (s, 2H), 3.02 (d, J=4.8 Hz, 3H), 2.20 (s, 3H), 2.11 (s, 3H). HRMS (ESI⁺) calcd for $C_{28}H_{27}F_3N_5O_3$ (M+H)⁺ 538.2066, found 538.2061.

Example 62

Synthesis of 5-((3,5-Dimethyl-4-(4-((2-methyl-4-(trifluoromethyl)phenoxy)methyl)benzamido)-1H-pyrazol-1-yl)methyl)-N-methylnicotinamide (E3b)

Compound E3b was prepared from amine IE5c and a proper carboxylic acid via an amide formation reaction (EDC coupling). White solid (38 mg, 59%). ¹H NMR (CDCl₃, 600 MHz) δ 8.97 (s, 1H), 8.60 (s, 1H), 7.95 (d, J=8.4 Hz, 2H), 7.58 (d, J=7.8 Hz, 2H), 7.44-7.35 (m, 4H), 6.90 (d, J=8.4 Hz, 1H), 6.74 (br s, 1H), 5.31 (s, 2H), 5.22 (s, 2H), 3.02 (d, J=4.2 Hz, 3H), 2.34 (s, 3H), 2.20 (s, 3H), 2.11 (s, 3H). HRMS (ESI⁺) calcd for $C_{29}H_{29}F_3N_5O_3$ (M+H)⁺ 552.2222, found 552.2221.

Example 63

Synthesis of 2-((3,5-Dimethyl-4-(4-((4-(trifluoromethyl)phenoxy)methyl)benzamido)-1H-pyrazol-1-yl)methyl)-N-methylisonicotinamide (E4a)

Step 1. Synthesis of Methyl 2-((3,5-Dimethyl-4-nitro-1H-pyrazol-1-yl)methyl)isonicotinate (IE3d)

Compound IE3d was prepared in a fashion similar to the one described for compound IE3a. Light yellow solid (400 mg, 64%). ¹H NMR (CDCl₃, 600 MHz) δ 8.72 (d, J=5.4 Hz, 1H), 7.80 (d, J=4.8 Hz, 1H), 7.68 (s, 1H), 5.43 (s, 2H), 3.96 (s, 3H), 2.66 (s, 3H), 2.53 (s, 3H). HRMS (ESI⁺) calcd for $C_{13}H_{15}N_4O_4$ (M+H)⁺ 291.1093, found 291.1099.

Step 2. Synthesis of 2-((3,5-Dimethyl-4-nitro-1H-pyrazol-1-yl)methyl)-N-methylisonicotinamide (IE4d)

Compound IE4d was prepared in a fashion similar to the one described for compound IE4a. White solid (300 mg, 75%). ¹H NMR (CDCl₃, 600 MHz) δ 8.68 (d, J=4.8 Hz, 1H), 7.53 (d, J=4.8 Hz, 1H), 7.45 (s, 1H), 6.24 (br s, 1H), 5.41 (s, 2H), 3.02 (d, J=5.4 Hz, 3H), 2.65 (s, 3H), 2.53 (s, 3H). HRMS (ESI⁺) calcd for $C_{13}H_{16}N_5O_3$ (M+H)⁺ 290.1253, found 290.1254.

Step 3. Synthesis of 2-((4-Amino-3,5-dimethyl-1H-pyrazol-1-yl)methyl)-N-methylisonicotinamide (IE5d)

Compound IE5d was prepared in a fashion similar to the one described for compound IE5a. Brown oil (150 mg, 55%). $^1$H NMR (CDCl$_3$, 600 MHz) δ 8.62 (d, J=4.8 Hz, 1H), 7.52 (d, J=4.8 Hz, 1H), 7.11 (s, 1H), 6.64 (br s, 1H), 5.30 (s, 2H), 2.95 (d, J=4.8 Hz, 3H), 2.18 (s, 3H), 2.09 (s, 3H). HRMS (ESI$^+$) calcd for C$_{13}$H$_{18}$N$_5$O (M+H)$^+$ 260.1511, found 260.1507.

Step 4. Synthesis of 2-((3,5-Dimethyl-4-(4-((4-(trifluoromethyl)phenoxy)methyl)benzamido)-1H-pyrazol-1-yl)methyl)-N-methylisonicotinamide (E4a)

Compound E4a was prepared from amine IE5d and a proper carboxylic acid via an amide formation reaction (EDC coupling). White solid (10 mg, 16%). $^1$H NMR (CDCl$_3$, 600 MHz) δ 8.67 (d, J=5.4 Hz, 1H), 7.97-7.92 (m, 2H), 7.69 (d, J=4.2 Hz, 1H), 7.60-7.53 (m, 5H), 7.44 (s, 1H), 7.07-7.02 (m, 2H), 6.57 (s, 1H), 5.44 (s, 2H), 5.21 (s, 2H), 3.01 (d, J=4.8 Hz, 3H), 2.22 (s, 3H), 2.17 (s, 3H). HRMS (ESI$^+$) calcd for C$_{28}$H$_{27}$F$_3$N$_5$O$_3$(M+H)$^+$ 538.2066, found 538.2062.

Example 64

Synthesis of 2-((3,5-Dimethyl-4-(4-((2-methyl-4-(trifluoromethyl)phenoxy)methyl)benzamido)-1H-pyrazol-1-yl)methyl)-N-methylisonicotinamide (E4b)

Compound E4b was prepared from amine IE5d and a proper carboxylic acid via an amide formation reaction (EDC coupling). White solid (30 mg, 47%). $^1$H NMR (CDCl$_3$, 600 MHz) δ 8.68 (d, J=4.8 Hz, 1H), 7.95 (d, J=8.4 Hz, 2H), 7.70 (d, J=5.4 Hz, 1H), 7.59 (d, J=8.4 Hz, 2H), 7.44-7.36 (m, 3H), 7.14 (br s, 1H), 6.90 (d, J=8.4 Hz, 1H), 6.55 (s, 1H), 5.44 (s, 2H), 5.23 (s, 2H), 3.01 (d, J=4.2 Hz, 3H), 2.34 (s, 3H), 2.23 (s, 3H), 2.09 (s, 3H). HRMS (ESI$^+$) calcd for C$_{29}$H$_{29}$F$_3$N$_5$O$_3$(M+H)$^+$ 552.2222, found 552.2221.

Example 65

Synthesis of N-(3,5-Dimethyl-1-(3-(methylcarbamoyl)benzyl)-1H-pyrazol-4-yl)-6-((2-methyl-4-(trifluoromethyl)phenoxy)methyl)nicotinamide (E5a)

Step 1. Synthesis of Methyl 6-(Bromomethyl)nicotinate (IE7)

A solution of IE6 (600 mg, 4.0 mmol), NBS (712 mg, 4.0 mmol) and AIBN (131 mg, 0.8 mmol) in CCl$_4$ (15 mL) was heated at 70° C. for 2 h. After the solvent was evaporated in vacuo, the residue was purified by flash column chromatography (0-50% EtOAc/hexanes) to afford an inseparable mixture of IE6 and IE7, which was directly used for next reaction.

Step 2. Synthesis of Methyl 6-((2-Methyl-4-(trifluoromethyl)phenoxy)methyl)nicotinate (IE8)

To a solution of methyl 6-(bromomethyl)nicotinate (IE7, 200 mg, 0.88 mmol) and 2-methyl-4-(trifluoromethyl)phenol (IA15, 170 mg, 0.97 mmol) in DMF (20 mL) was added Cs$_2$CO$_3$ (573 mg, 1.76 mmol) and the mixture was allowed to stir at rt for 12 h. The reaction was quenched with saturated NH$_4$Cl (50 mL) and the mixture was extracted with EtOAc. The organic phase was washed with water and brine and dried over anhydrous Na$_2$SO$_4$. After filtration, the filtrate was concentrated in vacuo and the residue was purified by flash column chromatography (0-50% EtOAc/ hexanes) to afford IE8 as a colorless oil (180 mg, 63%). $^1$H NMR (CDCl$_3$, 600 MHz) δ 9.21 (s, 1H), 8.35 (d, J=7.8 Hz, 1H), 7.62 (d, J=8.4 Hz, 1H), 7.44 (s, 1H), 7.41 (d, J=9.0 Hz, 1H), 6.88 (d, J=9.0 Hz, 1H), 5.32 (s, 2H), 3.97 (s, 3H), 2.39 (s, 3H). HRMS (ESI$^+$) calcd for C$_{16}$H$_{15}$F$_3$NO$_3$ (M+H)$^+$ 326.0999, found 326.1001.

Step 3. Synthesis of 6-((2-Methyl-4-(trifluoromethyl)phenoxy)methyl)nicotinic Acid (IE9)

To a solution of IE8 (180 mg, 0.55 mmol) in MeOH/H$_2$O (20 mL, 2:1) was added NaOH (45 mg, 1.11 mmol) and the mixture was allowed to stir at rt for 12 h. Upon removal of MeOH, the pH of the reaction mixture was adjusted to 5 and the mixture was extracted with EtOAc. The organic phase was washed with water and brine and dried over anhydrous Na$_2$SO$_4$. After filtration, the filtrate was concentrated in vacuo to afford IE9 as a white solid (100 mg, 58%). $^1$H NMR (DMSO-d$_6$, 600 MHz) δ 9.05 (s, 1H), 8.30 (d, J=7.8 Hz, 1H), 7.64 (d, J=8.4 Hz, 1H), 7.56 (s, 1H), 7.52 (d, J=9.0 Hz, 1H), 7.16 (d, J=7.8 Hz, 1H), 5.37 (s, 2H), 3.97 (s, 3H), 2.33 (s, 3H). HRMS (ESI$^-$) calcd for C$_{15}$H$_{21}$N$_4$O (M–H)$^-$ 310.0697, found 310.0697.

Step 4. Synthesis of N-(3,5-Dimethyl-1-(3-(methylcarbamoyl)benzyl)-1H-pyrazol-4-yl)-6-((2-methyl-4-(trifluoromethyl)phenoxy)methyl)nicotinamide (E5a)

Compound E5a was prepared from amine IA11 and IE9 via an amide formation reaction (EDC coupling). White solid (17 mg, 31%). $^1$H NMR (CDCl$_3$, 600 MHz) δ 9.13 (d, J=1.8 Hz, 1H), 8.28 (dd, J=8.4, 1.8 Hz, 1H), 7.70 (d, J=7.8 Hz, 1H), 7.67 (d, J=8.4 Hz, 1H), 7.48-7.37 (m, 4H), 7.28 (d, J=7.2 Hz, 1H), 7.23 (s, 1H), 6.90 (d, J=9.0 Hz, 1H), 6.52-6.48 (m, 1H), 5.34 (s, 2H), 5.28 (s, 2H), 2.99 (d, J=4.8 Hz, 3H), 2.39 (s, 3H), 2.20 (s, 3H), 2.09 (s, 3H). HRMS (ESI$^+$) calcd for C$_{29}$H$_{29}$F$_3$N$_5$O$_3$ (M+H)$^+$ 552.2217, found 552.2224.

Example 66

Synthesis of 4-((3,5-Dimethyl-4-(6-((2-methyl-4-(trifluoromethyl)phenoxy)methyl)nicotinamido)-1H-pyrazol-1-yl)methyl)-N-methylpicolinamide (E5b)

Compound E5b was prepared from amine IE5b and IE9 via an amide formation reaction (EDC coupling). White solid (10 mg, 18%). $^1$H NMR (CDCl$_3$, 600 MHz) δ 9.14 (s, 1H), 8.48 (d, J=4.8 Hz, 1H), 8.29 (d, J=7.8 Hz, 1H), 8.04-7.98 (m, 1H), 7.86 (s, 1H), 7.66 (d, J=7.8 Hz, 1H), 7.55 (s, 1H), 7.45 (s, 1H), 7.42 (d, J=7.8 Hz, 1H), 7.10 (d, J=4.2 Hz, 1H), 6.90 (d, J=9.0 Hz, 1H), 5.33 (s, 2H), 5.30 (s, 2H), 3.02 (d, J=5.4 Hz, 3H), 2.39 (s, 3H), 2.21 (s, 3H), 2.11 (s, 3H). HRMS (ESI$^+$) calcd for C$_{28}$H$_{28}$F$_3$N$_6$O$_3$(M+H)$^+$ 553.2175, found 553.2178.

Example 67

Synthesis of 3-((3,5-Dimethyl-4-(4-phenoxybenzamido)-1H-pyrazol-1-yl)methyl)-N-methylbenzamide (E6a)

Compound E6a was prepared from amine IA11 and 4-phenoxylbenzoic acid via an amide formation reaction (EDC coupling). White solid (20 mg, 46%). $^1$H NMR (CDCl$_3$, 600 MHz) δ 7.91 (d, J=8.8 Hz, 2H), 7.71 (d, J=7.6

Hz, 1H), 7.54 (s, 1H), 7.39 (dd, J=7.9, 7.9 Hz, 2H), 7.36 (dd, J=7.6, 7.6 Hz, 1H), 7.25 (d, J=7.6 Hz, 1H), 7.19 (dd, J=7.3, 7.3 Hz, 1H), 7.15 (s, 1H), 7.07 (d, J=8.2 Hz, 2H), 7.05 (d, J=8.9 Hz, 2H), 6.78-6.73 (m, 1H), 5.24 (s, 2H), 2.95 (d, J=4.8 Hz, 3H), 2.16 (s, 3H), 2.04 (s, 3H). HRMS (ESI$^+$) calcd for $C_{27}H_{27}N_4O_3$ (M+H)$^+$ 455.2078, found 455.2077.

Example 68

Synthesis of 3-((3,5-Dimethyl-4-(4-(4-(trifluoromethyl)phenoxy)-benzamido-1H-pyrazol-1-yl)methyl)-N-methylbenzamide (E6b)

Compound E6b was prepared from amine IA11 and 4-(4-(trifluoromethyl)phenoxyl)benzoic acid via an amide formation reaction (EDC coupling). White solid (5 mg, 12%). $^1$H NMR (CDCl$_3$, 600 MHz) δ 8.08 (d, J=9.0 Hz, 2H), 7.76-7.71 (m, 1H), 7.64 (d, J=8.4 Hz, 2H), 7.41-7.36 (m, 2H), 7.28 (d, J=7.2 Hz, 1H), 7.19 (s, 1H), 7.13 (d, J=8.4 Hz, 4H), 6.64-6.59 (m, 1H), 5.28 (s, 2H), 2.99 (d, J=4.8 Hz, 3H), 2.20 (s, 3H), 2.08 (s, 3H). HRMS (ESI$^+$) calcd for $C_{28}H_{26}F_3N_4O_3$(M+H)$^+$ 523.1957, found 523.1954.

Example 69

Synthesis of 3-((3,5-Dimethyl-4-(4-(2-methyl-4-(trifluoromethyl)phenoxy)benzamido)-1H-pyrazol-1-yl)methyl)-N-methylbenzamide (E6c)

Step 1. Synthesis of Methyl 4-(2-Methyl-4-(trifluoromethyl)phenoxy)benzoate (IE12)

A mixture of phenol IE10 (608 mg, 4.0 mmol), bromide IE11 (956 mg, 4.0 mmol), CuI (152 mg, 0.80 mmol), picolinic acid (197 mg, 1.60 mmol), and K$_3$PO$_4$ (2.55 g, 12.0 mmol) in DMSO (10 mL) in a sealed tube was evacuated and backfilled with argon. The reaction mixture was heated at 90° C. for 24 h and then diluted with EtOAc (10 mL) and water (1 mL), and the aqueous layer was extracted with EtOAc (2×10 mL). The combined organic layer was dried over Na$_2$SO$_4$ and concentrated, and the residue was purified by flash column chromatography (0-30% EtOAc/hexanes) to afford IE12 as a colorless oil (100 mg, 8%). $^1$H NMR (CDCl$_3$, 600 MHz) δ 8.02 (d, J=8.4 Hz, 2H), 7.55 (s, 1H), 7.46 (d, J=8.4 Hz, 1H), 7.01 (d, J=7.8 Hz, 1H), 6.94 (d, J=9.0 Hz, 2H), 3.91 (s, 3H), 2.28 (s, 3H).

Step 2. Synthesis of 4-(2-Methyl-4-(trifluoromethyl)phenoxy)benzoic Acid (IE13)

To a solution of IE12 (100 mg, 0.32 mmol) in MeOH/H$_2$O (20 mL, 2:1) was added NaOH (26 mg, 0.64 mmol) and the mixture was allowed to stir at rt for 12 h. Upon removal of MeOH, the pH of the reaction mixture was adjusted to 5 and the mixture was extracted with EtOAc. The organic phase was washed with water and brine, dried over anhydrous Na$_2$SO$_4$. After filtration, the filtrate was concentrated in vacuo to afford IE13 as a white solid (80 mg, 84%). $^1$H NMR (DMSO-d$_6$, 600 MHz) δ 7.96 (d, J=9.0 Hz, 2H), 7.76 (s, 1H), 7.60 (d, J=8.4 Hz, 1H), 7.13 (d, J=8.4 Hz, 1H), 7.03 (d, J=8.4 Hz, 2H), 2.28 (s, 3H). HRMS (ESI$^-$) calcd for $C_{15}H_{21}N_4O$ (M−H)$^-$ 295.0588, found 295.0587.

Step 3. Synthesis of 3-((3,5-Dimethyl-4-(4-(2-methyl-4-(trifluoromethyl)phenoxy)-benzamido)-1H-pyrazol-1-yl)methyl)-N-methylbenzamide (E6c)

Compound E6b was prepared from amine IA11 and IE13 via an amide formation reaction (EDC coupling). White solid (36 mg, 67%). $^1$H NMR (CDCl$_3$, 600 MHz) δ 7.94 (d, J=9.0 Hz, 2H), 7.69 (d, J=7.2 Hz, 1H), 7.56 (s, 1H), 7.46 (d, J=7.8 Hz, 1H), 7.35 (dd, J=7.2, 7.2 Hz, 1H), 7.17 (s, 1H), 7.11 (dd, J=8.4, 8.4 Hz, 1H), 7.00 (dd, J=8.4, 2.4 Hz, 2H), 6.83 (br s, 1H), 5.22 (s, 2H), 2.94 (d, J=4.8 Hz, 3H), 2.30 (s, 3H), 2.15 (s, 3H), 2.03 (s, 3H). HRMS (ESI$^+$) calcd for $C_{29}H_{28}F_3N_4O_3$(M+H)$^+$ 537.2114, found 537.2118.

Example 70

Synthesis of 4-((3,5-Dimethyl-4-(4-(4-(trifluoromethyl)phenoxy)-benzamido)-1H-pyrazol-1-yl)methyl)-N-methylpicolinamide (E7a)

Compound E7a was prepared from amine IE5b and 4-(4-(trifluoromethyl)phenoxyl)benzoic acid via an amide formation reaction (EDC coupling). White solid (20 mg, 38%). $^1$H NMR (CDCl$_3$, 600 MHz) δ 8.47 (d, J=4.2 Hz, 1H), 8.04-7.98 (m, 1H), 7.95 (d, J=9.0 Hz, 2H), 7.90 (s, 1H), 7.64 (d, J=9.0 Hz, 2H), 7.34 (s, 1H), 7.13 (d, J=9.0 Hz, 4H), 7.09 (d, J=4.8 Hz, 1H), 5.30 (s, 2H), 3.02 (d, J=5.4 Hz, 3H), 2.21 (s, 3H), 2.10 (s, 3H). HRMS (ESI$^+$) calcd for $C_{27}H_{25}F_3N_5O_3$ (M+H)$^+$ 524.1909, found 524.1913.

Example 71

Synthesis of 4-((3,5-Dimethyl-4-(4-(2-methyl-4-(trifluoromethyl)phenoxy)-benzamido)-1H-pyrazol-1-yl)methyl)-N-methylpicolinamide (E7b)

Compound E7b was prepared from amine IE5b and IE13 via an amide formation reaction (EDC coupling). White solid (14 mg, 26%). $^1$H NMR (CDCl$_3$, 600 MHz) δ 8.47 (d, J=4.8 Hz, 1H), 8.04-7.98 (m, 1H), 7.91 (d, J=8.4 Hz, 2H), 7.87 (s, 1H), 7.56 (s, 1H), 7.46 (d, J=7.8 Hz, 1H), 7.34 (s, 1H), 7.09 (d, J=4.2 Hz, 1H), 7.03-6.99 (m, 3H), 5.30 (s, 2H), 3.01 (d, J=4.8 Hz, 3H), 2.31 (s, 3H), 2.20 (s, 3H), 2.10 (s, 3H). HRMS (ESI$^+$) calcd for $C_{28}H_{27}F_3N_5O_3$(M+H)$^+$ 538.2066, found 538.2069.

Example 72

Synthesis of 3-((3,5-Dimethyl-4-(4-(1-phenoxyethyl)benzamido)-1H-pyrazol-1-yl)methyl)-N-methylbenzamide (F1)

To a solution of 4-(1-phenoxyethyl)benzoic acid (40 mg, 0.165 mmol), HBTU (53.7 mg, 0.142 mmol) and DIPEA (61 mg, 0.472 mmol) in DMF (5 mL) was added IA11 (35 mg, 0.136 mmol), and the mixture was allowed to stir at rt overnight. The reaction mixture was diluted with EtOAc (50 mL), washed successively with 1N HCl (15 mL), sat. NaHCO$_3$ (15 mL) and brine (15 mL), dried over Na$_2$SO$_4$. After filtration, the filtrate was concentrated in vacuo and the residue was purified by column chromatography (5% MeOH/CH$_2$Cl$_2$) to provide product F1 as a white solid (26.6 mg, 41%). $^1$H NMR (CDCl$_3$, 600 MHz) δ 7.88 (d, J=8.3 Hz, 2H), 7.71 (d, J=7.6 Hz, 1H), 7.50 (d, J=8.2, 2H), 7.44 (s, 1H), 7.36 (t, J=7.6 Hz, 1H), 7.26-7.24 (m, 1H), 7.22-7.18 (m, 2H), 7.15 (s, 1H), 6.89 (t, J=7.3 Hz, 1H), 6.85 (d, J=7.6 Hz, 2H), 6.69-6.64 (m, 1H), 5.38 (q, J=6.4 Hz, 1H), 5.25 (s, 2H), 2.97 (d, J=4.7 Hz, 3H), 2.16 (s, 3H), 2.04 (s, 3H), 1.66 (d, J=7.0 Hz, 3H). HRMS (ESI$^+$) calcd for $C_{29}H_{31}N_4O_3$ (M+H)$^+$ 483.2396, found 483.2380.

Example 73

Synthesis of 3-(1-(3,5-Dimethyl-4-(4-(phenoxymethyl)benzamido)-1H-pyrazol-1-yl)ethyl)-N-methylbenzamide (F2)

Step 1. Synthesis of Methyl 3-(1-Hydroxyethyl)benzoate (IF3a)

To a solution of compound IF2a (440 mg, 2.5 mmol) in MeOH (25 mL) was slowly added NaBH$_4$ (211 mg, 5.6 mmol) and the mixture was allowed to stir at rt for 2 h. The reaction was quenched with saturated NH$_4$Cl (50 mL) and the mixture was extracted with EtOAc. The organic phase was washed with water and brine, dried over anhydrous Na$_2$SO$_4$, and concentrated in vacuo. The residue was purified by flash column chromatography (0-80% EtOAc/hexanes) to afford compound IF3a as a white solid (400 mg, 90%). $^1$H NMR (CDCl$_3$, 600 MHz) δ 8.03 (s, 1H), 7.93 (d, J=7.8 Hz, 1H), 7.58 (d, J=7.8 Hz, 1H), 7.41 (dd, J=7.8, 7.8 Hz, 1H), 4.95-4.91 (m, 1H), 3.91 (s, 3H), 1.50 (d, J=7.8 Hz, 3H).

Step 2. Synthesis of Methyl 3-(1-(3,5-Dimethyl-4-nitro-1H-pyrazol-1-yl)ethyl)benzoate (IF4a)

To a solution of compound IF3a (100 mg, 0.56 mmol), 3,5-dimethyl-4-nitropyrazole (86 mg, 0.61 mmol) and PPh$_3$ (176 mg, 0.67 mmol) in THF (40 mL) was slowly added DEAD (116 mg, 0.67 mmol) and the mixture was allowed to stir at rt for 12 h. The reaction was quenched with saturated NH$_4$Cl (50 mL) and the mixture was extracted with EtOAc. The organic phase was washed with water and brine, dried over anhydrous Na$_2$SO$_4$, and concentrated in vacuo. The residue was purified by flash column chromatography (0-50% EtOAc/hexanes) to afford IF4a as a colorless oil (50 mg, 29%). $^1$H NMR (CDCl$_3$, 600 MHz) δ 7.97 (d, J=7.2 Hz, 1H), 7.91 (s, 1H), 7.42 (dd, J=7.2, 7.2 Hz, 1H), 7.36 (d, J=7.2 Hz, 1H), 5.46 (q, J=7.2 Hz, 1H), 3.92 (s, 3H), 2.56 (s, 3H), 2.55 (s, 3H), 1.93 (d, J=7.2 Hz, 3H). HRMS (ESI$^+$) calcd for $C_{15}H_{18}N_3O_4$ (M+H)$^+$ 304.1292, found 304.1294.

Step 3. Synthesis of 3-(1-(3,5-Dimethyl-4-nitro-1H-pyrazol-1-yl)ethyl)-N-methylbenzamide (IF5a)

A solution of methyl ester IF4a (50 mg, 0.17 mmol) in MeNH$_2$/EtOH (5 mL) in a sealed tube was heated at 70° C. for 24 h. After the solvent was evaporated in vacuo, the residue was purified by flash column chromatography (0-15% MeOH/CH$_2$Cl$_2$) to afford compound IF5a as a white solid (40 mg, 80%). $^1$H NMR (CDCl$_3$, 600 MHz) δ 7.71 (s, 1H), 7.63 (d, J=7.8 Hz, 1H), 7.38 (dd, J=7.8, 7.8 Hz, 1H), 7.29 (d, J=7.8 Hz, 1H), 6.28 (br s, 1H), 5.46 (q, J=7.2 Hz, 1H), 3.00 (d, J=4.8 Hz, 3H), 2.54 (s, 3H), 2.54 (s, 3H), 1.92 (d, J=7.2 Hz, 3H). HRMS (ESI$^+$) calcd for $C_{15}H_{19}N_4O_3$ (M+H)$^+$ 303.1452, found 303.1460.

Step 4. Synthesis of 3-(1-(4-Amino-3,5-dimethyl-1H-pyrazol-1-yl)ethyl)-N-methylbenzamide (IF6a)

To a solution of compound IF5a (40 mg, 0.13 mmol) and NiCl$_2$.6H$_2$O (62 mg, 0.26 mmol) in MeOH (10 mL) was slowly added NaBH$_4$ (20 mg, 0.52 mmol) and the mixture was allowed to stir at rt for 3 h. The reaction was quenched with saturated NH$_4$Cl (50 mL) and the mixture was extracted with EtOAc. The organic phase was washed with water and brine, dried over anhydrous K$_2$CO$_3$, and concentrated in vacuo. The residue was purified by flash column chromatography (0-15% MeOH/CH$_2$Cl$_2$) to afford compound IF6a as a brown solid (30 mg, 85%). $^1$H NMR (CDCl$_3$, 600 MHz) δ 7.60 (d, J=7.2 Hz, 1H), 7.53 (s, 1H), 7.39 (dd, J=7.2, 7.2 Hz, 1H), 7.17 (d, J=7.2 Hz, 1H), 6.15 (br s, 1H), 5.33 (q, J=7.2 Hz, 1H), 2.99 (d, J=4.8 Hz, 3H), 2.22 (s, 3H), 1.99 (s, 3H), 1.88 (d, J=7.2 Hz, 3H). HRMS (ESI$^+$) calcd for $C_{15}H_{21}N_4O$ (M+H)$^+$ 273.1710, found 273.1709.

Step 5. Synthesis of 3-(1-(3,5-Dimethyl-4-(4-(phenoxymethyl)benzamido)-1H-pyrazol-1-yl)ethyl)-N-methylbenzamide (F2)

Compound F2 was prepared from amine IF6a and 4-phenoxylbenzoic acid via an amide formation reaction (HBTU coupling) Yellow oil (50 mg, 40%). $^1$H NMR (CDCl$_3$, 600 MHz) δ 7.91 (d, J=7.7 Hz, 2H), 7.69 (d, J=7.7 Hz, 1H), 7.56 (d, 8.2 Hz, 2H), 7.37 (t, J=7.7 Hz, 1H), 7.33 (s, 1H), 7.32-7.28 (m, 3H), 7.08 (s, 1H), 7.00-6.96 (m, 3H), 6.62-6.57 (m, 1H), 5.42 (q, J=7.0 Hz, 1H), 5.15 (s, 2H), 2.98 (d, J=4.7 Hz, 3H), 2.22 (s, 3H), 2.00 (s, 3H), 1.95 (d, J=7.0 Hz, 3H). HRMS (ESI$^+$) calcd for $C_{29}H_{31}N_4O_3$ (M+H)$^+$ 483.2396, found 483.2383.

Example 74

Synthesis of 3-(1-(3,5-Dimethyl-4-(4-((2-methyl-4-(trifluoromethyl)phenoxy)methyl)benzamido)-1H-pyrazol-1-yl)ethyl)-N-methylbenzamide (F3)

Compound F3 was prepared from amine IF6a and IE9 via an amide formation reaction (EDC coupling). White solid (30 mg, 53%). $^1$H NMR (DMSO-d$_6$, 600 MHz) δ 9.52 (s, 1H), 8.42 (d, J=4.2 Hz, 1H), 7.97 (d, J=8.4 Hz, 2H), 7.73 (s, 1H), 7.69 (d, J=7.8 Hz, 1H), 7.58 (d, J=7.8 Hz, 2H), 7.54 (s, 1H), 7.52 (d, J=7.8 Hz, 1H), 7.40 (dd, J=7.8, 7.8 Hz, 1H), 7.29 (d, J=6.6 Hz, 1H), 7.18 (d, J=8.4 Hz, 1H), 5.58 (q, J=6.6 Hz, 1H), 5.31 (s, 2H), 2.77 (d, J=4.2 Hz, 3H), 2.28 (s, 3H), 2.06 (s, 3H), 2.03 (s, 3H), 1.80 (d, J=7.2 Hz, 3H). HRMS (ESI$^+$) calcd for $C_{31}H_{32}F_3N_4O_3$(M+H)$^+$ 565.2427, found 565.2428.

Example 75

Synthesis of 4-(1-(3,5-Dimethyl-4-(4-((2-methyl-4-(trifluoromethyl)phenoxy)methyl)benzamido)-1H-pyrazol-1-yl)ethyl)-N-methylpicolinamide (F4)

Step 1. Synthesis of Ethyl 4-Acetylpicolinate (IF2b)

Aqueous H$_2$O$_2$ (30%, 43 mL, 400 mmol) was added dropwise to ethyl pyruvate (72 g, 620 mmol) at 0° C. with stirring. The resulting solution was added dropwise to a mixture of 4-acetylpyridine (IF1, 5.0 g, 40 mmol), concentrated H$_2$SO$_4$ (6.3 mL), and FeSO$_4$.7H$_2$O (11.5 g, 120 mmol) in CH$_2$Cl$_2$ (500 mL)/H$_2$O (30 mL) at rt over a period of 1 h. After the mixture was allowed to stir for additional 30 min, the organic phase was separated and the aqueous layer was extracted with CH$_2$Cl$_2$. The combined organic phase was washed with water, brine, dried over anhydrous Na$_2$SO$_4$, and concentrated in vacuo. The residue was purified by flash column chromatography (0-50% EtOAc/hexanes) to afford compound IF2b as a white solid (1.10 g, 14%). $^1$H NMR (CDCl$_3$, 600 MHz) δ 8.96 (d, J=4.8 Hz, 1H), 8.54 (s, 1H), 7.93 (dd, J=4.2, 1.8 Hz, 1H), 4.53 (q, J=7.2 Hz, 2H), 2.70 (s, 3H), 1.48 (d, J=7.2 Hz, 3H). HRMS (ESI$^+$) calcd for C$_{10}$H$_{12}$NO$_3$ (M+H)$^+$ 194.0812, found 194.0809.

Step 2. Synthesis of Methyl 4-(1-Hydroxyethyl)picolinate (IF3b)

To a solution of compound IF2b (1.10 g, 5.7 mmol) in MeOH (50 mL) was slowly added NaBH$_4$ (430 mg, 11.4 mmol) and the mixture was allowed to stir at rt for 2 h. The reaction was quenched with saturated NH$_4$Cl (50 mL) and the mixture was extracted with EtOAc. The organic phase was washed with water and brine, dried over anhydrous Na$_2$SO$_4$, and concentrated in vacuo. The residue was purified by flash column chromatography (0-80% EtOAc/hexanes) to afford compound IF3b as a white solid (850 mg, 76%). $^1$H NMR (CDCl$_3$, 600 MHz) δ 8.71 (d, J=4.2 Hz, 1H), 8.14 (s, 1H), 7.52 (d, J=4.8 Hz, 1H), 5.00 (q, J=6.6 Hz, 1H), 4.02 (s, 3H), 1.54 (d, J=6.6 Hz, 3H). HRMS (ESI$^+$) calcd for C$_9$H$_{12}$NO$_3$ (M+H)$^+$ 182.0812, found 182.0815.

Step 3. Synthesis of 4-(1-(3,5-Dimethyl-4-nitro-1H-pyrazol-1-yl)ethyl)-N-methylpicolinamide (IF5b)

To a solution of compound IF3b (850 g, 4.35 mmol), 3,5-dimethyl-4-nitropyrazole (675 mg, 4.79 mmol) and PPh$_3$ (1.37 g, 5.22 mmol) in THF (40 mL) was slowly added DEAD (1.05 g, 5.22 mmol) and the mixture was allowed to stir at rt for 12 h. The reaction was quenched with saturated NH$_4$Cl (50 mL) and the mixture was extracted with EtOAc. The organic phase was washed with water and brine, dried over anhydrous Na$_2$SO$_4$, and concentrated in vacuo. The residue was purified by flash column chromatography (0-20% MeOH/CH$_2$Cl$_2$) to afford the coupling product as a yellow solid (280 mg, 19%). The resulting methyl ester (280 mg, 0.84 mmol) was dissolved in MeNH$_2$/EtOH (5 mL) in a sealed tube and heated at 70° C. for 24 h. After the solvent was evaporated in vacuo, the residue was purified by flash column chromatography (0-15% MeOH/CH$_2$Cl$_2$) to afford compound IF5b as a white solid (100 mg, 37%). $^1$H NMR (CDCl$_3$, 600 MHz) δ 8.50 (d, J=4.8 Hz, 1H), 8.07 (s, 1H), 8.00 (br s, 1H), 7.13 (d, J=5.4 Hz, 1H), 5.47 (q, J=7.2 Hz, 1H), 3.04 (d, J=5.4 Hz, 3H), 2.56 (s, 3H), 2.54 (s, 3H), 1.94 (d, J=7.2 Hz, 3H). HRMS (ESI$^+$) calcd for C$_{14}$H$_{18}$N$_5$O$_3$ (M+H)$^+$ 304.1404, found 304.1405.

Step 4. Synthesis of 4-(1-(4-Amino-3,5-dimethyl-1H-pyrazol-1-yl)ethyl)-N-methylpicolinamide (IF6b)

To a solution of compound IF5b (100 mg, 0.31 mmol) and NiCl$_2$·6H$_2$O (147 mg, 0.62 mmol) in MeOH (20 mL) was slowly added NaBH$_4$ (50 mg, 1.24 mmol) and the mixture was allowed to stir at rt for 3 h. The reaction was quenched with saturated NH$_4$Cl (50 mL) and the mixture was extracted with EtOAc. The organic phase was washed with water and brine, dried over anhydrous K$_2$CO$_3$, and concentrated in vacuo. The residue was purified by flash column chromatography (0-15% MeOH/CH$_2$Cl$_2$) to afford compound IF6b as a brown oil (60 mg, 70%). $^1$H NMR (CDCl$_3$, 600 MHz) δ 8.40 (d, J=4.8 Hz, 1H), 8.03-7.95 (m, 2H), 6.93 (d, J=5.4 Hz, 1H), 5.33 (q, J=7.2 Hz, 1H), 3.03 (d, J=5.4 Hz, 3H), 2.22 (s, 3H), 2.00 (s, 3H), 1.90 (d, J=7.2 Hz, 3H). HRMS (ESI$^+$) calcd for C$_{14}$H$_{20}$N$_5$O (M+H)$^+$ 274.1662, found 274.1668.

Step 5. Synthesis of 4-(1-(3,5-Dimethyl-4-((2-methyl-4-(trifluoromethyl)phenoxy)methyl)benzamido)-1H-pyrazol-1-yl)ethyl)-N-methylpicolinamide (F4)

Compound F4 was prepared from amine IF6b and IE9 via an amide formation reaction (EDC coupling). White solid (15 mg, 13%). $^1$H NMR (CDCl$_3$, 600 MHz) δ 8.45 (d, J=4.8 Hz, 1H), 8.12 (d, J=7.8 Hz, 1H), 8.04-8.00 (m, 1H), 7.98 (s, 1H), 7.93 (d, J=7.8 Hz, 2H), 7.58-7.52 (m, 2H), 7.44-7.39 (m, 2H), 7.10 (dd, J=4.8, 1.8 Hz, 1H), 6.89 (d, J=8.4 Hz, 1H), 5.41 (q, J=7.2 Hz, 1H), 5.21 (s, 2H), 3.03 (d, J=5.4 Hz, 3H), 2.34 (s, 3H), 2.23 (s, 3H), 2.06 (s, 3H), 1.95 (d, J=7.2 Hz, 3H). HRMS (ESI$^+$) calcd for C$_{30}$H$_{31}$F$_3$N$_5$O$_3$(M+H)$^+$ 566.2374, found 566.2375.

Example 76

Synthesis of 3-((3,5-Dimethyl-4-(4-((pyridin-2-yloxy)methyl)benzamido)-1H-pyrazol-1-yl)methyl)-N-methylbenzamide (G1)

Compound G1 was prepared from intermediate IA12 via a displacement reaction in a fashion similar to the one described for compound D1. Colorless semi solid, 6.0 mg, 1% yield. $^1$H NMR (CDCl$_3$, 600 MHz) δ 7.89 (d, J=8.4 Hz, 2H), 7.72 (d, J=7.8 Hz, 1H), 7.66 (s, 1H), 7.41-7.32 (m, 4H), 7.30 (d, J=6.6 Hz, 1H), 7.26 (s, 1H), 7.18 (s, 1H), 6.69 (s, 1H), 6.60 (d, J=9.0 Hz, 1H), 6.20 (dd, J=6.9, 6.9 Hz, 1H), 5.26 (s, 2H), 5.20 (s, 2H), 2.97 (d, J=4.8 Hz, 3H), 2.16 (s, 3H), 2.05 (s, 3H). HRMS (ESI$^+$) calcd for C$_{27}$H$_{28}$N$_5$O$_3$ (M+H)$^+$470.2192, found 470.2194.

Example 77

Synthesis of 3-((3,5-Dimethyl-4-(4-((pyridin-3-yloxy)methyl)benzamido)-1H-pyrazol-1-yl)methyl)-N-methylbenzamide (G2)

Compound G2 was prepared from intermediate IA12 via a displacement reaction in a fashion similar to the one described for compound D1. White solid, 13 mg, 38% yield. $^1$H NMR (CDCl$_3$, 600 MHz) δ 8.28 (d, J=1.8 Hz, 1H), 8.25 (d, J=3.6 Hz, 1H), 7.96 (d, J=8.4 Hz, 2H), 7.71 (d, J=7.8 Hz, 1H), 7.66 (s, 1H), 7.55 (d, J=7.2 Hz, 2H), 7.37 (d, J=7.5, 7.5 Hz, 1H), 7.26-7.32 (m, 3H), 7.18 (s, 1H), 6.74-6.68 (m, 1H), 5.25 (s, 2H), 5.20 (s, 2H), 2.97 (d, J=4.8 Hz, 3H), 2.17 (s, 3H), 2.05 (s, 3H). HRMS (ESI$^+$) calcd for C$_{27}$H$_{28}$N$_5$O$_3$ (M+H)$^+$470.2192, found 470.2196.

Example 78

Synthesis of 3-((3,5-Dimethyl-4-(4-((pyridin-4-yloxy)methyl)benzamido)-1H-pyrazol-1-yl)methyl)-N-methylbenzamide (G3)

Compound G3 was prepared from intermediate IA12 via a displacement reaction in a fashion similar to the one described for compound D1. White solid, 6 mg, 17% yield. $^1$H NMR (CDCl$_3$, 600 MHz) δ 8.45 (d, J=5.4 Hz, 2H), 7.95 (d, J=8.4 Hz, 2H), 7.72 (d, J=7.8 Hz, 1H), 7.55 (d, J=7.2 Hz, 2H), 7.44 (s, 1H), 7.39 (dd, J=7.8, 7.8 Hz, 1H), 7.29-7.26 (m, 1H), 7.18 (s, 1H), 7.88 (d, J=6.0 Hz, 2H), 6.61-6.55 (m, 1H), 5.28 (s, 2H), 5.20 (s, 2H), 2.99 (d, J=4.8 Hz, 3H), 2.20 (s, 3H), 2.07 (s, 3H). HRMS (ESI+) calcd for $C_{27}H_{28}N_5O_3$ (M+H)+ 470.2192, found 470.2195.

Example 79

Cell Viability Assay

MIA PaCa-2 cells (CRL-1420, ATCC) were maintained in DMEM media supplemented with 10% FBS, 2.5% HS, 1% GlutaMAX, 1% sodium pyruvate, 100 U/mL penicillin, and 100 μg/mL streptomycin. Cell culture media and additives were purchased from Gibco. Cells were plated in 96-well plates at |1–2.5|×10$^4$ cells per well in the DMEM growth media. One microliter of a 2-fold serially diluted compound solution in DMSO (Sigma) starting at 20 mM (100 μM final concentration) was added to each well. The final volume in each well was 200 μL, yielding a final DMSO concentration of 0.5%. Control wells contained 0.5% DMSO (100% viability) or 25% DMSO (background) and all reactions were done in triplicate. The plate was incubated for 72 h at 37° C. in a 5% CO$_2$/95% air humidified atmosphere.

Measurement of cell viability was carried out using a modified method of Mosmann based on 3-(4,5-dimethylthiazol-2-yl)-2,5-diphenyltetrazolium bromide (MTT, Sigma). MTT solution was prepared fresh at 1 mg/mL in serum-free and phenol red-free RPMI 1640 media. After 200 μL of MTT solution was added to each well, the plate was incubated as described above for 3 h. The MTT solution was removed, and the formazan crystals were solubilized with 200 μL of isopropanol. The plate was read on a SpectraMax i3 spectrophotometer (Molecular Devices) at 570 nm for formazan and 650 nm for background subtraction. $EC_{50}$ values were calculated by fitting the data in GraphPad Prism software. $EC_{50}$ values were determined in triplicate. Results are demonstrated in Tables 1-9.

TABLE 1

Antiproliferative activity.

| Compound | R$^1$ | R$^2$ | R$^3$ | EC$_{50}$ MIA PaCa-2 (μM) |
|---|---|---|---|---|
| A1 | H | H | H | 10 |
| A2a | C(O)NH$_2$ | H | H | >100 |
| A2b | H | C(O)NH$_2$ | H | 9.2 |
| A2c | H | H | C(O)NH$_2$ | 42 |
| A3a | C(O)NHMe | H | H | 12 |
| A3b | H | C(O)NHMe | H | 6.2 |
| A3c | H | H | C(O)NHMe | 7.7 |
| A4a | H | C(O)N(Me)$_2$ | H | 6.4 |
| A4b | H | C(O)NHEt | H | 11 |
| A4c | H | C(O)NH$^i$Pr | H | 8.9 |
| A4d | H | C(O)NHPh | H | 6.4 |
| A5a | NO$_2$ | H | H | 7.8 |

TABLE 1-continued

Antiproliferative activity.

| Compound | R$^1$ | R$^2$ | R$^3$ | EC$_{50}$ MIA PaCa-2 (μM) |
|---|---|---|---|---|
| A5b | H | NO$_2$ | H | 11 |
| A5c | H | H | NO$_2$ | 6.0 |
| A6a | NH$_2$ | H | H | >100 |
| A6b | H | NH$_2$ | H | 35 |
| A6c | H | H | NH$_2$ | 11 |
| A7a | NHC(O)Me | H | H | 50 |
| A7b | H | NHC(O)Me | H | 2.7 |
| A7c | H | H | NHC(O)Me | 2.6 |

TABLE 2

Antiproliferative activity.

| Compound | X—Y | EC$_{50}$ MIA PaCa-2 (μM) |
|---|---|---|
| B1 | N-methyl amide linker | 17 |
| B2 | N-methyl amine linker | 6.1 |
| B3 | N-sulfonamide linker | 25 |

TABLE 3

Antiproliferative activity.

[Structure: N-methyl-benzamide-CH2-pyrazole(3,5-dimethyl)-NH-C(O)-phenyl-R]

C1-C5, C7

[Structure: N-methyl-benzamide-CH2-pyrazole(3,5-dimethyl)-NH-C(O)-phenyl-CH2-O-phenyl]

C6

| Compound | R | EC$_{50}$ MIA PaCa-2 (μM) |
|---|---|---|
| C1 | -CH2-S-phenyl | 8.3 |
| C2 | -CH2-NH-phenyl | 17 |
| C3 | -CH2-CH2-phenyl | 5.4 |
| C4 | -C(O)-NH-phenyl | 69 |
| C5 | -CH2-O-CH2-phenyl | 8.2 |
| C6 | NA | 32 |
| C7 | -CH2-O-cyclohexyl | 14 |

NA, not applicable.

TABLE 4

Antiproliferative activity.

[Structure: N-methyl-benzamide-CH2-pyrazole(3,5-dimethyl)-NH-C(O)-phenyl-CH2-O-R]

| Compound | R | EC$_{50}$ MIA PaCa-2 (μM) |
|---|---|---|
| D1 | 2-naphthyl | 9.1 |
| D2 | 1-naphthyl | 6.0 |

TABLE 5

Antiproliferative activity.

[Structure D3a-D10: N-methyl-benzamide-CH2-pyrazole(3,5-dimethyl)-NH-C(O)-phenyl-CH2-O-phenyl(R1,R2,R3)]

D3a-D10

[Structure D11-D12: N-acetyl-amino-phenyl-CH2-pyrazole(3,5-dimethyl)-NH-C(O)-phenyl-CH2-O-phenyl(R1,R2,R3)]

D11-D12

| Compound | R$^1$ | R$^2$ | R$^3$ | EC$_{50}$ (MIA PaCa-2) (μM) |
|---|---|---|---|---|
| D3a | Me | H | H | 2.1 |
| D3b | H | Me | H | 6.2 |
| D3c | H | H | Me | 2.6 |
| D4a | OMe | H | H | 8.5 |
| D4b | H | OMe | H | 6.2 |
| D4c | H | H | OMe | 8.0 |
| D5a | Cl | H | H | 6.3 |
| D5b | H | Cl | H | 5.9 |
| D5c | H | H | Cl | 4.2 |
| D6a | F | H | H | 5.6 |
| D6b | H | F | H | 7.7 |
| D6c | H | H | F | 3.1 |
| D7a | CN | H | H | 12 |
| D7b | H | CN | H | 10 |
| D7c | H | H | CN | 5.6 |
| D8a | NO$_2$ | H | H | 11 |
| D8b | H | NO$_2$ | H | 10 |
| D8c | H | H | NO$_2$ | 9.7 |
| D9a | CF$_3$ | H | H | 10 |

TABLE 5-continued

Antiproliferative activity.

D3a-D10

D11-D12

| Compound | R¹ | R² | R³ | EC$_{50}$ (MIA PaCa-2) (μM) |
|---|---|---|---|---|
| D9b | H | CF$_3$ | H | 2.3 |
| D9c | H | H | CF$_3$ | 0.80 |
| D10 | Me | H | CF$_3$ | 0.62 |
| D11 | H | H | CF$_3$ | 0.87 |
| D12 | Me | H | CF$_3$ | 1.1 |

TABLE 6

Antiproliferative activity.

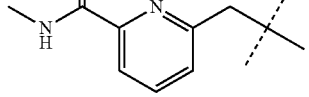

E1a-E4b

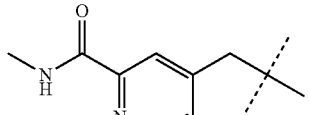

E5a-b

| Compound | R¹ | R² | MIA PaCa-2 EC$_{50}$ (μM) |
|---|---|---|---|
| E1a | 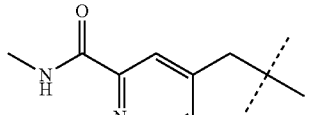 | H | 0.48 |

TABLE 6-continued

Antiproliferative activity.

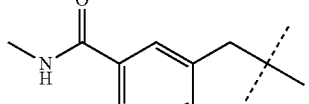

E1a-E4b

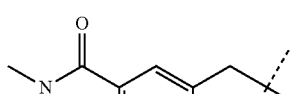

E5a-b

| Compound | R¹ | R² | MIA PaCa-2 EC$_{50}$ (μM) |
|---|---|---|---|
| E1b | (structure) | Me | 6.3 |
| E2a | (structure) | H | 0.85 |
| E2b | (structure) | Me | 0.33 |
| E3a | (structure) | H | 8.6 |
| E3b | (structure) | Me | 7.6 |

TABLE 6-continued

Antiproliferative activity.

Structure E1a-E4b: R¹-pyrazole(3,5-dimethyl)-NH-C(O)-phenyl-CH₂-O-phenyl(R²)-CF₃

Structure E5a-b: R¹-pyrazole(3,5-dimethyl)-NH-C(O)-pyridyl-CH₂-O-phenyl(R²)-CF₃

| Compound | R¹ | R² | MIA PaCa-2 EC₅₀ (μM) |
|---|---|---|---|
| E4a | N-methylcarboxamide-pyridin-2-yl (N at 6) | H | 13 |
| E4b | N-methylcarboxamide-pyridin-2-yl (N at 6) | Me | 4.9 |
| E5a | N-methylcarboxamide-phenyl | Me | 6.7 |
| E5b | N-methylcarboxamide-pyridin-2-yl (N at 4) | Me | 9.4 |

TABLE 7

Antiproliferative activity.

Structure: R¹-pyrazole(3,5-dimethyl)-NH-C(O)-phenyl-O-phenyl(R³)(R²)

| Compound | R¹ | R² | R³ | MIA PaCa-2 EC₅₀ (μM) |
|---|---|---|---|---|
| E6a | N-methylcarboxamide-phenyl | H | H | 8.4 |
| E6b | N-methylcarboxamide-phenyl | CF₃ | H | 4.6 |
| E6c | N-methylcarboxamide-phenyl | CF₃ | Me | 1.2 |
| E7a | N-methylcarboxamide-pyridin-2-yl (N at 4) | CF₃ | H | 8.1 |
| E7b | N-methylcarboxamide-pyridin-2-yl (N at 4) | CF₃ | Me | 10 |

TABLE 8

Antiproliferative activity.

| Compound | R¹ | R² | R³ | R⁴ | MIA PaCa-2 EC$_{50}$ (μM) |
|---|---|---|---|---|---|
| F1 | 3-(methylcarbamoyl)benzyl | H | H | Me | 22 |
| F2 | 3-(methylcarbamoyl)benzyl | H | H | H | 7.7 |
| F3 | 3-(methylcarbamoyl)benzyl | CF$_3$ | Me | H | 2.4 |
| F4 | 4-(methylcarbamoyl)pyridin-2-yl | CF$_3$ | Me | H | 4.0 |

TABLE 9

Antiproliferative activity.

| Compound | R | MIA PaCa-2 EC$_{50}$ (μM) |
|---|---|---|
| G1 | 2-pyridyl | >100 |
| G2 | 3-pyridyl | 24 |
| G3 | 4-pyridyl | 99 |

Example 80

Cell Viability Assay in Panc-1 Cells

Panc-1 cells are maintained in RPMI 1640 (Invitrogen 11875) media supplemented with 10% FBS, 1% Penicillin/Streptomycin and 1% Glutamax-1. Cells were plated in 96-well plates at 25×10⁴ cells/ml. After 24 hours, compounds were added at 9, 3× dilutions in triplicate from 100 uM final concentration in the appropriate growth media. Plates were incubated for 72 hours at 37° C. in a 5% $CO_2$/95% air humidified atmosphere after which time the media was removed and MTT was added in RPMI phenol red free media. The MTT was removed after 3 hours and formazan crystals were solubilized with 200 μL of isopropanol. Plates were read on a Molecular Devices SpectraMax i3 spectrophotometer at 570 nm for formazan and 690 nm for background subtraction. EC50 values were calculated by fitting the data in GraphPad Prism software. Data for representative compounds is provided in Table 10.

TABLE 10

Antiproliferative activity.

| Compound | Panc-1 EC$_{50}$ (μM) |
|---|---|
| A1 | 9.0 |
| A2a | >100 |
| A2b | 11 |
| A2c | >100 |
| A3a | 36 |
| A3b | 5.2 |
| A3c | 14 |
| A4a | 1.2 |
| A4b | 1.6 |
| A4c | 1.4 |
| A5a | 23 |
| A5b | 20 |
| A5c | 5.3 |
| A6a | 44 |
| A6b | 9.7 |
| A6c | 22 |
| A7a | >100 |
| A7b | 12 |
| A7c | 31 |
| C3 | 0.76 |
| C4 | 51 |
| C5 | 6.0 |

TABLE 10-continued

Antiproliferative activity.

| Compound | Panc-1 EC$_{50}$ (µM) |
|---|---|
| D2 | 1.3 |
| D3a | 0.61 |
| D3b | 0.56 |
| D3c | 13 |
| D4a | 25 |
| D4b | 6.2 |
| D4c | 48 |
| D5a | 9.9 |
| D5b | 0.038 |
| D5c | 2.0 |
| D6a | 3.0 |
| D6b | 0.21 |
| D6c | 6.9 |
| D7a | 8.5 |
| D7c | 22 |
| D9a | 0.44 |
| D9b | 0.76 |
| D9c | 0.21 |

Example 81

Cell Viability Assay in MCF10A Cells (Normal Human Mammary Cells)

MCF10A cells are maintained in minimum essential medium (MEM) (Invitrogen 11095) supplemented with 10% FBS (Invitrogen 16000), 1% 10× non-essential amino acids (NEAA) (Invitrogen 11140), 1% Penicillin/Streptomycin (Invitrogen 15140), 1% GlutaMAX (Invitrogen 35050-061), 20 ng/mL EGF, 0.5 mg/mL hydrocortisone, 100 ng/mL cholera toxin, 10 µg/mL insulin.

Cells were plated in 96-well plates at 25×10$^4$ cells/ml. After 24 hours, compounds were added at 9, 3× dilutions in triplicate from 100 uM final concentration in the appropriate growth media. Plates were incubated for 72 hours at 37° C. in a 5% CO$_2$/95% air humidified atmosphere after which time the media was removed and MTT was added in RPMI phenol red free media. The MTT was removed after 3 hours and formazan crystals were solubilized with 200 µL of isopropanol. Plates were read on a Molecular Devices SpectraMax i3 spectrophotometer at 570 nm for formazan and 690 nm for background subtraction. EC50 values were calculated by fitting the data in GraphPad Prism software. Data for representative compounds is provided in Table 11.

TABLE 11

Antiproliferative activity.

| Compound | MCF10A EC$_{50}$ (µM) |
|---|---|
| D9c | 6.7 |
| D10 | 4.8 |
| D11 | 8.6 |
| D12 | 6.6 |
| E1a | 7.8 |
| E2a | 8.3 |
| E2b | 7.4 |

Example 82

In Vitro ADME Evaluation

Plasma Stability Assay

The plasma stability assay was performed in triplicate by incubating a compound in normal mouse and human plasma at 37° C. At 0, 1, 3, 6, and 24 h, aliquots of the plasma mixture were taken and quenched with 3 volumes of acetonitrile containing an appropriate internal standard. The samples were then vortexed and centrifuged at 14,000 rpm for 5 min. The supernatants were collected and analyzed by LC-MS/MS to determine the remaining percentage at various time points. Data for representative compounds is provided in Table 12.

Microsomal Stability Assay

The in vitro microsomal stability assay was conducted in triplicate in mouse and human liver microsomal systems. In a typical incubation, a compound (typically 1 µM final concentration) was spiked into the reaction mixture containing 0.5 mg/mL of liver microsomal protein and 1 mM of NADPH in 0.1 M potassium phosphate buffer (pH 7.4) at 37° C. At various time points, 1 volume of reaction aliquot was taken and quenched with 3 volumes of acetonitrile with an appropriate internal standard. The samples were then vortexed and centrifuged at 14,000 rpm for 5 min. The supernatants were collected and analyzed by LC-MS/MS to determine the in vitro metabolic half-life ($t_{1/2}$) and intrinsic clearance ($CL_{int}$). Verapamil was used as a positive control. Data for representative compounds is provided in Table 12.

LC-MS/MS Bioanalysis

Quantification and analysis of compounds in biological samples were carried out on an AB Sciex QTrap 5500 mass spectrometer coupled with an Agilent 1260 Infinity HPLC. The chromatographic separation of compounds was achieved using a Phenomenex Kinetex C18 column (50×2.1 mm, 2.6 µm), and MS/MS analysis was conducted using an ESI ion source with MRM detection. The MS/MS detection parameters including declustering potential (DP), entrance potential (EP), collision energy (CE), and collision cell exit potential (CXP) were optimized for each compound.

Thermodynamic Solubility Assay

The aqueous solubility of a test compound was determined in DPBS (pH=7.4) under thermodynamic solubility conditions. Briefly, a saturated solution was made by adding DPBS to the solid compound. The mixture was shaken at 200 rpm for 48 h in a MaxQ 6000 orbital shaker at ambient temperature to allow equilibrium between the solid and dissolved compound. The suspension was then filtered through a 0.45 µm PVDF syringe filter and the filtrate was collected for analysis using UV spectrometry (SpectraMax M5e, Molecular Devices) at λ=240 nm. Data for representative compounds is provided in Table 12.

TABLE 12

In Vitro ADME Properties of Selected Compounds.[a]

| Compound | Plasma Stability (% remaining, 6 h/24 h) | | Microsomal Stability $t_{1/2}$ (min) | | Aqueous Solubility (µM) |
|---|---|---|---|---|---|
| | Mouse | Human | Mouse | Human | |
| D9c | 91/77 | 99/100 | 60 | 34 | 67.3 ± 5.2 |
| D10 | 88/93 | 98/100 | 53 | 53 | 166 ± 2 |
| D11 | 2.1/0.1 | 96/94 | 7.4 | 8.3 | |
| D12 | 1.6/0.1 | 92/95 | 9.7 | 14 | |
| E1a | —/99 | —/100 | 65 | 47 | |

TABLE 12-continued

In Vitro ADME Properties of Selected Compounds.[a]

| Compound | Plasma Stability (% remaining, 6 h/24 h) | | Microsomal Stability $t_{1/2}$ (min) | | Aqueous Solubility ($\mu$M) |
|---|---|---|---|---|---|
| | Mouse | Human | Mouse | Human | |
| E1b | —/96 | —/100 | 75 | 47 | |
| E2a | —/91 | —/98 | 64 | 112 | |
| E2b | —/84 | —/100 | 89 | 89 | 211 ± 5 |
| E3a | —/100 | —/94 | 144 | 82 | |
| E3b | —/100 | —/98 | 139 | 74 | |
| E4a | —/98 | —/97 | 151 | 65 | |
| E4b | —/99 | —/98 | 126 | 57 | |

[a]Plasma and microsomal stabilities as well as aqueous solubility were determined in triplicate.

Example 83

Caco-2 Permeability Assay

Cell Culture. The human colon adenocarcinoma cell line Caco-2 was purchased from ATCC (American Type Culture Collection, Manassas, Va.), and was cultured in a humidified atmosphere of 5% CO2 at 37° C. Caco-2 cells were cultured in DMEM with 10% FBS, 1% NEAA, 1% GlutaMax and 1% penicillin and streptomycin solution. The culture medium was changed every other day during cell growth and differentiation. On achieving 80-90% confluence, the cells were rinsed with pre-warm DPBS (pH 7.4) and split using trypsin. The cells were then seeded on membranes of Millipore Millicell-24 cell culture device. The transepithelial electrical resistance (TEER) were assessed to reflect membrane integrity using a Millicells® ERS-2 (Millipore, USA). The Caco-2 cell monolayers were used for transport experiments on day 21 post-seeding with TEER values >500 $\Omega \cdot cm^2$.

Bidirectional Transport Experiments. Before the transport experiments, the cell monolayer was washed three times with HBSS. Then, the plates were incubated in fresh permeability assay buffer (HBSS containing 10 mM glucose and 20 mM HEPES, pH 7.4) at 37° C. The experiments were conducted by spiking test compounds to either the apical (AP, 0.4 mL) or basolateral side (BL, 0.8 mL), while the receiving chamber contained the corresponding volume of pre-warmed permeability assay buffer. Every experiment was repeated in duplicate, and the plates were incubated in an orbital shaker at 37° C., 50 rpm/min. To assess the drug transport, at the incubation time of 20, 40, 60 and 80 min, aliquot was removed and was immediately replenished with an equal volume of permeability assay buffer. The samples were then subjected to LC/MS/MS analysis. The apparent permeability coefficient was indicated by the absorption rate constant Papp. It could be calculated as PBA (measured in BL to AP direction) or PAB (measured in AP to BL direction), using the equation of Papp=(dQ/dt)/(A×C0). dQ/dt is the rate at which the compound appears in the receiver chamber (nmol/s), A is the surface area of the filter membrane (0.7 cm2) and C0 is the initial concentration in the donor chamber ($\mu$M). Efflux ratio (ER) was calculated by the equation of ER=PBA/PAB, where PBA is the Papp value measured in BL to AP direction, and PAB is the Papp value measured in AP to BL direction. Data for representative compounds is provided in Table 13.

TABLE 13

Caco-2 Permeability.

| Compound | Caco-2 $P_{app}$ ($\times 10^{-6}$ cm/sec) | |
|---|---|---|
| | A to B | B to A |
| D9c | 8.26 | 19.3 |
| D10 | 3.72 | 11.2 |
| E1a | 24.5 | 21.0 |
| E1b | 3.58 | 7.17 |
| E2a | 5.02 | 5.69 |
| E2b | 8.34 | 5.96 |

Example 84

The following illustrate representative pharmaceutical dosage forms, containing a compound of formula I (compound X), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

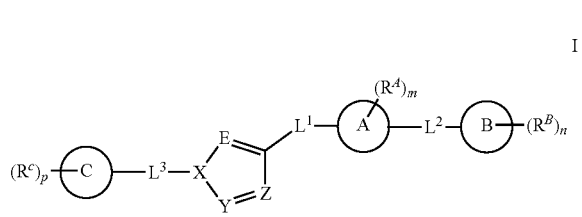

I wherein:
ring A is aryl;
ring B is aryl, heteroaryl, carbocycle or heterocycle;
$L^1$ is —NHC(O)—* or -$L^A$-NR$^1$SO$_2$-$L^B$-, wherein each $R^1$ is hydrogen; each $L^A$ is absent; each $L^B$ is absent, wherein * indicates the point of attachment to A;
$L^2$ is $C_{1-4}$ alkylene, -$L^C$-O-$L^D$-, -$L^C$-S-$L^D$-, -$L^C$-NR$^2$-$L^D$-, -$L^C$-NR$^2$C(O)-$L^D$-, or -$L^C$-C(O)NR$^2$-$L^D$-; wherein each $R^2$ is independently hydrogen or $C_{1-4}$ alkyl; each $L^C$ is independently absent or $C_{1-4}$ alkylene; each $L^D$ is independently absent or $C_{1-4}$ alkylene;
$L^3$ is $C_{1-4}$ alkylene,;
X is N;
Y is N;
Z is C—R$^Z$; wherein R$^Z$ is hydrogen, $C_{1-4}$ alkyl, $C_{1-4}$ haloalkyl, halo, —OR$^5$, —SR$^5$, —N(R$^5$)$_2$, —NO$_2$ or —CN; wherein each R$^5$ is independently hydrogen or $C_{1-4}$ alkyl;
E is C—R$^E$; wherein R$^E$ is hydrogen, $C_{1-4}$ alkyl, $C_{1-4}$ haloalkyl, halo, —OR$^6$, —SR$^6$, —N(R$^6$)$_2$, —NO$_2$ or —CN; wherein each R$^6$ is independently hydrogen or $C_{1-4}$ alkyl;
each R$^A$ is independently $C_{1-4}$ alkyl, $C_{1-4}$ haloalkyl, halo, —OR$^7$, —SR$^7$, —N(R$^7$)$_2$, —NO$_2$ or —CN; wherein each R$^7$ is independently hydrogen or $C_{1-4}$ alkyl;

each R$^B$ is independently $C_{1-4}$ alkyl, $C_{1-4}$ haloalkyl, halo, —OR$^8$, —SR$^8$, —N(R$^8$)$_2$, —NO$_2$ or —CN; wherein each R$^8$ is independently hydrogen or $C_{1-4}$ alkyl;
m is 0, 1, 2, 3, or 4;
n is 0, 1, 2, 3, or 4; and the group

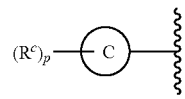

is selected from the group consisting of:

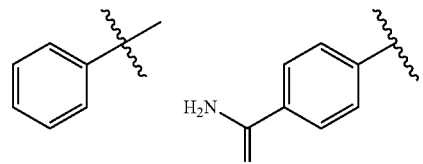

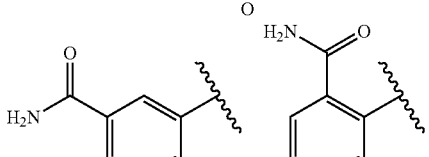

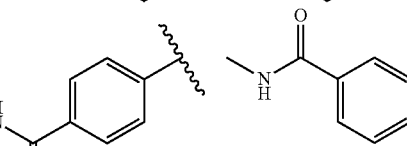

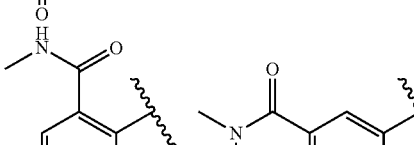

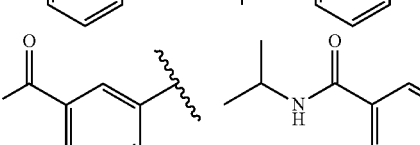

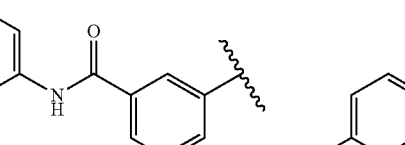

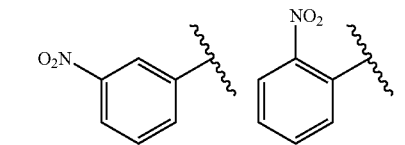

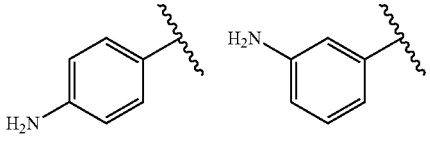

-continued

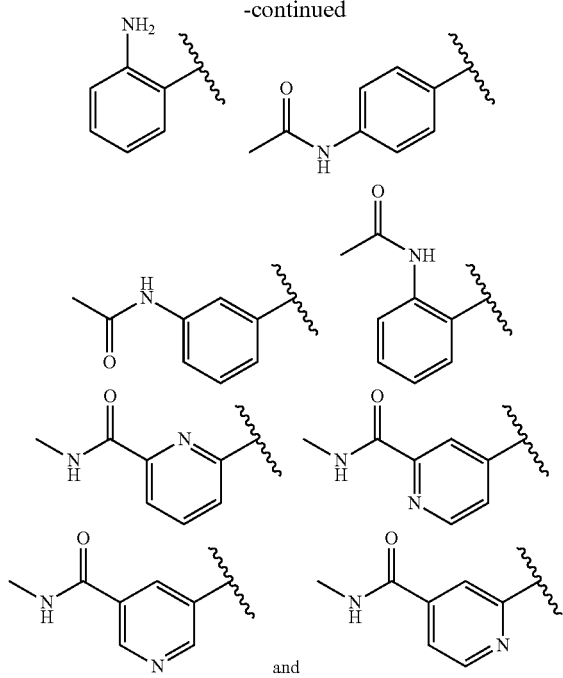

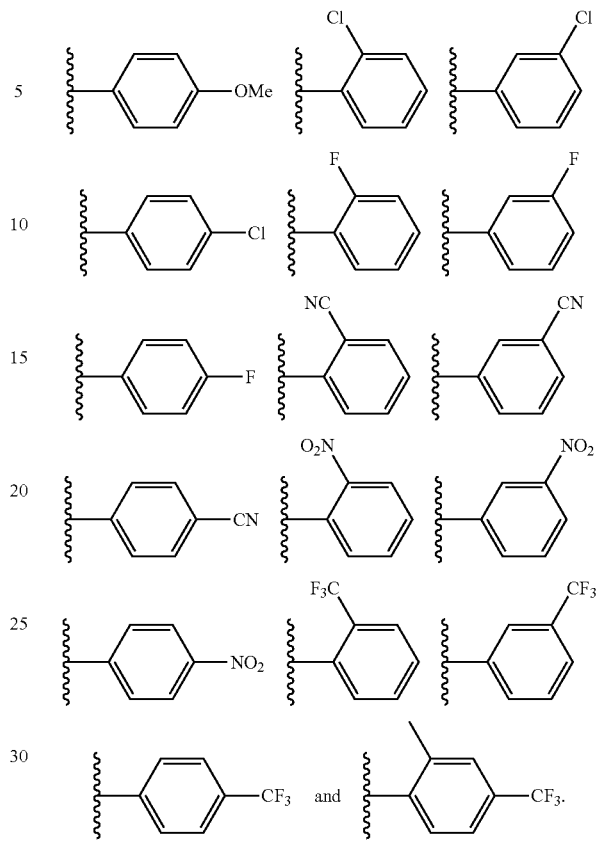

or a pharmaceutically acceptable salt thereof.

2. The compound or salt of claim 1, wherein $R^Z$ is $C_{1-4}$ alkyl.

3. The compound or salt of claim 1, wherein $R^E$ is $C_{1-4}$ alkyl.

4. The compound or salt of claim 1, wherein ring B is phenyl, pyridyl, cyclohexyl or naphthalenyl.

5. The compound or salt of claim 1, wherein the group

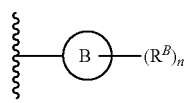

is selected from the group consisting of:

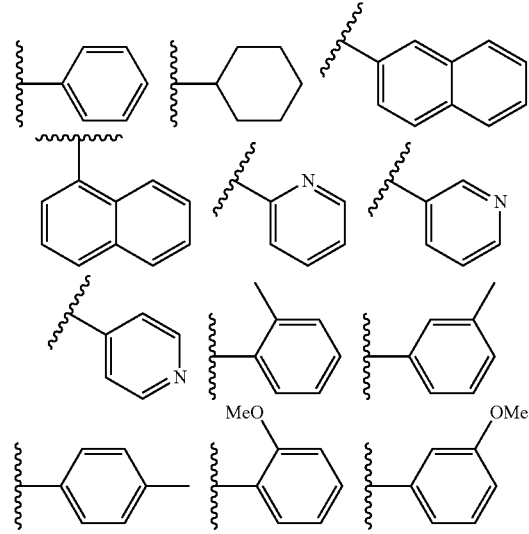

6. The compound or salt of claim 1, wherein $L^1$ is —NHC(O)—*.

7. The compound or salt of claim 1, wherein $L^2$ is —CH$_2$O—.

8. The compound of claim 1, wherein $L^3$ is —CH$_2$— or —CH(CH$_3$)—.

9. The compound selected from the group consisting of:

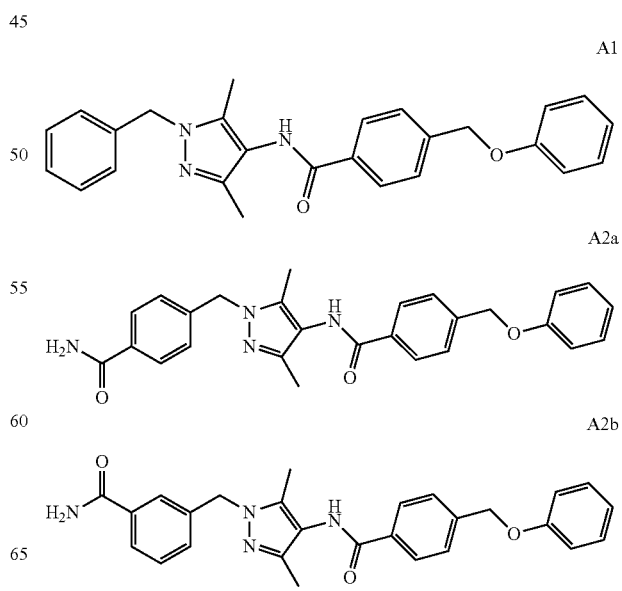

A2c
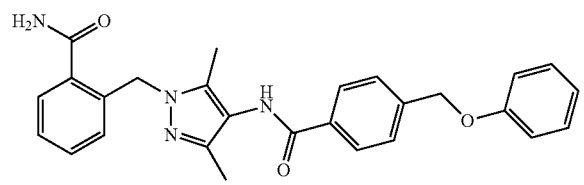
A3a
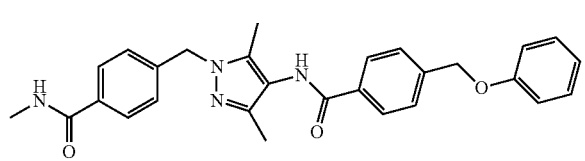
A3b
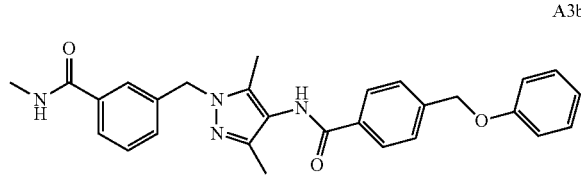
A3c
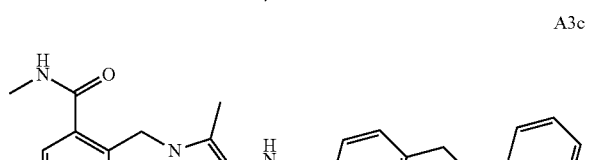
A4a
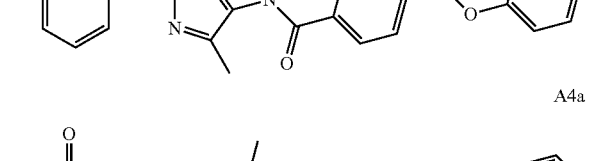
A4b
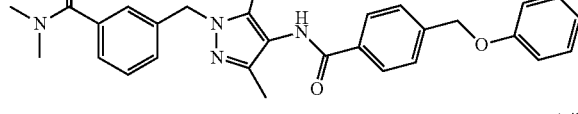
A4c
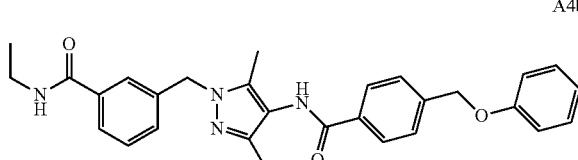
A4d
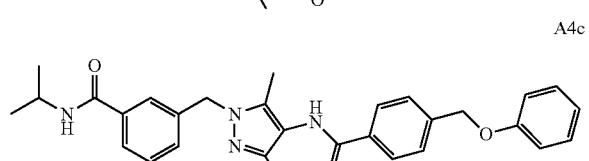
A5a
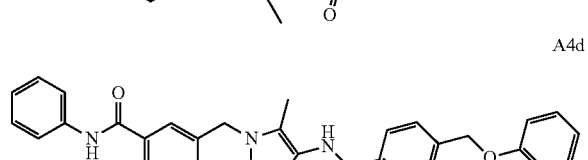
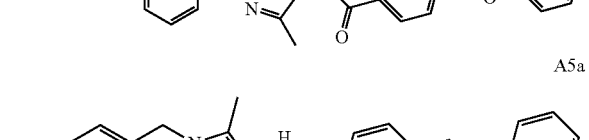
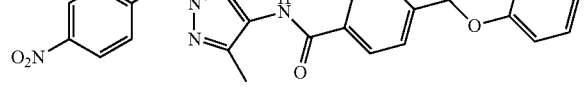
A5b
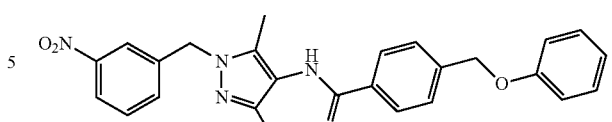
A5c
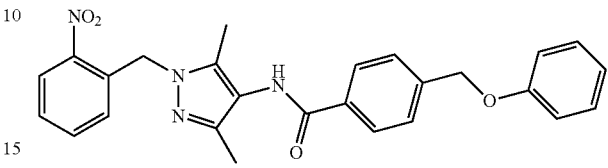
A6a
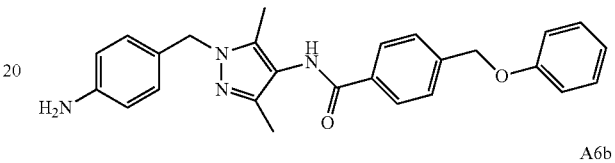
A6b
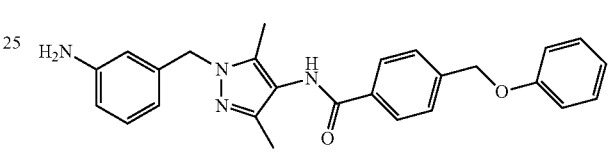
A6c
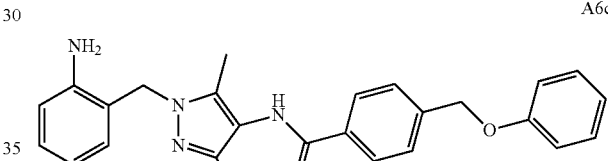
A7a
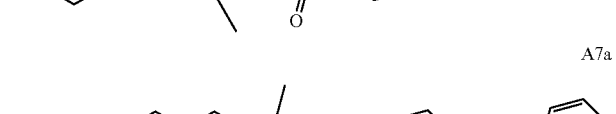
A7b
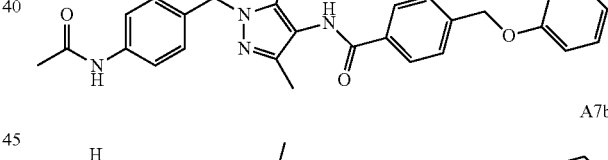
A7c
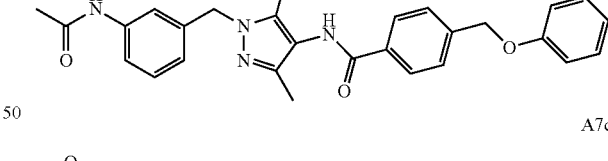
B1
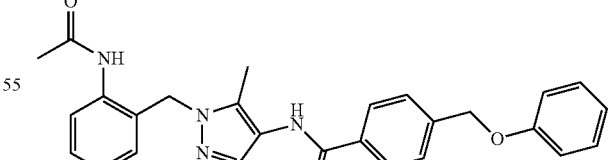
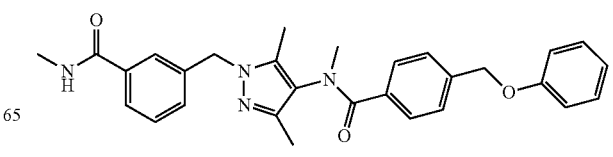

B2
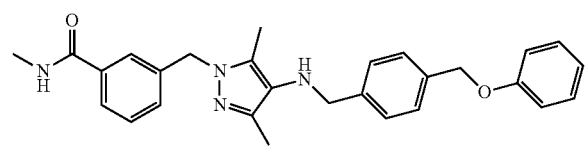
B3
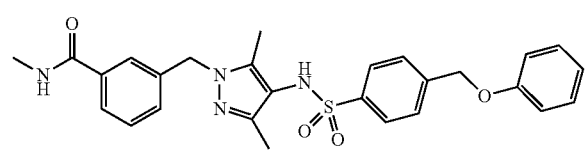
C1
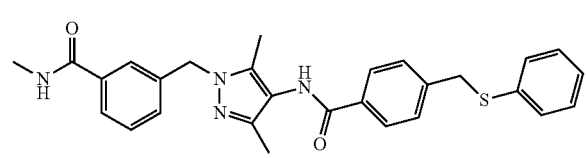
C2
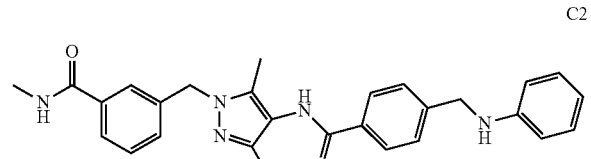
C3
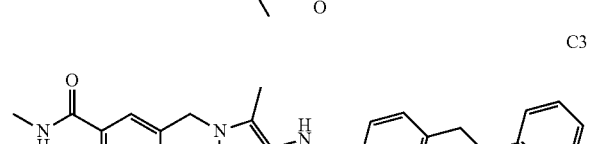
C4
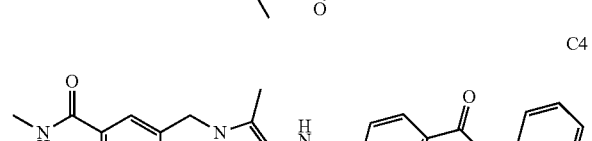
C5
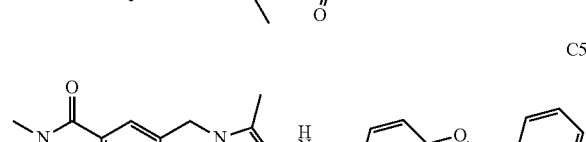
C6
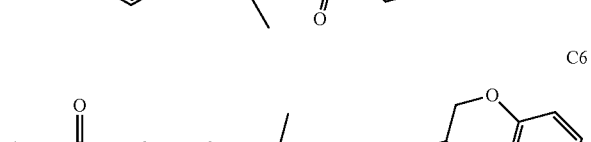
C7
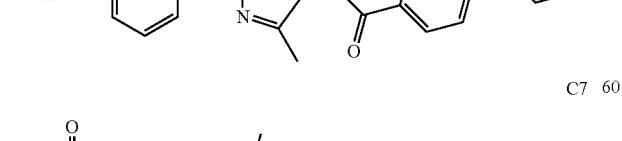
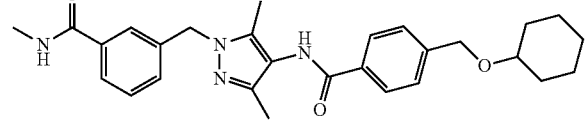
D1
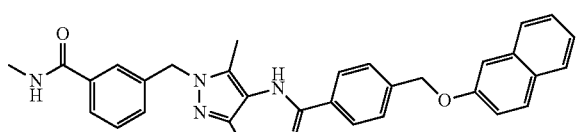
D2
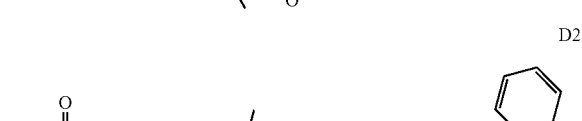
D3a
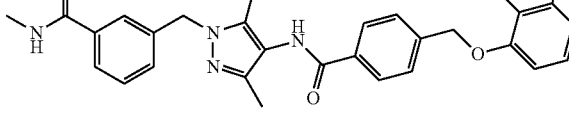
D3b
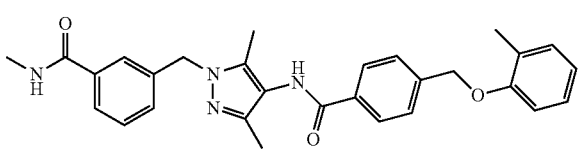
D3c
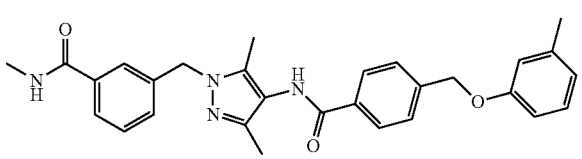
D4a
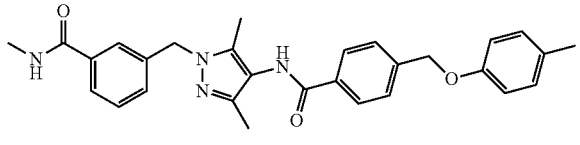
D4b
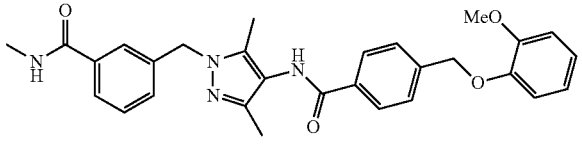
D4c
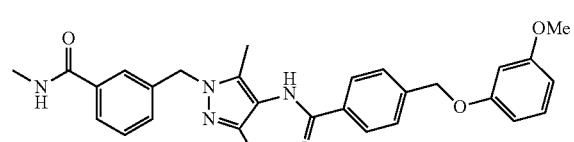
D5a
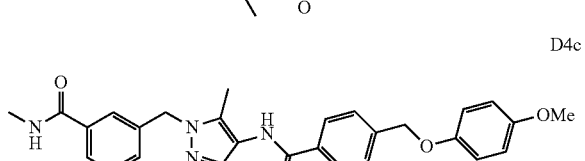

D5b 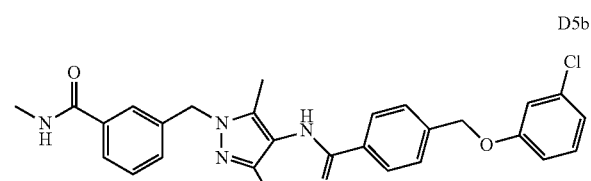
D5c 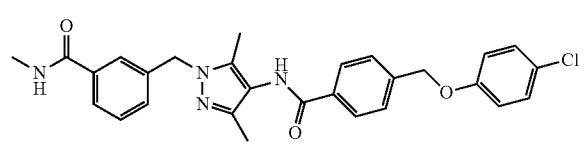
D6a 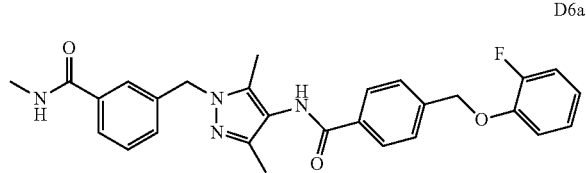
D6b 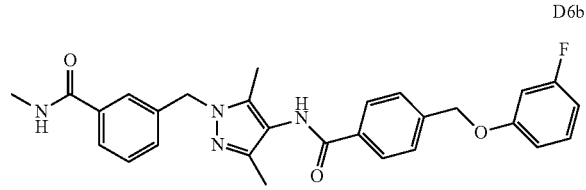
D6c 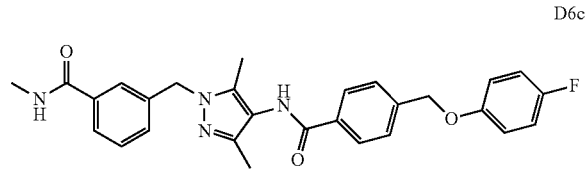
D7a 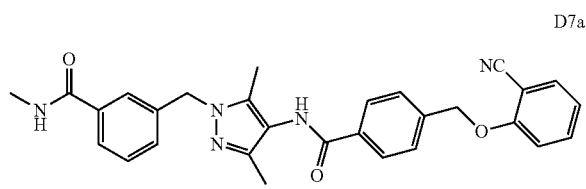
D7b 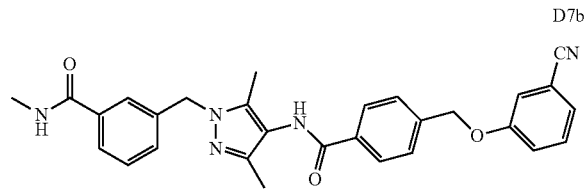
D7c 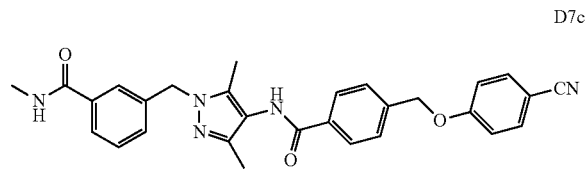
D8a 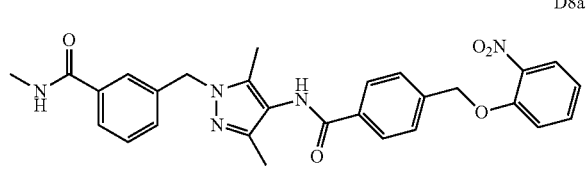
D8b 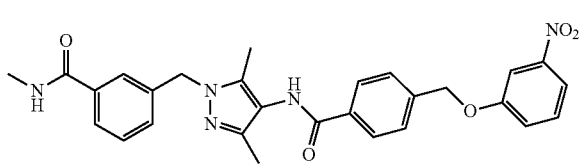
D8c 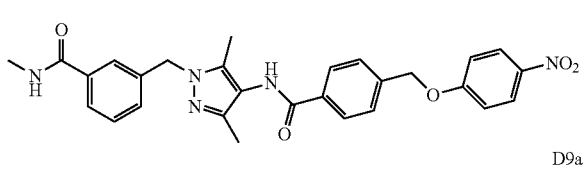
D9a 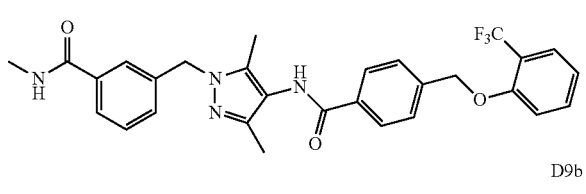
D9b 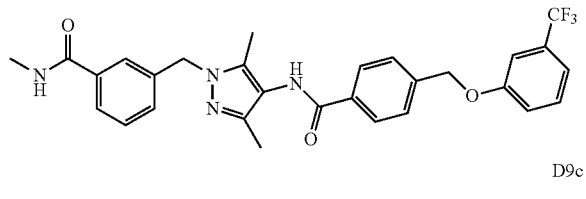
D9c 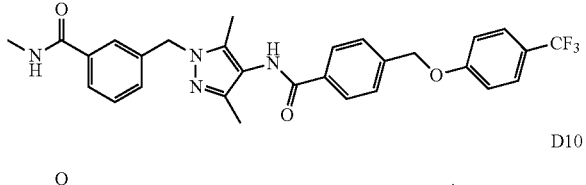
D10 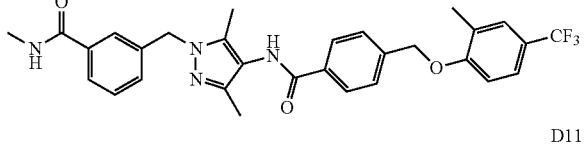
D11 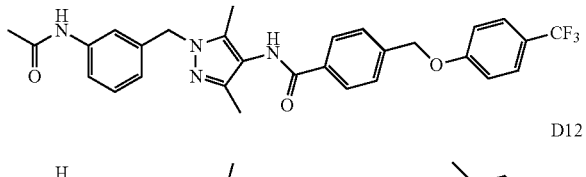
D12 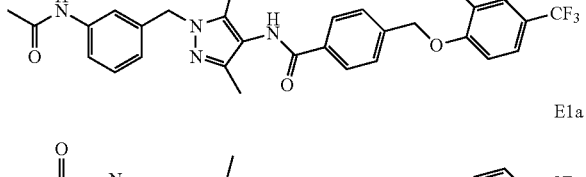
E1a 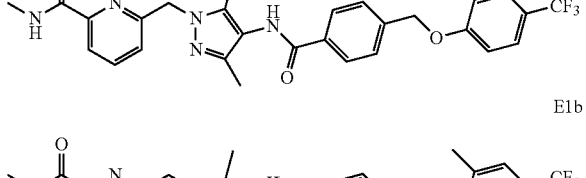
E1b 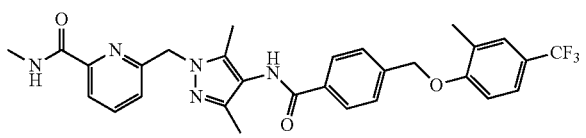

-continued

E2a, E2b, E3a, E3b, E4a, E4b, E5a, E5b, E6a, E6b, E6c, E7a, E7b, F1, F2, F3, F4, G1

-continued

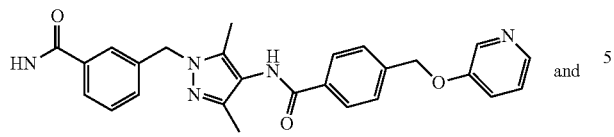

and

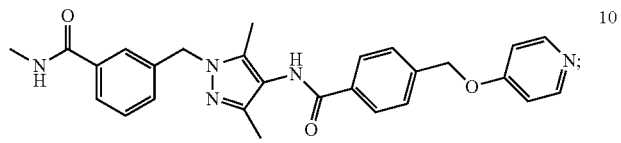

or a pharmaceutically acceptable salt thereof.

10. A pharmaceutical composition comprising a compound of formula I as described in claim 1, or a pharmaceutically acceptable salt thereof, and a pharmaceutically acceptable carrier.

11. The compound:

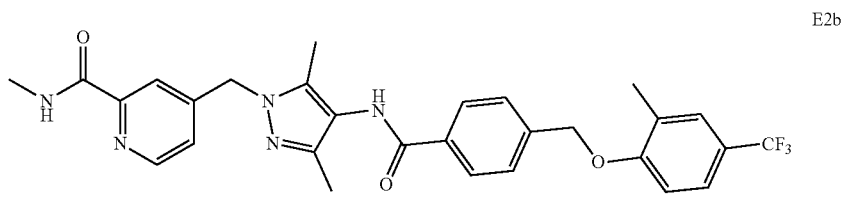 [SMILES: CNC(=O)c1cc(Cn2nc(C)c(NC(=O)c3ccc(COc4ccc(C(F)(F)F)cc4C)cc3)c2C)ccn1]

or a pharmaceutically acceptable salt thereof.

12. The compound or salt of claim 1, wherein the group

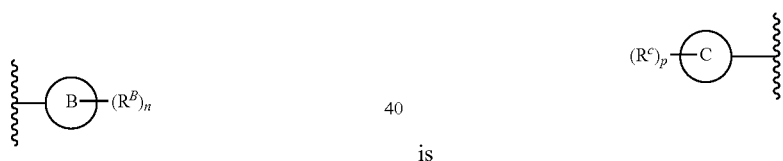

is

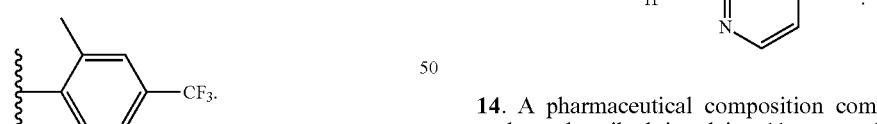

13. The compound or salt of claim 1, wherein the group (R^C)_p—(C)— is (methylcarbamoyl-pyridyl structure)

14. A pharmaceutical composition comprising a compound as described in claim 11, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO.       : 10,357,477 B2
APPLICATION NO.  : 15/703191
DATED            : July 23, 2019
INVENTOR(S)      : Liqiang Chen and Teng Ai It is certified that error appears in the above-identified patent and that said Letters Patent is hereby corrected as shown below:

In the Claims

Column 84, Line 43, Claim 9, please delete "The compound" and insert -- A compound -- therefor.

Signed and Sealed this
Fifth Day of November, 2019

Andrei Iancu
*Director of the United States Patent and Trademark Office*